(12) United States Patent
Anthony et al.

(10) Patent No.: US 7,781,454 B2
(45) Date of Patent: Aug. 24, 2010

(54) NON-NUCLEOSIDE REVERSE TRANSCRIPTASE INHIBITORS

(75) Inventors: Neville J. Anthony, Chalfont, PA (US); Robert Gomez, Perkasie, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 244 days.

(21) Appl. No.: 11/999,686

(22) Filed: Dec. 6, 2007

(65) Prior Publication Data

US 2008/0275097 A1 Nov. 6, 2008

Related U.S. Application Data

(60) Provisional application No. 60/874,629, filed on Dec. 13, 2006.

(51) Int. Cl.
| | |
|---|---|
| A01N 43/42 | (2006.01) |
| A61K 31/44 | (2006.01) |
| A61K 31/415 | (2006.01) |
| C07D 471/02 | (2006.01) |
| C07D 491/02 | (2006.01) |
| C07D 498/02 | (2006.01) |
| C07D 213/56 | (2006.01) |

(52) U.S. Cl. .................. 514/303; 514/406; 546/119; 548/362.1; 548/362.5

(58) Field of Classification Search .................. 546/119; 548/362.1, 362.5; 514/303, 406

See application file for complete search history.

(56) References Cited

U.S. PATENT DOCUMENTS

| | | | |
|---|---|---|---|
| 4,036,976 A * | 7/1977 | Neumann | .............. 514/402 |
| 5,527,819 A | 6/1996 | Williams et al. | |
| 6,977,262 B2 | 12/2005 | Kohara et al. | |
| 7,166,738 B2 | 1/2007 | Dunn et al. | |
| 7,208,509 B2 | 4/2007 | Dunn et al. | |
| 7,220,760 B2 | 5/2007 | Awad et al. | |
| 7,348,345 B2 | 3/2008 | Dunn et al. | |
| 7,625,949 B2 | 12/2009 | Dunn et al. | |
| 7,666,891 B2 | 2/2010 | Dunn et al. | |
| 2004/0180945 A1 | 9/2004 | Artico et al. | |
| 2004/0192653 A1 | 9/2004 | Munson et al. | |
| 2005/0197340 A1 | 9/2005 | Arora et al. | |
| 2005/0203091 A1 | 9/2005 | Arora et al. | |
| 2005/0272765 A1 | 12/2005 | Feng et al. | |
| 2007/0021442 A1 | 1/2007 | Saggar et al. | |
| 2008/0045511 A1 | 2/2008 | Kennedy-Smith et al. | |

FOREIGN PATENT DOCUMENTS

| | | |
|---|---|---|
| WO | WO 2005/054232 A1 | 6/2005 |
| WO | WO 2005/115147 A2 | 12/2005 |
| WO | WO 2007/002368 A2 | 1/2007 |
| WO | WO 2007/002458 A2 | 1/2007 |
| WO | WO 2007/002481 A2 | 1/2007 |
| WO | WO 2007/015812 A2 | 2/2007 |

OTHER PUBLICATIONS

Castro et al. "HIV-1 Reverse Transcriptase: A Therapeutical Target in the Spotlight", Current Medicinal Chemistry, 2006, vol. 13, pp. 313-324.

De Clercq, "Non-Nucleoside Reverse Transcriptase Inhibitors (NNRTIs): Past, Present, and Future", Chemistry & Biodiversity, 2004, vol. 1, pp. 44-64.

* cited by examiner

*Primary Examiner*—D. Margaret Seaman
*Assistant Examiner*—Niloofar Rahmani
(74) *Attorney, Agent, or Firm*—Kenneth R. Walton; Sheldon O. Heber

(57) ABSTRACT

Compounds of Formula I:

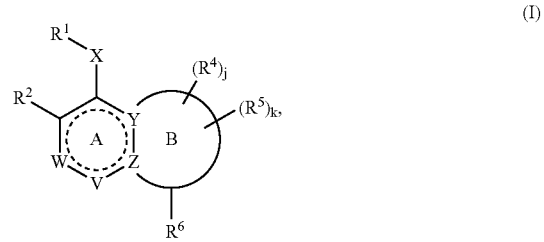

are HIV reverse transcriptase inhibitors, wherein V, W, X, Y, Z, $R^1$, $R^2$, $R^4$, $R^5$, $R^6$, ring A, ring B, j and k are defined herein. The compounds of Formula I, and the pharmaceutically acceptable salts and prodrugs thereof, are useful in the inhibition of HIV reverse transcriptase, the prophylaxis and treatment of infection by HIV and in the prophylaxis, delay in the onset or progression, and treatment of AIDS. The compounds and their salts can be employed as ingredients in pharmaceutical compositions, optionally in combination with other antivirals, immunomodulators, antibiotics or vaccines.

18 Claims, No Drawings

NON-NUCLEOSIDE REVERSE TRANSCRIPTASE INHIBITORS

This application claims the benefit of U.S. Provisional Application No. 60/874,629, filed Dec. 13, 2006, the disclosure of which is hereby incorporated by reference in its entirety.

FIELD OF THE INVENTION

The present invention is directed to certain substituted indazoles, benzotriazoles, and related bicyclic compounds and their pharmaceutically acceptable salts and their use for the inhibition of HIV reverse transcriptase, the prophylaxis of HIV infection and HIV replication, the treatment of HIV infection and HIV replication, the prophylaxis of AIDS, the treatment of AIDS, and the delay in the onset and/or progression of AIDS.

BACKGROUND OF THE INVENTION

The retrovirus designated human immunodeficiency virus (HIV), particularly the strains known as HIV type-1 (HIV-1) and type-2 (HIV-2) viruses, have been etiologically linked to the immunosuppressive disease known as acquired immunodeficiency syndrome (AIDS). HIV seropositive individuals are initially asymptomatic but typically develop AIDS related complex (ARC) followed by AIDS. Affected individuals exhibit severe immunosuppression which makes them highly susceptible to debilitating and ultimately fatal opportunistic infections. Replication of HIV by a host cell requires integration of the viral genome into the host cell's DNA. Since HIV is a retrovirus, the HIV replication cycle requires transcription of the viral RNA genome into DNA via an enzyme know as reverse transcriptase (RT).

Reverse transcriptase has three known enzymatic functions: The enzyme acts as an RNA-dependent DNA polymerase, as a ribonuclease, and as a DNA-dependent DNA polymerase. In its role as an RNA-dependent DNA polymerase, RT transcribes a single-stranded DNA copy of the viral RNA. As a ribonuclease, RT destroys the original viral RNA and frees the DNA just produced from the original RNA. And as a DNA-dependent DNA polymerase, RT makes a second, complementary DNA strand using the first DNA strand as a template. The two strands form double-stranded DNA, which is integrated into the host cell's genome by the integrase enzyme.

It is known that compounds that inhibit enzymatic functions of HIV RT will inhibit HIV replication in infected cells. These compounds are useful in the treatment of HIV infection in humans. Among the compounds approved for use in treating HIV infection and AIDS are the RT inhibitors 3'-azido-3'-deoxythymidine (AZT), 2',3'-dideoxyinosine (ddI), 2',3'-dideoxycytidine (ddC), d4T, 3TC, nevirapine, delavirdine, efavirenz and abacavir.

While each of the foregoing drugs is effective in treating HIV infection and AIDS, there remains a need to develop additional HIV antiviral drugs including additional RT inhibitors. A particular problem is the development of mutant HIV strains that are resistant to the known inhibitors. The use of RT inhibitors to treat AIDS often leads to viruses that are less sensitive to the inhibitors. This resistance is typically the result of mutations that occur in the reverse transcriptase segment of the pol gene. The continued use of antiviral compounds to prevent HIV infection will inevitably result in the emergence of new resistant strains of HIV. Accordingly, there is a particular need for new RT inhibitors that are effective against mutant HIV strains.

SUMMARY OF THE INVENTION

The present invention is directed to certain substituted indazoles, benzotriazoles, and related bicyclic compounds and their use in the inhibition of HIV reverse transcriptase, the prophylaxis of infection by HIV, the treatment of infection by HIV, and the prophylaxis, treatment, and delay in the onset or progression of AIDS and/or ARC. More particularly, the present invention includes compounds of Formula I and pharmaceutically acceptable salts thereof:

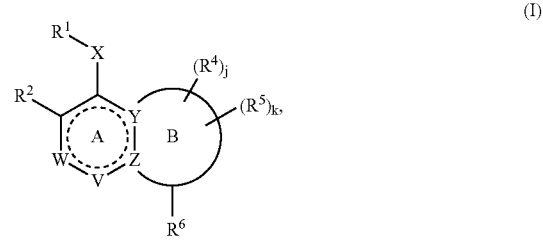

(I)

wherein:

V is $C(R^{10})$, $C(O)$, $N(R^{11})$, N or N oxide; W is $C(R^3)$, $C(O)$, $N(R^{12})$, N or N oxide; Y is C or N; and Z is C or N, with the proviso that no more than two of V, W, Y and Z contain N;

X is O, S, S(O), $S(O)_2$, $N(R^A)$, $C(R^A)(R^B)$, or C(O);

$R^1$ is AryA or HetA;

$R^2$, $R^3$ and $R^{10}$ are each independently selected from the group consisting of:
 (1) H,
 (2) halogen,
 (3) CN,
 (4) $NO_2$,
 (5) $C(O)R^A$,
 (6) $C(O)OR^A$,
 (7) $C(O)N(R^A)R^B$,
 (8) $SR^A$,
 (9) $S(O)R^A$,
 (10) $S(O)_2R^A$,
 (11) $S(O)_2N(R^A)R^B$,
 (12) $N(R^A)R^B$,
 (13) $N(R^A)S(O)_2R^B$,
 (14) $N(R^A)C(O)R^B$,
 (15) $N(R^A)C(O)OR^B$,
 (16) $N(R^A)S(O)_2N(R^A)R^B$,
 (17) $OC(O)N(R^A)R^B$,
 (18) $N(R^A)C(O)N(R^A)R^B$,
 (19) $C_{1-6}$ alkyl,
 (20) $C_{1-6}$ haloalkyl,
 (21) $C_{2-6}$ alkenyl,
 (22) $C_{2-6}$ alkynyl,
 (23) OH,
 (24) O—$C_{1-6}$ alkyl,
 (25) O—$C_{1-6}$ alkyl in which the alkyl is substituted with $OR^A$ or $N(R^A)R^B$,
 (26) O—$C_{1-6}$ haloalkyl,
 (27) $C_{1-6}$ alkyl substituted with from 1 to 3 substituents each of which is independently halogen (provided that the alkyl is further substituted with at least one non-halogen group), OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, or $N(R^A)C(O)N(R^A)R^B$,
- (28) CycE,
- (29) O-CycE,
- (30) C(O)O-CycE,
- (31) $C(O)N(R^A)$-CycE, and
- (32) $N(R^A)$-CycE;

$R^{11}$ and $R^{12}$ are each independently selected from the group consisting of H, halogen, $C_{1-6}$ alkyl and CycE;

ring A is an unsaturated 6-membered ring wherein

denotes the ring contains at least two double bonds;

ring B is fused to ring A and forms together with shared atoms Y and Z of ring A a 4- to 7-membered saturated or unsaturated ring optionally containing from 1 to 3 heteroatoms each of which is independently N, O or S, wherein the total count of heteroatoms in ring B includes either or both Y and Z when either or both are N, and wherein each S is optionally S(O) or $S(O)_2$ and each N is optionally an N-oxide, and wherein from zero to 2 ring carbons are optionally substituted with oxo;

$R^4$ and $R^5$ are each independently selected from the group consisting of:
- (1) H,
- (2) $C_{1-6}$ alkyl,
- (3) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
- (4) O—$C_{1-6}$ alkyl,
- (5) $C_{1-6}$ haloalkyl,
- (6) O—$C_{1-6}$ haloalkyl,
- (7) OH,
- (8) halogen,
- (9) CN,
- (10) $NO_2$,
- (11) $C(O)N(R^A)R^B$,
- (12) $C(O)R^A$,
- (13) C(O)—$C_{1-6}$ haloalkyl,
- (14) $C(O)OR^A$,
- (15) $SR^A$,
- (16) $S(O)R^A$,
- (17) $S(O)_2R^A$,
- (18) $S(O)_2N(R^A)R^B$,
- (19) $N(R^A)R^B$,
- (20) $N(R^A)S(O)_2R^B$,
- (21) $N(R^A)C(O)R^B$,
- (22) $N(R^A)C(O)OR^B$,
- (23) $N(R^A)S(O)_2N(R^A)R^B$,
- (24) $OC(O)N(R^A)R^B$, and
- (25) $N(R^A)C(O)N(R^A)R^B$;

j is an integer equal to zero or 1;

k is an integer equal to zero or 1;

$R^6$ is attached to the ring atom in B which is adjacent to shared atom Z or which is adjacent to the ring atom that is adjacent to Z, and is:

(1)

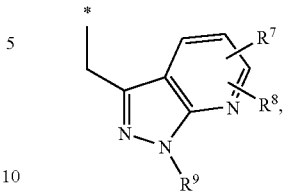

wherein each ring N is optionally an N-oxide,
- (2) *—$CH_2C(O)N(R^A)$-AryB,
- (3) *—$CH_2C(O)N(R^A)$-HetB,
- (4) *—$CH_2C(O)N(R^A)$—$C_{1-3}$ alkylene-AryB,
- (5) *—$CH_2C(O)N(R^A)$—$C_{1-3}$ alkylene-HetB,
- (6) *—$CH_2C(O)O$—$C_{1-3}$ alkylene-AryB,
- (7) *—$CH_2C(O)O$—$C_{1-3}$ alkylene-HetB,
- (8) *—$CH_2$-HetB,
- (9) *—$CH_2C(O)$-HetB,
- (10) *—$CH_2C(O)$-HetC, or
- (11) *—$CH_2CH_2OH$;

wherein the asterisk denotes the point of attachment to the rest of the compound;

$R^7$ and $R^8$ are each independently selected from the group consisting of:
- (1) H,
- (2) OH,
- (3) halogen,
- (4) CN,
- (5) $NO_2$,
- (6) $C_{1-6}$ alkyl,
- (7) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
- (8) O—$C_{1-6}$ alkyl,
- (9) O—$C_{1-6}$ alkyl in which the alkyl is substituted with O—$C_{1-6}$ alkyl, $N(R^A)R^B$, $C(O)N(R^A)R^B$, $C(O)R^A$, or $CO_2R^A$,
- (10) $C_{1-6}$ haloalkyl,
- (11) O—$C_{1-6}$ haloalkyl,
- (12) $N(R^C)R^D$,
- (13) $N(R^A)$—$C_{1-6}$ alkylene-$N(R^C)R^D$,
- (14) $C(O)N(R^A)R^B$,
- (15) $C(O)R^A$,
- (16) C(O)—$C_{1-6}$ haloalkyl,
- (17) $C(O)OR^A$,
- (18) $SR^A$,
- (19) $S(O)R^A$,
- (20) $S(O)_2R^A$,
- (21) $S(O)_2N(R^A)R^B$,
- (22) CycE,
- (23) O-CycE,
- (24) C(O)O-CycE,
- (25) $C(O)N(R^A)$-CycE,
- (26) $N(R^A)$-CycE,
- (27) $C_{1-6}$ alkyl substituted with CycE,
- (28) O—$C_{1-6}$ alkyl substituted with $N(R^A)$-CycE,
- (29) O—$C_{1-6}$ alkyl substituted with C(O)-CycE,
- (30) HetE,

(31) $N(R^A)S(O)_2R^B$,
(32) $N(R^A)C(O)R^B$, and
(33) $N(R^A)C(O)N(R^A)R^B$;

$R^9$ is H or $C_{1-6}$ alkyl;

each $R^A$ is independently H, $C_{1-6}$ alkyl, or $C_{1-6}$ haloalkyl;

each $R^B$ is independently H, $C_{1-6}$ alkyl, or $C_{1-6}$ haloalkyl;

each $R^C$ is independently H, $C_{1-6}$ alkyl, or $C_{1-6}$ haloalkyl;

each $R^D$ is independently H, $C_{1-6}$ alkyl, or $C_{1-6}$ haloalkyl;

alternatively and independently each pair of $R^C$ and $R^D$ together with the N atom to which they are both attached form a 4- to 7-membered, saturated or mono-unsaturated monocyclic ring optionally containing 1 heteroatom in addition to the nitrogen attached to $R^C$ and $R^D$ selected from N, O, and S, where the S is optionally oxidized to S(O) or $S(O)_2$; wherein the monocyclic ring is optionally substituted with 1 or 2 substituents each of which is independently: (1) $C_{1-6}$ alkyl, (2) $C_{1-6}$ fluoroalkyl, (3) $(CH_2)_{1-2}G$ wherein G is OH, O—$C_{1-6}$ alkyl, O—$C_{1-6}$ fluoroalkyl, $N(R^A)R^B$, $C(O)N(R^A)R^B$, $C(O)R^A$, $CO_2R^A$, or $SO_2R^A$, (4) O—$C_{1-16}$ alkyl, (5) O—$C_{1-6}$ fluoroalkyl, (6) OH, (7) oxo, (8) halogen, (9) $C(O)N(R^A)R^B$, (10) $C(O)R^A$, (11) C(O)—$C_{1-6}$ fluoroalkyl, (12) $C(O)OR^A$, or (13) $S(O)_2R^A$;

AryA is aryl optionally substituted with a total of from 1 to 6 substituents, wherein:
(i) from zero to 6 substituents are each independently:
  (1) $C_{1-6}$ alkyl,
  (2) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
  (3) O—$C_{1-16}$ alkyl,
  (4) O—$C_{1-6}$ alkyl, in which the alkyl is substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
  (5) $C_{1-6}$ haloalkyl,
  (6) O—$C_{1-6}$ haloalkyl,
  (7) OH,
  (8) halogen,
  (9) CN,
  (10) $NO_2$,
  (11) $N(R^A)R^B$,
  (12) $C(O)N(R^A)R^B$,
  (13) $C(O)R^A$,
  (14) C(O)—$C_{1-6}$ haloalkyl,
  (15) $C(O)OR^A$,
  (16) $OC(O)N(R^A)R^B$,
  (17) $SR^A$,
  (18) $S(O)R^A$,
  (19) $S(O)_2R^A$,
  (20) $S(O)_2N(R^A)R^B$,
  (21) $N(R^A)S(O)_2R^B$,
  (22) $N(R^A)S(O)_2N(R^A)R^B$,
  (23) $N(R^A)C(O)R^B$,
  (24) $N(R^A)C(O)N(R^A)R^B$,
  (25) $N(R^A)C(O)$—$C(O)N(R^A)R^B$,
  (26) $N(R^A)CO_2R^B$,
  (27) $C_{2-6}$ alkenyl substituted with CN, $NO_2$, $N(R^A)R^B$, or $C(O)N(R^A)R^B$, or
  (28) $C_{2-6}$ alkynyl substituted with CN, $NO_2$, $N(R^A)R^B$, or $C(O)N(R^A)R^B$, and
(ii) from zero to 2 substituents are each independently:
  (1) CycE,
  (2) AryE,
  (3) O-AryE,
  (4) HetE,
  (5) HetF,
  (6) $C_{1-6}$ alkyl substituted with CycE, AryE, O-AryE, HetE, or HetF,
  (7) $C_{2-6}$ alkenyl substituted with AryE,
  (8) $C_{2-6}$ alkynyl substituted with AryE, or
  (9) $C_{2-6}$ alkynyl substituted with HetE;

HetA is heteroaryl which is optionally substituted with a total of from 1 to 6 substituents, wherein:
(i) from zero to 6 substituents are each independently:
  (1) $C_{1-6}$ alkyl,
  (2) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
  (3) O—$C_{1-6}$ alkyl,
  (4) O—$C_{1-6}$ alkyl, in which the alkyl is substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
  (5) $C_{1-6}$ haloalkyl,
  (6) O—$C_{1-6}$ haloalkyl,
  (7) OH,
  (8) oxo,
  (9) halogen,
  (10) CN,
  (11) $NO_2$,
  (12) $N(R^A)R^B$,
  (13) $C(O)N(R^A)R^B$,
  (14) $C(O)R^A$,
  (15) C(O)—$C_{1-6}$ haloalkyl,
  (16) $C(O)OR^A$,
  (17) $OC(O)N(R^A)R^B$,
  (18) $SR^A$,
  (19) $S(O)R^A$,
  (20) $S(O)_2R^A$,
  (21) $S(O)_2N(R^A)R^B$,
  (22) $N(R^A)S(O)_2R^B$,
  (23) $N(R^A)S(O)_2N(R^A)R^B$,
  (24) $N(R^A)C(O)R^B$,
  (25) $N(R^A)C(O)N(R^A)R^B$,
  (26) $N(R^A)C(O)$—$C(O)N(R^A)R^B$, or
  (27) $N(R^A)CO_2R^B$, and
(ii) from zero to 2 substituents are each independently:
  (1) CycE,
  (2) AryE,
  (3) O-AryE,
  (4) HetE,
  (5) HetF, or
  (6) $C_{1-6}$ alkyl substituted with CycE, AryE, O-AryE, HetE, or HetF;

aryl is (i) phenyl, (ii) a 9- or 10-membered bicyclic, fused carbocylic ring system in which at least one ring is aromatic, or (iii) an 11- to 14-membered tricyclic, fused carbocyclic ring system in which at least one ring is aromatic;

heteroaryl is (i) a 5- or 6-membered heteroaromatic ring containing from 1 to 4 heteroatoms independently selected from N, O and S, wherein each N is optionally in the form of an oxide, (ii) a 9- or 10-membered bicyclic fused ring system, or (iii) an 11- to 16-membered tricyclic fused ring system, wherein the fused ring system of (ii) or (iii) contains from 1 to 6 heteroatoms independently selected from N, O and S, wherein each ring in the fused ring system contains zero, one or more than one heteroatom, at least one ring is aromatic, each N is optionally in the form of an oxide, and each S in a ring which is not aromatic is optionally $S(O)$ or $S(O)_2$;

AryB independently has the same definition as AryE;

HetB independently has the same definition as HetE;

HetC independently has the same definition as HetF;

each CycE is independently $C_{3-8}$ cycloalkyl which is optionally substituted with from 1 to 4 substituents each of which is independently halogen, $C_{1-6}$ alkyl, OH, O—$C_{1-6}$ alkyl, $C_{1-6}$ haloalkyl, or O—$C_{1-6}$ haloalkyl;

each AryE is independently phenyl or naphthyl, wherein the phenyl or naphthyl is optionally substituted with from 1 to 5 substituents each of which is independently halogen, CN, $NO_2$, $C_{1-6}$ alkyl, $C_{1-6}$ haloalkyl, OH, O—$C_{1-6}$ alkyl, O—$C_{1-6}$ haloalkyl, $C(O)N(R^A)R^B$, $C(O)R^A$, $CO_2R^A$, $SR^A$, $S(O)R^A$, $SO_2R^A$, $SO_2N(R^A)R^B$, or $SO_2N(R^A)C(O)R^B$;

each HetE is independently a 5- or 6-membered heteroaromatic ring containing from 1 to 4 heteroatoms independently selected from N, O and S, wherein each N is optionally in the form of an oxide, and wherein the heteroaromatic ring is optionally substituted with from 1 to 4 substituents each of which is independently halogen, CN, $NO_2$, $C_{1-6}$ alkyl, $C_{1-6}$ haloalkyl, O—$C_{1-6}$ alkyl, O—$C_{1-6}$ haloalkyl, OH, $N(R^A)R^B$, $N(R^A)C(O)N(R^A)R^B$, $N(R^A)CO_2R^B$, $C(O)N(R^A)R^B$, $C(O)R^A$, $CO_2R^A$, $SO_2R^A$, $SO_2N(R^A)R^B$, or phenyl, with the proviso that no more than 1 of the optional substituents is phenyl; and each HetF is independently a 4- to 7-membered, saturated or mono-unsaturated heterocyclic ring containing at least one carbon atom and from 1 to 4 heteroatoms independently selected from N, O and S, where each S is optionally oxidized to $S(O)$ or $S(O)_2$, and wherein the saturated or mono-unsaturated heterocyclic ring is optionally substituted with a total of from 1 to 4 substituents, each of which is independently halogen, CN, $C_{1-6}$ alkyl, OH, oxo, O—$C_{1-6}$ alkyl, $C_{1-6}$ haloalkyl, O—$C_{1-6}$ haloalkyl, $C(O)N(R^A)R^B$, $C(O)R^A$, $CO_2R^A$, $SO_2R^A$, or $SO_2N(R^A)R^B$.

Other embodiments, aspects and features of the present invention are either further described in or will be apparent from the ensuing description, examples and appended claims.

DETAILED DESCRIPTION OF THE INVENTION

The compounds of Formula I above, and pharmaceutically acceptable salts thereof, are HIV reverse transcriptase inhibitors. The compounds are useful for inhibiting HIV reverse transcriptase and for inhibiting HIV replication in vitro and in vivo. More particularly, the compounds of Formula I inhibit the polymerase function of HIV-1 reverse transcriptase. Based upon the testing of representative compounds of the invention in the assays set forth in Example 31 below, it is known that compounds of Formula I inhibit the RNA-dependent DNA polymerase activity of HIV-1 reverse transcriptase.

Representative compounds of the present invention also exhibit activity against drug resistant forms of HIV (e.g., mutant strains of HIV-1 in which reverse transcriptase has a mutation at lysine 103→asparagine (K103N) and/or tyrosine 181→cysteine (Y181C)), and thus can exhibit decreased cross-resistance against currently approved antiviral therapies.

A first embodiment of the present invention (alternatively referred to herein as "Embodiment E1") is a compound of Formula I (alternatively and more simply referred to as "Compound I") as originally defined (i.e., as defined in the Summary of the Invention above), or a pharmaceutically acceptable salt thereof; and provided that:

(A) when ring B is

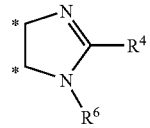

and $R^4$ is other than H, then $R^6$ is not

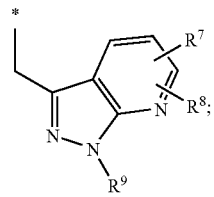

and
(B) when ring B is

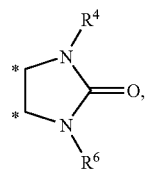

then $R^6$ is not

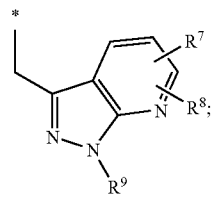

wherein the asterisks on ring B denote the points of attachment to ring A.

A second embodiment of the present invention (Embodiment E2) is a compound of Formula I, or a pharmaceutically acceptable salt thereof, wherein:

V is $C(R^{10})$, $N(R^{11})$, N or N oxide; W is $C(R^3)$, $N(R^{12})$, N or N oxide; Y is C or N; and Z is C or N, with the proviso that no more than two of V, W, Y and Z contain N;

R⁶ is attached to the ring atom in B which is adjacent to shared atom Z and is

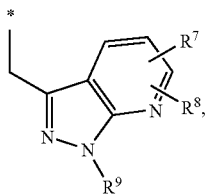

wherein each ring N is optionally an N-oxide, and wherein the asterisk denotes the point of attachment to the rest of the compound;

R⁷ and R⁸ are each independently selected from the group consisting of substituents (1) to (30) as originally defined above (i.e., the following substituents are excluded from the group: (31) N(R^A)S(O)₂R^B, (32) N(R^A)C(O)R^B, and (33) N(R^A)C(O)N(R^A)R^B).

each HetE is independently a 5- or 6-membered heteroaromatic ring containing from 1 to 4 heteroatoms independently selected from N, O and S, wherein each N is optionally in the form of an oxide, and wherein the heteroaromatic ring is optionally substituted with from 1 to 4 substituents each of which is independently halogen, C₁₋₆ alkyl, C₁₋₆ haloalkyl, O—C₁₋₆ alkyl, O—C₁₋₆ haloalkyl, OH, N(R^A)R^B, N(R^A)C(O)N(R^A)R^B, or N(R^A)CO₂R^B;

each HetF is independently a 4- to 7-membered, saturated or mono-unsaturated heterocyclic ring containing at least one carbon atom and from 1 to 4 heteroatoms independently selected from N, O and S, where each S is optionally oxidized to S(O) or S(O)₂, and wherein the saturated or mono-unsaturated heterocyclic ring is optionally substituted with a total of from 1 to 4 substituents, each of which is independently halogen, CN, C₁₋₆ alkyl, OH, oxo, O—C₁₋₆ alkyl, C₁₋₆ haloalkyl, or O—C₁₋₆ haloalkyl;

and all other variables are as originally defined.

A third embodiment of the present invention (Embodiment E3) is a compound of Formula I as defined in Embodiment E2, or a pharmaceutically acceptable salt thereof; and provided that:

(A) when ring B is

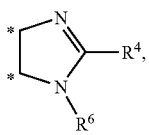

then R⁴ is H; and
(B) ring B is not

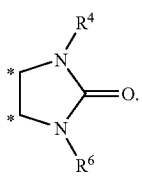

A fourth embodiment of the present invention (Embodiment E4) is a compound of Formula I, or a pharmaceutically acceptable salt thereof, wherein X is O; and all other variables are as originally defined or as defined in any one of Embodiments E1, E2, and E3.

A fifth embodiment of the present invention (Embodiment E5) is a compound of Formula I, or a pharmaceutically acceptable salt thereof, wherein V is C(R¹⁰); W is C(R³); Y is C; Z is C; ring A is aromatic (i.e., benzo); and all other variables are as originally defined or as defined in any one of Embodiments E1, E2, E3 and E4. Embodiment E5 corresponds to a compound of Formula II:

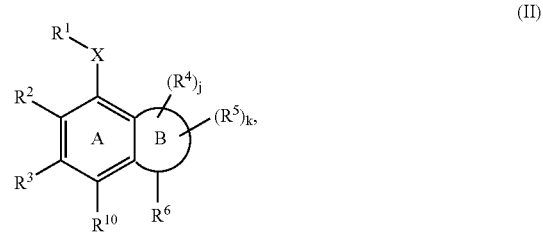

wherein the variables are as originally defined or as defined in any one of Embodiments E1, E2, E3 and E4.

A sixth embodiment of the present invention (Embodiment E6) is a compound of Formula I, or a pharmaceutically acceptable salt thereof, wherein V is N; W is C(R³); Y is C; Z is C; ring A is aromatic (i.e., pyrido); and all other variables are as originally defined or as defined in any one of Embodiments E1, E2, E3 and E4. Embodiment E6 corresponds to a compound of Formula III:

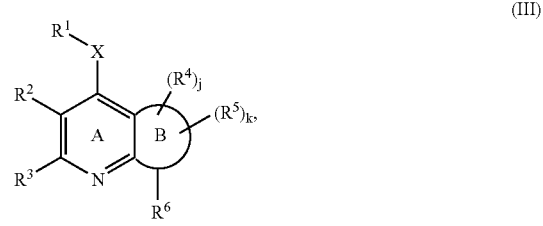

wherein the variables are as originally defined or as defined in any one of Embodiments E1, E2, E3 and E4.

A seventh embodiment of the present invention (Embodiment E7) is a compound of Formula I, or a pharmaceutically acceptable salt thereof, wherein V is C(R¹⁰); W is C(R³); Y is C; Z is N; and all other variables are as originally defined or as defined in any one of Embodiments E1, E2, E3 and E4. Embodiment E7 corresponds to a compound of Formula IV:

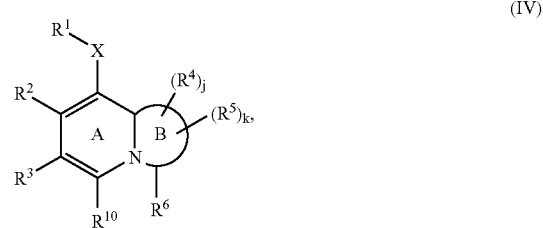

wherein the variables are as originally defined or as defined in any one of Embodiments E1, E2, E3 and E4. It is noted that since Y is C, Y is part of a double bond in ring B.

An eighth embodiment of the present invention (Embodiment E8) is a compound of Formula I, or a pharmaceutically acceptable salt thereof, wherein V is $C(R^{10})$; W is $C(R^3)$; Y is N; Z is C; and all other variables are as originally defined or as defined in any one of Embodiments E1, E2, E3 and E4. Embodiment E8 corresponds to a compound of Formula V:

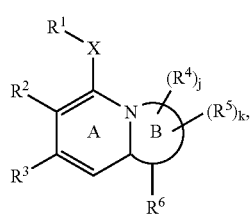

(V)

wherein the variables are as originally defined or as defined in any one of Embodiments E1, E2, E3 and E4. It is noted that since Z is C, Z is part of a double bond in ring B.

A ninth embodiment of the present invention (Embodiment E9) is a compound of Formula I, or a pharmaceutically acceptable salt thereof, wherein V is $C(R^{10})$; W is N; Y is C; Z is C; ring A is aromatic (i.e., pyrido); and all other variables are as originally defined or as defined in any one of Embodiments E1, E2, E3 and E4. Embodiment E9 corresponds to a compound of Formula VI:

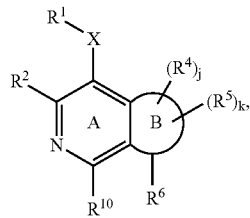

(VI)

wherein the variables are as originally defined or as defined in any one of Embodiments E1, E2, E3 and E4.

A tenth embodiment of the present invention (Embodiment E10) is a compound of Formula I, or a pharmaceutically acceptable salt thereof, wherein V is $C(R^{10})$; W is $C(R^3)$; Y is C; Z is C; ring A has two carbon-carbon double bonds; and all other variables are as originally defined or as defined in any one of Embodiments E1, E2, E3 and E4. Embodiment E10 corresponds to a compound of Formula VII:

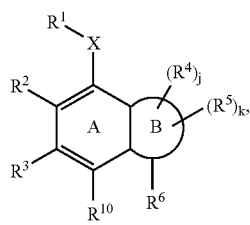

(VII)

wherein the variables are as originally defined or as defined in any one of Embodiments E1, E2, E3 and E4. It is noted that since Y is C and Z is C, Y and Z are parts of double bonds in ring B.

An eleventh embodiment of the present invention (Embodiment E11) is a compound of Formula I, or a pharmaceutically acceptable salt thereof, wherein $R^1$ is AryA; and all other variables are as originally defined or as defined in any one of the foregoing embodiments.

A twelfth embodiment of the present invention (Embodiment E12) is a compound of Formula I, or a pharmaceutically acceptable salt thereof, wherein $R^2$, $R^3$ and $R^{10}$ are each independently selected from the group consisting of:
(1) H,
(2) halogen,
(3) $N(R^A)R^B$,
(4) $C_{1-6}$ alkyl,
(5) $C_{1-6}$ fluoroalkyl,
(6) O—$C_{1-6}$ alkyl, and
(7) O—$C_{1-6}$ fluoroalkyl;

and all other variables are as originally defined or as defined in any one of the foregoing embodiments.

A thirteenth embodiment of the present invention (Embodiment E13) is a compound of Formula I, or a pharmaceutically acceptable salt thereof, wherein $R^2$ and $R^3$ are each independently selected from the group consisting of:
(1) H,
(2) halogen,
(3) $N(R^A)R^B$,
(4) $C_{1-4}$ alkyl,
(5) $CF_3$,
(6) O—$C_{1-4}$ alkyl, and
(7) $OCF_3$;

$R^{10}$ is H; and all other variables are as originally defined or as defined in any one of the foregoing embodiments.

A fourteenth embodiment of the present invention (Embodiment E14) is a compound of Formula I, or a pharmaceutically acceptable salt thereof, wherein $R^2$ and $R^3$ are each independently selected from the group consisting of H, Cl, Br, F and $C_{1-4}$ alkyl; $R^{10}$ is H; and all other variables are as originally defined or as defined in any one of the foregoing embodiments.

A fifteenth embodiment of the present invention (Embodiment E15) is a compound of Formula I, or a pharmaceutically acceptable salt thereof, wherein $R^2$ and $R^3$ are each independently selected from the group consisting of H, Cl, Br, F and $CH_3$; $R^{10}$ is H; and all other variables are as originally defined or as defined in any one of the foregoing embodiments.

A sixteenth embodiment of the present invention (Embodiment E16) is a compound of Formula I, or a pharmaceutically acceptable salt thereof, wherein $R^2$ is Br or Cl; $R^3$ is H; $R^{10}$ is H; and all other variables are as originally defined or as defined in any one of the foregoing embodiments. In an aspect of Embodiment E16 $R^2$ is Cl; $R^3$ is H; and $R^{10}$ is H.

A seventeenth embodiment of the present invention (Embodiment E17) is a compound of Formula I, or a pharmaceutically acceptable salt thereof, wherein $R^{11}$ and $R^{12}$ are each independently H or $C_{1-6}$ alkyl; and all other variables are as originally defined or as defined in any one of the foregoing embodiments.

An eighteenth embodiment of the present invention (Embodiment E18) is a compound of Formula I, or a pharmaceutically acceptable salt thereof, wherein $R^{11}$ and $R^{12}$ are each independently H or $C_{1-4}$ alkyl; and all other variables are as originally defined or as defined in any one of the foregoing embodiments.

A nineteenth embodiment of the present invention (Embodiment E19) is a compound of Formula I, or a pharmaceutically acceptable salt thereof, wherein $R^{11}$ and $R^{12}$ are each independently H or $CH_3$; and all other variables are as originally defined or as defined in any one of the foregoing embodiments.

A twentieth embodiment of the present invention (Embodiment E20) is a compound of Formula I, or a pharmaceutically acceptable salt thereof, wherein $R^{11}$ and $R^{12}$ are both H; and all other variables are as originally defined or as defined in any one of the foregoing embodiments.

A twenty-first embodiment of the present invention (Embodiment E21) is a compound of Formula I, or a pharmaceutically acceptable salt thereof, wherein $R^4$ and $R^5$ are each independently selected from the group consisting of:
(1) H,
(2) $C_{1-6}$ alkyl,
(3) O—$C_{1-6}$ alkyl,
(4) $C_{1-6}$ fluoroalkyl,
(5) O—$C_{1-6}$ fluoroalkyl, and
(6) halogen;

and all other variables are as originally defined or as defined in any one of the foregoing embodiments.

A twenty-second embodiment of the present invention (Embodiment E22) is a compound of Formula I, or a pharmaceutically acceptable salt thereof, wherein $R^4$ and $R^5$ are each independently selected from the group consisting of:
(1) H,
(2) $C_{1-4}$ alkyl,
(3) O—$C_{1-4}$ alkyl,
(4) $CF_3$,
(5) $OCF_3$, and
(6) halogen;

and all other variables are as originally defined or as defined in any one of the foregoing embodiments.

A twenty-third embodiment of the present invention (Embodiment E23) is a compound of Formula I, or a pharmaceutically acceptable salt thereof, wherein $R^4$ and $R^5$ are each independently selected from the group consisting of H, $C_{1-4}$ alkyl, Cl, Br and F; and all other variables are as originally defined or as defined in any one of the foregoing embodiments.

A twenty-fourth embodiment of the present invention (Embodiment E24) is a compound of Formula I, or a pharmaceutically acceptable salt thereof, wherein $R^4$ and $R^5$ are each independently selected from the group consisting of H, $CH_3$, $OCH_3$, $CF_3$, $OCF_3$, Cl, Br and F; and all other variables are as originally defined or as defined in any one of the foregoing embodiments.

A twenty-fifth embodiment of the present invention (Embodiment E25) is a compound of Formula I, or a pharmaceutically acceptable salt thereof, wherein $R^4$ and $R^5$ are both H; and all other variables are as originally defined or as defined in any one of the foregoing embodiments.

A twenty-sixth embodiment of the present invention (Embodiment E26) is a compound of Formula I, or a pharmaceutically acceptable salt thereof, wherein $R^7$ and $R^8$ are each independently selected from the group consisting of:
(1) H,
(2) OH,
(3) halogen,
(4) CN,
(5) $NO_2$,
(6) $C_{1-6}$ alkyl,
(7) O—$C_{1-6}$ alkyl,
(8) $O(CH_2)_{2-3}N(R^A)R^B$,
(9) $O(CH_2)_{1-3}C(O)R^A$,
(10) $C_{1-6}$ fluoroalkyl,
(11) O—$C_{1-6}$ fluoroalkyl,
(12) $N(R^C)R^D$,
(13) $N(R^A)$—$(CH_2)_{2-3}$—$N(R^C)R^D$,
(14) $C(O)N(R^A)R^B$,
(15) $C(O)R^A$,
(16) $C(O)OR^A$,
(17) $SR^A$,
(18) $S(O)R^A$,
(19) $S(O)_2R^A$, and
(20) $S(O)_2N(R^A)R^B$;

and all other variables are as originally defined or as defined in any one of the foregoing embodiments.

A twenty-seventh embodiment of the present invention (Embodiment E27) is a compound of Formula I, or a pharmaceutically acceptable salt thereof, wherein $R^7$ and $R^8$ are each independently selected from the group consisting of:
(1) H,
(2) OH,
(3) halogen,
(4) CN,
(5) $NO_2$,
(6) $C_{1-4}$ alkyl,
(7) O—$C_{1-4}$ alkyl,
(8) $O(CH_2)_{2-3}N(R^A)R^B$,
(9) $O(CH_2)_{1-3}C(O)R^A$,
(10) $CF_3$,
(11) $OCF_3$,
(12) $O(CH_2)_{1-2}CF_3$,
(12) $N(R^C)R^D$,
(13) $N(R^A)$—$(CH_2)_{2-3}$—$N(R^C)R^D$, and
(14) $C(O)N(R^A)R^B$;

and all other variables are as originally defined or as defined in any one of the foregoing embodiments.

A twenty-eighth embodiment of the present invention (Embodiment E28) is a compound of Formula I, or a pharmaceutically acceptable salt thereof, wherein $R^7$ is H; $R^8$ is H, OH, Cl, Br, F, $CH_3$, $OCH_3$, $O(CH_2)_{2-3}NH_2$, $CF_3$, $OCF_3$, $OCH_2CF_3$, $NH_2$, $N(H)CH_3$, $N(CH_3)_2$, $C(O)NH_2$, $C(O)N(H)CH_3$, or $C(O)N(CH_3)_2$; and all other variables are as originally defined or as defined in any one of the foregoing embodiments.

A twenty-ninth embodiment of the present invention (Embodiment E29) is a compound of Formula I, or a pharmaceutically acceptable salt thereof, wherein $R^7$ is H; $R^8$ is H or $NH_2$; and all other variables are as originally defined or as defined in any one of the foregoing embodiments.

A thirtieth embodiment of the present invention (Embodiment E30) is a compound of Formula I, or a pharmaceutically acceptable salt thereof, wherein:

$R^6$ is

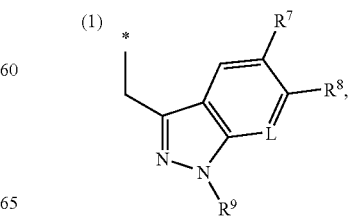

(2) 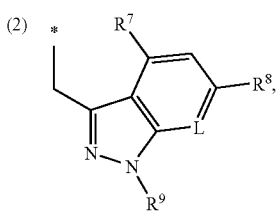

(3) *—CH$_2$C(O)N(R$^A$)-AryB, (4) *—CH$_2$C(O)N(R$^A$)-HetB, (5) *—CH$_2$C(O)N(R$^A$)—C$_{1-3}$ alkylene-AryB, (6) *—CH$_2$C(O)N(R$^A$)—C$_{1-3}$ alkylene-HetB, (7) *—CH$_2$C(O)O—C$_{1-3}$ alkylene-AryB, (8) *—CH$_2$-HetB, (9) *—CH$_2$C(O)-HetB, (10) *—CH$_2$C(O)-HetC, or (11) *—CH$_2$CH$_2$OH;

L is N or N oxide; and all other variables are as originally defined or as defined in any one of the foregoing embodiments.

A thirty-first embodiment of the present invention (Embodiment E31) is a compound of Formula I, or a pharmaceutically acceptable salt thereof, wherein R$^6$ is:

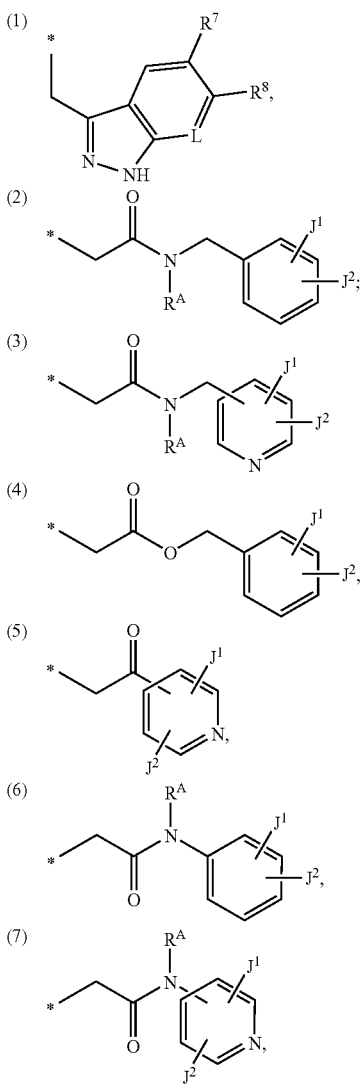

or

(10) *—CH$_2$CH$_2$OH;

J$^1$ and J$^2$ are each independently H, halogen, CN, NO$_2$, C$_{1-4}$ alkyl, CF$_3$, OH, O—C$_{1-4}$ alkyl, OCF$_3$, C(O)N(R$^A$)R$^B$, C(O)R$^A$, CO$_2$R$^A$, SO$_2$R$^A$, or SO$_2$N(R$^A$)R$^B$;

J$^3$ is H, halogen, CN, C$_{1-4}$ alkyl, OH, oxo, O—C$_{1-4}$ alkyl, CF$_3$, OCF$_3$, C(O)NH$_2$, C(O)N(H)CH$_3$, C(O)N(R$^A$)R$^B$, C(O)R$^A$, CO$_2$R$^A$, SO$_2$R$^A$, or SO$_2$N(R$^A$)R$^B$;

L is N or N oxide; and all other variables are as originally defined or as defined in any one of the foregoing embodiments.

In an aspect of Embodiment E31, J$^1$ and J$^2$ are each independently H, Cl, Br, F, CN, NO$_2$, C$_{1-3}$ alkyl, CF$_3$, OH, O—C$_{1-3}$ alkyl, OCF$_3$, C(O)NH$_2$, C(O)N(H)CH$_3$, C(O)N(CH$_3$)$_2$, C(O)H, C(O)CH$_3$, CO$_2$H, CO$_2$CH$_3$, SO$_2$CH$_3$, or SO$_2$NH$_2$; and J$^3$ is H, Cl, Br, F, CN, C$_{1-3}$ alkyl, OH, oxo, O—C$_{1-3}$ alkyl, CF$_3$, OCF$_3$, C(O)NH$_2$, C(O)N(H)CH$_3$, C(O)N(CH$_3$)$_2$, C(O)H, C(O)CH$_3$, CO$_2$H, CO$_2$CH$_3$, SO$_2$CH$_3$, or SO$_2$NH$_2$.

A thirty-second embodiment of the present invention (Embodiment E32) is a compound of Formula I, or a pharmaceutically acceptable salt thereof, wherein R$^6$ is:

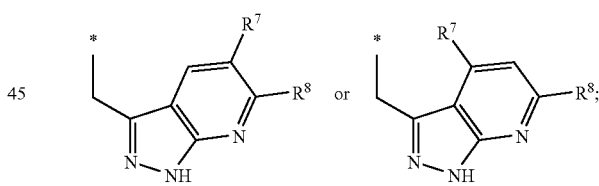

and all other variables are as originally defined or as defined in any one of the foregoing embodiments.

A thirty-third embodiment of the present invention (Embodiment E33) is a compound of Formula I, or a pharmaceutically acceptable salt thereof, wherein R$^6$ is:

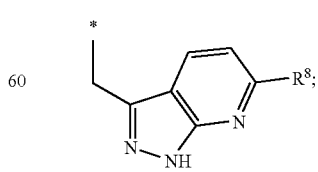

and all other variables are as originally defined or as defined in any one of the foregoing embodiments.

To the extent any of the preceding or subsequent embodiments refer back to and are incorporated into Embodiments E2 and E4 respectively, the provisos set forth therein apply. It is understood, however, that the definitions of variables in the provisos set forth in Embodiments E2 and E4 can be customized to reflect the definitions of variables in the embodiments being incorporated therein. For example, the provisos set forth in Embodiments E2 and E4 can be customized to reflect the definition of $R^6$ in Embodiments E30 to E33. As a particular example, when Embodiment E30 is incorporated into Embodiment E2, the proviso can be adjusted to read as follows— and provided that:

(A) when ring B is

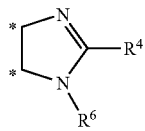

and $R^4$ is other than H, then $R^6$ is not

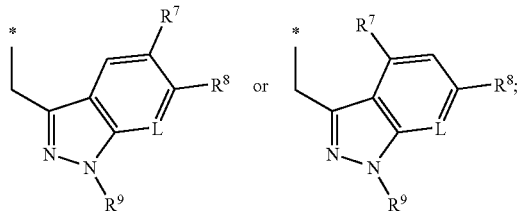

and (B) when ring B is

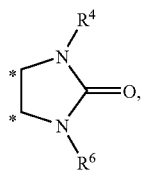

then $R^6$ is not

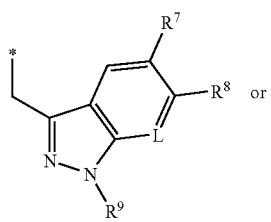

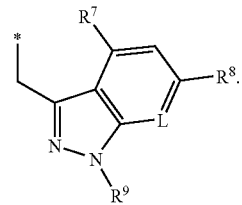

A thirty-fourth embodiment of the present invention (Embodiment E34) is a compound of Formula I, or a pharmaceutically acceptable salt thereof, wherein AryA is phenyl or naphthyl, wherein the phenyl is optionally substituted with from 1 to 3 substituents each of which is independently $C_{1-6}$ alkyl, O—$C_{1-6}$ alkyl, $CF_3$, $OCF_3$, OH, halogen, CN, $NO_2$, $N(R^A)R^B$, $C(O)N(R^A)R^B$, $C(O)R^A$, $C(O)CF_3$, $CO_2R^A$, $SO_2R^A$, CH=CH—$(CH_2)_{0-2}$CN, C≡C—$(CH_2)_{1-2}N(R^A)R^B$ or $C_{1-6}$ alkylene-$N(R^A)R^B$; and all other variables are as originally defined or as defined in any one of the foregoing embodiments. In an aspect of this embodiment, AryA is as originally defined in Embodiment E34, except that the list of optional substituents excludes C≡C—$(CH_2)_{1-2}N(R^A)R^B$.

A thirty-fifth embodiment of the present invention (Embodiment E35) is a compound of Formula I, or a pharmaceutically acceptable salt thereof, wherein AryA is:

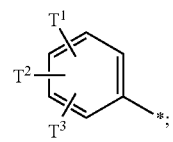

wherein $T^1$ and $T^2$ and $T^3$ are each independently H, $C_{1-4}$ alkyl, halogen, CN, CH=CH—CN, $C(O)R^A$, or $(CH_2)_{1-2}N(R^A)R^B$; and all other variables are as originally defined or as defined in any one of the foregoing embodiments.

A thirty-sixth embodiment of the present invention (Embodiment E36) is a compound of Formula I, or a pharmaceutically acceptable salt thereof, wherein AryA is:

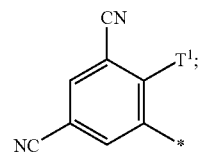

wherein $T^1$ is H or Cl; and all other variables are as originally defined or as defined in any one of the foregoing embodiments. In an aspect of this embodiment, $T^1$ is H.

A thirty-seventh embodiment of the present invention (Embodiment E37) is a compound of Formula I, or a pharmaceutically acceptable salt thereof, wherein AryA is:

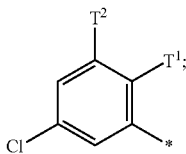

wherein T¹ is H or Cl; T² is CN, CH(O), CH$_2$NH$_2$, or CH$_2$N(H)CH$_3$; and all other variables are as originally defined or as defined in any one of the foregoing embodiments.

A thirty-eighth embodiment of the present invention (Embodiment E38) is a compound of Formula I, or a pharmaceutically acceptable salt thereof, wherein AryA is:

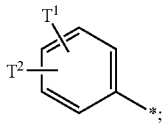

wherein T¹ and T² are each independently H, C$_{1-4}$ alkyl, halogen, CN, CH=CH—CN, or C≡C—CH$_2$N(R$^A$)R$^B$; and all other variables are as originally defined or as defined in any one of the foregoing embodiments. In an aspect of this embodiment, AryA is as originally defined in Embodiment 38, except that T¹ and T² are each independently H, C$_{1-4}$ alkyl, halogen, CN, or CH=CH—CN.

A thirty-ninth embodiment of the present invention (Embodiment E39) is a compound of Formula I, or a pharmaceutically acceptable salt thereof, wherein AryA is:

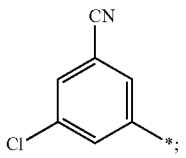

and all other variables are as originally defined or as defined in any one of the foregoing embodiments.

A fortieth embodiment of the present invention (Embodiment E40) is a compound of Formula I, or a pharmaceutically acceptable salt thereof, wherein HetA is a heteroaryl selected from the group consisting of thienyl, furanyl, pyrrolyl, imidazolyl, pyrazolyl, triazolyl, tetrazolyl, oxazolyl, isooxazolyl, thiazolyl, isothiazolyl, oxadiazolyl, thiadiazolyl, pyridinyl, pyrazinyl, pyrimidinyl, pyridazinyl, benzofuranyl, benzothienyl, indolyl, indazolyl, isobenzofuranyl, benzisoxazolyl, benzoxazolyl, benzimidazolyl, benzopiperidinyl, chromenyl, quinolinyl, isoquinolinyl, cinnolinyl, quinoxalinyl, quinazolinyl, and imidazopyridinyl, wherein the heteroaryl is optionally substituted with from 1 to 3 substituents each of which is independently C$_{1-4}$ alkyl, CF$_3$, O—C$_{1-4}$ alkyl, OCF$_3$, OH, halogen, CN, NO$_2$, N(R$^A$)R$^B$, C(O)N(R$^A$)R$^B$, C(O)R$^A$, C(O)CF$_3$, CO$_2$R$^A$, SO$_2$R$^A$, or SO$_2$N(R$^A$)R$^B$; and all other variables are as originally defined or as defined in any of the preceding embodiments. In an aspect of Embodiment E40, HetA is as originally defined in Embodiment E40, except that each of the optional 1 to 3 substituents is independently C$_{1-4}$ alkyl, CF$_3$, O—C$_{1-4}$ alkyl, OCF$_3$, OH, halogen, CN, NO$_2$, N(R$^A$)R$^B$, C(O)N(R$^A$)R$^B$, C(O)R$^A$, C(O)CF$_3$, CO$_2$R$^A$, or SO$_2$R$^A$.

A forty-first embodiment of the present invention (Embodiment E41) is a compound of Formula I, or a pharmaceutically acceptable salt thereof, wherein R$^A$ and R$^B$ are each independently H or C$_{1-6}$ alkyl; and all other variables are as originally defined or as defined in any of the preceding embodiments.

A forty-second embodiment of the present invention (Embodiment E42) is a compound of Formula I, or a pharmaceutically acceptable salt thereof, wherein R$^A$ and R$^B$ are each independently H or C$_{1-4}$ alkyl; and all other variables are as originally defined or as defined in any of the preceding embodiments.

A forty-third embodiment of the present invention (Embodiment E43) is a compound of Formula I, or a pharmaceutically acceptable salt thereof, wherein R$^A$ and R$^B$ are each independently H or CH$_3$; and all other variables are as originally defined or as defined in any of the preceding embodiments.

A forty-fourth embodiment of the present invention (Embodiment E44) is a compound of Formula I, or a pharmaceutically acceptable salt thereof, wherein R$^C$ and R$^D$ are each independently H or C$_{1-6}$ alkyl; or alternatively and independently each pair of R$^C$ and R$^D$ together with the N atom to which they are both attached form a 4- to 7-membered, saturated monocyclic ring optionally containing 1 heteroatom in addition to the nitrogen attached to R$^C$ and R$^D$ selected from N, O, and S, where the S is optionally oxidized to S(O) or S(O)$_2$; and wherein the monocyclic ring is optionally substituted with 1 or 2 substituents each of which is independently: (1) C$_{1-4}$ alkyl, (2) CF$_3$, (3) C(O)N(R$^A$)R$^B$, (4) C(O)R$^A$, (5) C(O)—CF$_3$, (6) C(O)OR$^A$, or (7) S(O)$_2$R$^A$; and all other variables are as originally defined or as defined in any of the preceding embodiments.

A forty-fifth embodiment of the present invention (Embodiment E45) is a compound of Formula I, or a pharmaceutically acceptable salt thereof, wherein R$^C$ and R$^D$ are each independently H or C$_{1-4}$ alkyl; or alternatively and independently each pair of R$^C$ and R$^D$ together with the N atom to which they are both attached form a saturated monocyclic ring selected from the group consisting of

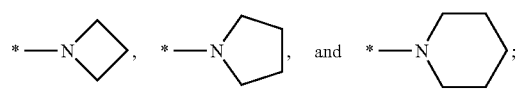

and all other variables are as originally defined or as defined in any of the preceding embodiments.

A forty-sixth embodiment of the present invention (Embodiment E46) is a compound of Formula I, or a pharmaceutically acceptable salt thereof, wherein R$^C$ and R$^D$ are each independently H or C$_{1-4}$ alkyl; and all other variables are as originally defined or as defined in any of the preceding embodiments.

A forty-seventh embodiment of the present invention (Embodiment E47) is a compound of Formula I, or a pharmaceutically acceptable salt thereof, wherein R$^C$ and R$^D$ are each independently H or CH$_3$; and all other variables are as originally defined or as defined in any of the preceding embodiments.

A forty-eighth embodiment of the present invention (Embodiment E48) is a compound of Formula I, or a pharmaceutically acceptable salt thereof, wherein $R^9$ is H or $C_{1-4}$ alkyl; and all other variables are as originally defined or as defined in any of the preceding embodiments.

A forty-ninth embodiment of the present invention (Embodiment E49) is a compound of Formula I, or a pharmaceutically acceptable salt thereof, wherein $R^9$ is H; and all other variables are as originally defined or as defined in any of the preceding embodiments.

A fiftieth embodiment of the present invention (Embodiment E50) is a compound of Formula I, or a pharmaceutically acceptable salt thereof, wherein each CycE is independently $C_{3-7}$ cycloalkyl which is optionally substituted with from 1 to 3 substituents each of which is independently Cl, Br, F, $C_{1-4}$ alkyl, OH, O—$C_{1-4}$ alkyl, $C_{1-4}$ fluoroalkyl, or O—$C_{1-4}$ fluoroalkyl; and all other variables are as originally defined or as defined in any of the preceding embodiments.

A fifty-first embodiment of the present invention (Embodiment E51) is a compound of Formula I, or a pharmaceutically acceptable salt thereof, wherein each AryE is independently phenyl which is optionally substituted with from 1 to 4 substituents each of which is independently Cl, Br, F, CN, $NO_2$, $C_{1-4}$ alkyl, $C_{1-4}$ fluoroalkyl, OH, O—$C_{1-4}$ alkyl, O—$C_{1-4}$ fluoroalkyl, $C(O)N(R^A)R^B$, $C(O)R^A$, $CO_2R^A$, $SR^A$, $S(O)R^A$, $SO_2R^A$, $SO_2N(R^A)R^B$, or $SO_2N(R^A)C(O)R^B$; and all other variables are as originally defined or as defined in any of the preceding embodiments.

A fifty-second embodiment of the present invention (Embodiment E52) is a compound of Formula I, or a pharmaceutically acceptable salt thereof, wherein each HetE is independently a 5- or 6-membered heteroaromatic ring containing from 1 to 4 heteroatoms independently selected from N, O and S, wherein each N is optionally in the form of an oxide, and wherein the heteroaromatic ring is optionally substituted with from 1 to 3 substituents each of which is independently Cl, Br, F, $C_{1-4}$ alkyl, $C_{1-4}$ fluoroalkyl, O—$C_{1-4}$ alkyl, O—$C_{1-4}$ fluoroalkyl, OH, $N(R^A)R^B$, $N(R^A)C(O)N(R^A)R^B$, or $N(R^A)CO_2R^B$; and all other variables are as originally defined or as defined in any of the preceding embodiments.

A fifty-third embodiment of the present invention (Embodiment E53) is a compound of Formula I, or a pharmaceutically acceptable salt thereof, wherein each HetF is independently a 4- to 7-membered, saturated or mono-unsaturated heterocyclic ring containing at least one carbon atom and from 1 to 3 heteroatoms independently selected from N, O and S, where each S is optionally oxidized to S(O) or $S(O)_2$, and wherein the saturated or mono-unsaturated heterocyclic ring is optionally substituted with a total of from 1 to 3 substituents, each of which is independently Cl, Br, F, CN, $C_{1-4}$ alkyl, OH, oxo, O—$C_{1-4}$ alkyl, $C_{1-4}$ fluoroalkyl, or O—$C_{1-4}$ fluoroalkyl; and all other variables are as originally defined or as defined in any of the preceding embodiments.

A fifty-fourth embodiment of the present invention (Embodiment E54) is a compound of Formula I, or a pharmaceutically acceptable salt thereof, wherein each AryB is independently phenyl which is optionally substituted with from 1 to 4 substituents each of which is independently Cl, Br, F, CN, $NO_2$, $C_{1-4}$ alkyl, $C_{1-4}$ fluoroalkyl, OH, O—$C_{1-4}$ alkyl, O—$C_{1-4}$ fluoroalkyl, $C(O)N(R^A)R^B$, $C(O)R^A$, $CO_2R^A$, $SR^A$, $S(O)R^A$, $SO_2R^A$, $SO_2N(R^A)R^B$, or $SO_2N(R^A)C(O)R^B$; and all other variables are as originally defined or as defined in any of the preceding embodiments.

A fifty-fifth embodiment of the present invention (Embodiment E55) is a compound of Formula I, or a pharmaceutically acceptable salt thereof, wherein AryB is phenyl which is optionally substituted with from 1 to 2 substituents each of which is independently Cl, Br, F, CN, $NO_2$, $C_{1-4}$ alkyl, $CF_3$, OH, O—$C_{1-4}$ alkyl, $OCF_3$, $C(O)N(R^A)R^B$, $C(O)R^A$, $CO_2R^A$, $SO_2R^A$, or $SO_2N(R^A)R^B$; and all other variables are as originally defined or as defined in any of the preceding embodiments.

A fifty-sixth embodiment of the present invention (Embodiment E56) is a compound of Formula I, or a pharmaceutically acceptable salt thereof, wherein HetB is independently a 5- or 6-membered heteroaromatic ring containing from 1 to 4 heteroatoms independently selected from N, O and S, wherein each N is optionally in the form of an oxide, and wherein the heteroaromatic ring is optionally substituted with from 1 to 3 substituents each of which is independently Cl, Br, F, CN, $NO_2$, $C_{1-4}$ alkyl, $CF_3$, OH, O—$C_{1-4}$ alkyl, $OCF_3$, $N(R^A)R^B$, $N(R^A)C(O)N(R^A)R^B$, $N(R^A)CO_2R^B$, $C(O)N(R^A)R^B$, $C(O)R^A$, $CO_2R^A$, $SO_2R^A$, $SO_2N(R^A)R^B$, or phenyl, with the proviso that no more than 1 of the optional substituents is phenyl; and all other variables are as originally defined or as defined in any of the preceding embodiments. In an aspect of this embodiment, HetB is as originally defined in Embodiment E56, except that the heteroaromatic ring is optionally substituted with from 1 to 3 substituents each of which is independently Cl, Br, F, $C_{1-4}$ alkyl, $C_{1-4}$ fluoroalkyl, O—$C_{1-4}$ alkyl, O—$C_{1-4}$ fluoroalkyl, OH, $N(R^A)R^B$, $N(R^A)C(O)N(R^A)R^B$, $N(R^A)CO_2R^B$, $SO_2N(R^A)R^B$, or phenyl, with the proviso that no more than 1 of the optional substituents is phenyl.

A fifty-seventh embodiment of the present invention (Embodiment E57) is a compound of Formula I, or a pharmaceutically acceptable salt thereof, wherein HetB is a heteroaromatic ring selected from the group consisting of pyrrolyl, pyrazolyl, oxazolyl, thiazolyl, imidazolyl, oxadiazolyl, pyridyl and pyrimidinyl, wherein the heteroaromatic ring is optionally substituted with from 1 to 2 substituents, each of which is independently Cl, Br, F, CN, $NO_2$, $C_{1-4}$ alkyl, $CF_3$, OH, O—$C_{1-4}$ alkyl, $OCF_3$, $C(O)N(R^A)R^B$, $C(O)R^A$, $CO_2R^A$, $SO_2R^A$, $SO_2N(R^A)R^B$, or phenyl, with the proviso that no more than 1 of the optional substituents is phenyl; and all other variables are as originally defined or as defined in any of the preceding embodiments. In an aspect of this embodiment, HetB is as originally defined in Embodiment E57, except that the heteroaromatic ring is optionally substituted with from 1 to 2 substituents, each of which is independently Cl, Br, F, $C_{1-4}$ alkyl, $CF_3$, O—$C_{1-4}$ alkyl, $OCF_3$, OH, $N(R^A)R^B$, or phenyl, with the proviso that no more than 1 of the optional substituents is phenyl.

A fifty-eighth embodiment of the present invention (Embodiment E58) is a compound of Formula I, or a pharmaceutically acceptable salt thereof, wherein HetC is independently a 4- to 7-membered, saturated or mono-unsaturated heterocyclic ring containing at least one carbon atom and from 1 to 3 heteroatoms independently selected from N, O and S, where each S is optionally oxidized to S(O) or $S(O)_2$, and wherein the saturated or mono-unsaturated heterocyclic ring is optionally substituted with a total of from 1 to 3 substituents, each of which is independently Cl, Br, F, CN, $C_{1-4}$ alkyl, OH, oxo, O—$C_{1-4}$ alkyl, $C_{1-4}$ fluoroalkyl, O—$C_{1-4}$ fluoroalkyl, $C(O)N(R^A)R^B$, $C(O)R^A$, $CO_2R^A$, $SO_2R^A$, or $SO_2N(R^A)R^B$; and all other variables are as originally defined or as defined in any of the preceding embodiments.

A fifty-ninth embodiment of the present invention (Embodiment E59) is a compound of Formula I, or a pharmaceutically acceptable salt thereof, wherein HetC is a saturated heterocyclic ring selected from the group consisting of 1-pyrrolidinyl, 1-piperidinyl, 4-morpholinyl, 4-thiomorpholinyl in which the S is optionally oxidized to S(O) or $S(O)_2$, and 1-piperazinyl, wherein the saturated heterocyclic ring is optionally substituted with from 1 to 2 substituents each of which is Cl, Br, F, CN, $C_{1-4}$ alkyl, OH, oxo, O—$C_{1-4}$ alkyl, $CF_3$, $OCF_3$, $C(O)NH_2$, $C(O)N(H)CH_3$, $C(O)N(CH_3)_2$, C(O)

CH₃, CO₂CH₃, SO₂CH₃, or SO₂NH₂; and all other variables are as originally defined or as defined in any of the preceding embodiments.

Additional embodiments of AryB, HetB, and HetC are incorporated into the definition of $R^6$ in Embodiment E31 above.

A first class of compounds of the present invention (alternatively referred to herein as Class C1) includes compounds, and pharmaceutically acceptable salts thereof, selected from compounds of Formula VIII:

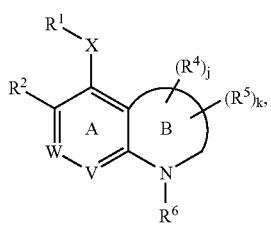
(VIII)

wherein all variables therein are as originally defined. A sub-class of Class Cl (i.e., Sub-class SC1-1) includes the compounds of Formula VIII in which X is O and pharmaceutically acceptable salts thereof. Other sub-classes of Class C1 include the compounds of Formula VIII and their pharmaceutically acceptable salts, wherein the variables are as respectively defined in the preceding embodiments.

A second class of compounds of the present invention (alternatively referred to herein as Class C2) includes compounds and pharmaceutically acceptable salts thereof, selected from compounds of Formula:

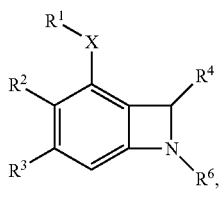
(IIa)

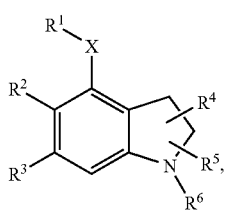
(IIb)

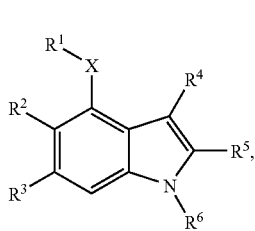
(IIc)

-continued

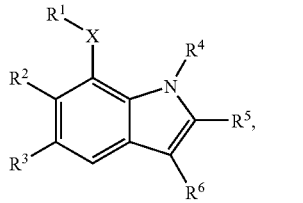
(IId)

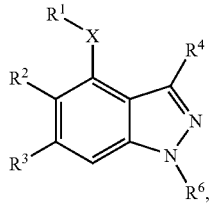
(IIe)

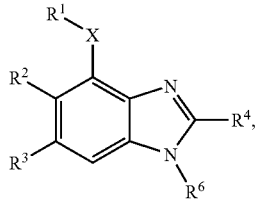
(IIf)

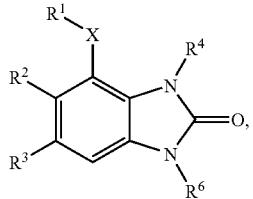
(IIg)

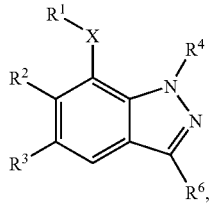
(IIh)

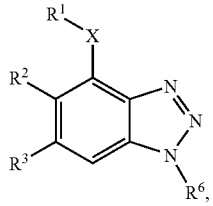
(IIi)

(IIj)

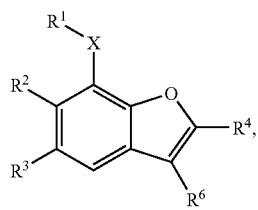 (IIk)
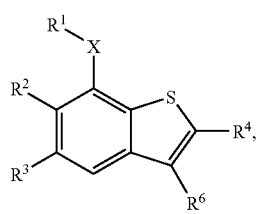 (IIl)
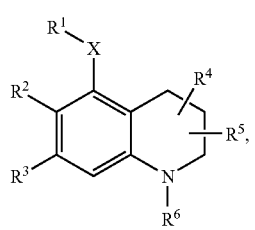 (IIm)
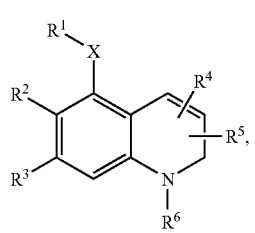 (IIn)
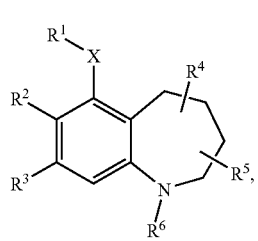 (IIo)
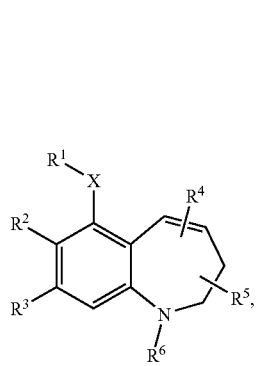 (IIp)
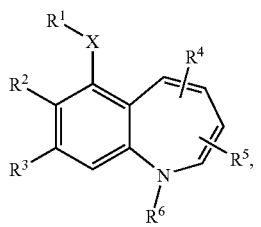 (IIq)
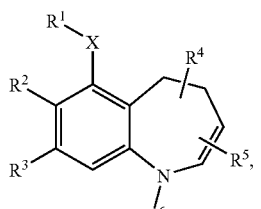 (IIr)
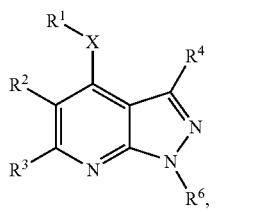 (IIIa)
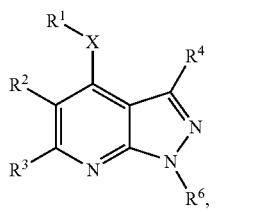 (IVa)
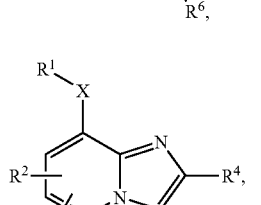 (IVb)
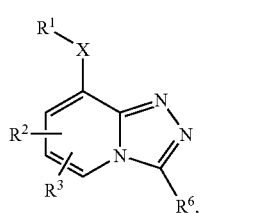 (IVc)
(Va)

-continued

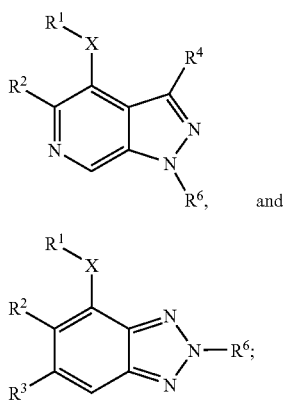

(VIa)

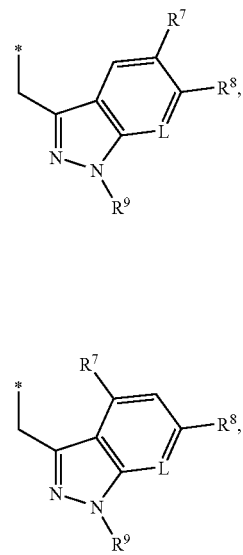

(VIIa)

wherein all variables therein are as originally defined. A sub-class of Class C2 (i.e., Sub-class SC2-1) includes the compounds in which X is O and pharmaceutically acceptable salts thereof. Other sub-classes of Class C2 include the compounds of Formulas IIa to VIIa and their pharmaceutically acceptable salts, wherein the variables are as respectively defined in the preceding embodiments.

A third class of compounds of the present invention (Class C3) is identical to Class C2 except that compounds of Formula IVc and Formula VIIa and their salts are excluded. A sub-class of Class C3 (i.e., Sub-class SC3-1) includes the compounds in which X is O and pharmaceutically acceptable salts thereof. Other sub-classes of Class C3 include the compounds of the various formulas (excluding IVc and VIIa) and their pharmaceutically acceptable salts, wherein the variables are as respectively defined in the preceding embodiments.

A fourth class of compounds of the present invention (Class C4) includes compounds of Formula IIe as shown in Class C3 and pharmaceutically acceptable salts thereof, wherein all variables therein are as originally defined. A sub-class of Class C4 (i.e., Sub-class SC4-1) includes the compounds of Formula IIe in which X is O and pharmaceutically acceptable salts thereof. Other sub-classes of Class C4 include the compounds of Formula IIe and their pharmaceutically acceptable salts, wherein the variables are as respectively defined in the preceding embodiments.

A fifth class of compounds of the present invention (Class C5) includes compounds of Formula IIi as shown in Class C3 and pharmaceutically acceptable salts thereof, wherein all variables therein are as originally defined. A sub-class of Class C5 (i.e., Sub-class SC5-1) includes the compounds of Formula IIi in which X is O and pharmaceutically acceptable salts thereof. Other sub-classes of Class C3 include the compounds of Formula IIi and their pharmaceutically acceptable salts, wherein the variables are as respectively defined in the preceding embodiments.

A sixth class of compounds of the present invention (Class C6) includes compounds of Formula I and pharmaceutically acceptable salts thereof, wherein:

X is O;

$R^1$ is AryA;

$R^2$, $R^3$ and $R^{10}$ are each independently selected from the group consisting of: (1) H, (2) halogen, (3) $N(R^A)R^B$, (4) $C_{1-6}$ alkyl, (5) $C_{1-6}$ fluoroalkyl, (6) O—$C_{1-6}$ alkyl, and (7) O—$C_{1-6}$ fluoroalkyl;

$R^{11}$ and $R^{12}$ are each independently H or $C_{1-6}$ alkyl;

$R^4$ and $R^5$ are each independently selected from the group consisting of: (1) H, (2) $C_{1-6}$ alkyl, (3) O—$C_{1-6}$ alkyl, (4) $C_{1-6}$ fluoroalkyl, (5) O—$C_{1-6}$ fluoroalkyl, and (6) halogen;

$R^6$ is: (1)

(2)

(3) *—$CH_2C(O)N(R^A)$-AryB, (4) *—$CH_2C(O)N(R^A)$-HetB, (5) *—$CH_2C(O)N(R^A)$—$C_{1-3}$ alkylene-AryB, (6) *—$CH_2C(O)N(R^A)$—$C_{1-3}$ alkylene-HetB, (7) *—$CH_2C(O)O$—$C_{1-3}$ alkylene-AryB, (8) *—$CH_2$-HetB, (9) *—$CH_2C(O)$-HetB, (10) *—$CH_2C(O)$-HetC, or (11) *—$CH_2CH_2OH$;

L is N or N oxide;

$R^7$ and $R^8$ are each independently selected from the group consisting of: (1) H, (2) OH, (3) halogen, (4) CN, (5) $NO_2$, (6) $C_{1-6}$ alkyl, (7) O—$C_{1-6}$ alkyl, (8) $O(CH_2)_{2-3}N(R^A)R^B$, (9) $O(CH_2)_{1-3}C(O)R^A$, (10) $C_{1-6}$ fluoroalkyl, (11) O—$C_{1-6}$ fluoroalkyl, (12) $N(R^C)R^D$, (13) $N(R^A)$—$(CH_2)_{2-3}$—$N(R^C)R^D$, (14) $C(O)N(R^A)R^B$, (15) $C(O)R^A$, (16) $C(O)OR^A$, (17) $SR^A$, (18) $S(O)R^A$, (19) $S(O)_2R^A$, and (20) $S(O)_2N(R^A)R^B$;

$R^9$ is H or $C_{1-4}$ alkyl;

AryA is phenyl or naphthyl, wherein the phenyl is optionally substituted with from 1 to 3 substituents each of which is independently $C_{1-6}$ alkyl, O—$C_{1-6}$ alkyl, $CF_3$, $OCF_3$, OH, halogen, CN, $NO_2$, $N(R^A)R^B$, $C(O)N(R^A)R^B$, $C(O)R^A$, $C(O)CF_3$, $CO_2R^A$, $SO_2R^A$, CH═CH—$(CH_2)_{0-2}$CN, C≡C—$(CH_2)_{1-2}N(R^A)R^B$, or $C_{1-6}$ alkylene-$N(R^A)R^B$;

AryB is phenyl which is optionally substituted with from 1 to 2 substituents each of which is independently Cl, Br, F, CN, $NO_2$, $C_{1-4}$ alkyl, $CF_3$, OH, O—$C_{1-4}$ alkyl, $OCF_3$, $C(O)N(R^A)R^B$, $C(O)R^A$, $CO_2R^A$, $S(O)_2R^A$, or $S(O)_2N(R^A)R^B$;

HetB is a heteroaromatic ring selected from the group consisting of pyrrolyl, pyrazolyl, oxazolyl, thiazolyl, imidazolyl, oxadiazolyl, pyridyl and pyrimidinyl, wherein the heteroaromatic ring is optionally substituted with from 1 to 2 substituents, each of which is independently Cl, Br, F, CN, $NO_2$, $C_{1-4}$ alkyl, $CF_3$, OH, O—$C_{1-4}$ alkyl, $OCF_3$, $C(O)N(R^A)R^B$, $C(O)R^A$, $CO_2R^A$, $SO_2R^A$, $SO_2N(R^A)R^B$, or phenyl, with the proviso that no more than 1 of the optional substituents is phenyl;

HetC is a saturated heterocyclic ring selected from the group consisting of 1-pyrrolidinyl, 1-piperidinyl, 4-morpholinyl, 4-thiomorpholinyl in which the S is optionally oxidized to S(O) or $S(O)_2$, and 1-piperazinyl, wherein the saturated heterocyclic ring is optionally substituted with from 1 to 2 substituents each of which is Cl, Br, F, CN, $C_{1-4}$ alkyl, OH, oxo, O—$C_{1-4}$ alkyl, $CF_3$, $OCF_3$, $C(O)N(R^A)R^B$, $C(O)R^A$, $CO_2R^A$, $S(O)_2R^A$, or $S(O)_2N(R^A)R^B$;

each $R^A$ is independently H or $C_{1-6}$ alkyl;

each $R^B$ is independently H or $C_{1-6}$ alkyl;

each $R^C$ is independently H or $C_{1-6}$ alkyl;

each $R^D$ is independently H or $C_{1-6}$ alkyl; and alternatively and independently each pair of $R^C$ and $R^D$ together with the N atom to which they are both attached form a 4- to 7-membered, saturated monocyclic ring optionally containing 1 heteroatom in addition to the nitrogen attached to $R^C$ and $R^D$ selected from N, O, and S, where the S is optionally oxidized to S(O) or $S(O)_2$; and wherein the monocyclic ring is optionally substituted with 1 or 2 substituents each of which is independently: (1) $C_{1-4}$ alkyl, (2) $CF_3$, (3) $C(O)N(R^A)R^B$, (4) $C(O)R^A$, (5) C(O)—$CF_3$, (6) $C(O)OR^A$, or (7) $S(O)_2R^A$;

and all other variables are as originally defined.

A sub-class of Class C6 (i.e., Sub-class SC6-1) includes the compounds of Formula I and their pharmaceutically acceptable salts, wherein V is CH; W is $C(R^3)$; either (i) Z and Y are both C and ring A is benzo, or (ii) Z is N and Y is C and ring A is pyrido or dihydropyrido; ring B is a 4- to 7-membered saturated or unsaturated ring containing from 1 to 3 N atoms; and all other variables are as originally defined in Class C6.

Another sub-class of Class C6 (Sub-class SC6-2) includes the compounds of Formula I and their pharmaceutically acceptable salts, wherein all the variables are as originally defined in Class C6; and provided that:

(A) when ring B is

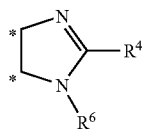

and $R^4$ is other than H, then $R^6$ is not

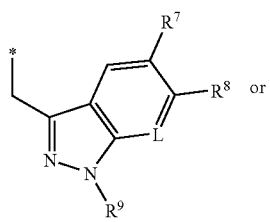

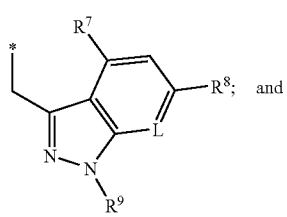

(B) when ring B is

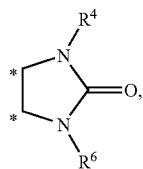

then $R^6$ is not

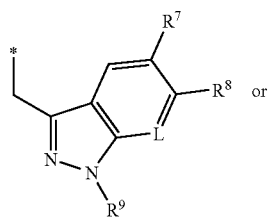

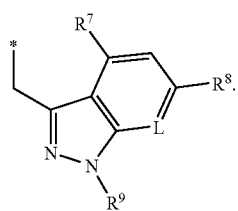

A seventh class of compounds of the present invention (Class C7) includes compounds of Formula I and pharmaceutically acceptable salts thereof, wherein:

$R^6$ is

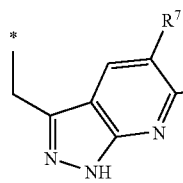 or 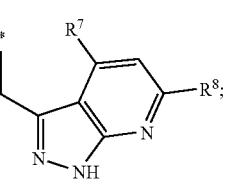

and all other variables are as originally defined in Class C6.

A sub-class of Class C7 (Sub-class SC7-1) includes the compounds of Formula I and their pharmaceutically acceptable salts, wherein all the variables are as originally defined in Class C7; and provided that:

(A) when ring B is

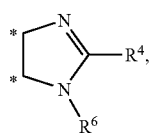

then $R^4$ is H; and (B) ring B is not

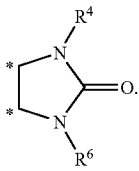

An eighth class of compounds of the present invention (Class C8) includes compounds of Formula I and pharmaceutically acceptable salts thereof, wherein: V and W are both CH; Z and Y are both C; ring A is benzo; ring B is a 4- to 7-membered saturated or unsaturated ring containing from 1 to 3 N atoms; and all other variables are as defined in Class C7.

A ninth class of compounds of the present invention (Class C9) includes compounds of Formula IX:

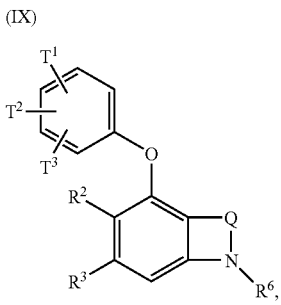

(IX)

and pharmaceutically acceptable salts thereof, wherein:

$T^1$ and $T^2$ and $T^3$ are each independently H, $C_{1-4}$ alkyl, halogen, CN, CH=CH—CN, C(O)$R^A$, or $(CH_2)_{1-2}N(R^A)R^B$;

$R^2$ and $R^3$ are each independently selected from the group consisting of: (1) H, (2) halogen, (3) N($R^A$)$R^B$, (4) $C_{1-4}$ alkyl, (5) $CF_3$, (6) O—$C_{1-4}$ alkyl, and (7) $OCF_3$;

(1)

$R^6$ is:

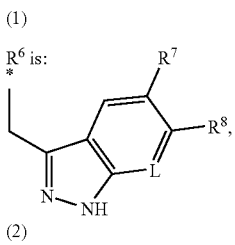

(2)

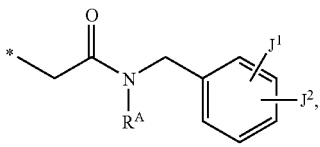

(3)

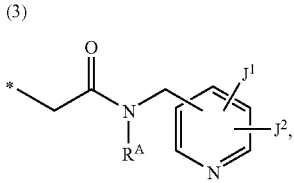

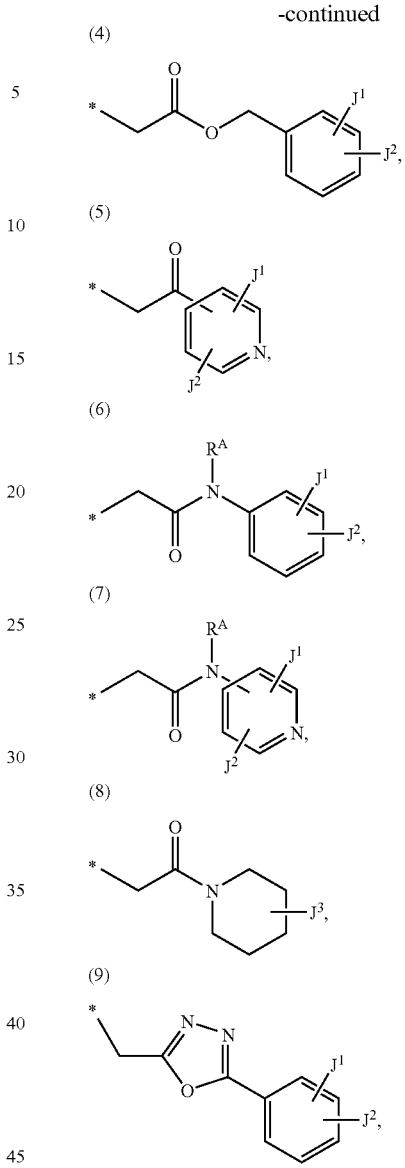

or (10) *—$CH_2CH_2OH$;

$J^1$ and $J^2$ are each independently H, Cl, Br, F, CN, $NO_2$, $C_{1-4}$ alkyl, $CF_3$, OH, O—$C_{1-14}$ alkyl, $OCF_3$, C(O)N($R^A$)$R^B$, C(O)$R^A$, $CO_2R^A$, $SO_2R^A$, or $SO_2N(R^A)R^B$;

$J^3$ is H, Cl, Br, F, CN, $C_{1-4}$ alkyl, OH, oxo, O—$C_{1-4}$ alkyl, $CF_3$, $OCF_3$, C(O)$NH_2$, C(O)N(H)$CH_3$, C(O)N($R^A$)$R^B$, C(O)$R^A$, $CO_2R^A$, $SO_2R^A$, or $SO_2N(R^A)R^B$;

L is N or N oxide;

Q is: (1) —CH($R^4$)—, (2) —C($R^4$)=C($R^5$)—, (3) —CH($R^4$)—CH($R^5$)—, (4) —C($R^4$)=C($R^5$)—$CH_2$—, (5) —CH($R^4$)—CH($R^5$)—$CH_2$—, (6) —C($R^4$)=C($R^5$)—CH=CH—, (7) —CH($R^4$)—CH($R^5$)—CH=CH—, (8) —C($R^4$)=C($R^5$)—$CH_2CH_2$—, (9) —CH($R^4$)—CH($R^5$)—$CH_2CH_2$—, (10) —C($R^4$)=N—, (11) —N=C($R^4$)—, or (12) —N=N—; wherein the left-most atom in Q is the atom directly attached to the fused benzo;

$R^4$ and $R^5$ are each independently selected from the group consisting of: (1) H, (2) $C_{1-4}$ alkyl, (3) O—$C_{1-4}$ alkyl, (4) $CF_3$, (5) $OCF_3$, and (6) halogen;

$R^7$ and $R^8$ are each independently selected from the group consisting of: (1) H, (2) OH, (3) halogen, (4) CN, (5) $NO_2$, (6) $C_{1-4}$ alkyl, (7) O—$C_{1-4}$ alkyl, (8) $O(CH_2)_{2-3}N(R^A)R^B$, (9) $O(CH_2)_{1-3}C(O)R^A$, (10) $CF_3$, (11) $OCF_3$, (12) $O(CH_2)_{1-2}CF_3$, (12) $N(R^C)R^D$, (13) $N(R^A)—(CH_2)_{2-3}—N(R^C)R^D$, and (14) $C(O)N(R^A)R^B$;

each $R^A$ is independently H or $C_{1-4}$ alkyl;

each $R^B$ is independently H or $C_{1-4}$ alkyl;

each $R^C$ is independently H or $C_{1-4}$ alkyl;

each $R^D$ is independently H or $C_{1-4}$ alkyl; and alternatively and independently each pair of $R^C$ and $R^D$ together with the N atom to which they are both attached form a saturated monocyclic ring selected from the group consisting of:

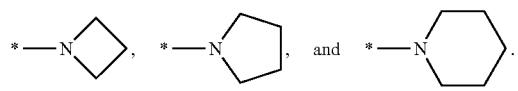

A sub-class of Class C9 (Sub-class SC9-1) includes the compounds of Formula IX and their pharmaceutically acceptable salts, wherein all the variables are as originally defined in Class C9; and provided that:

(A) when Q is —N═C($R^4$)— and $R^4$ is other than H, then $R^6$ is not

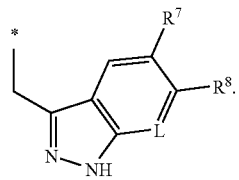

Another sub-class of Class C9 (Sub-class SC9-2) includes the compounds of Formula IX and their pharmaceutically acceptable salts, wherein $J^1$ and $J^2$ are each independently H, Cl, Br, F, CN, $NO_2$, $C_{1-3}$ alkyl, $CF_3$, OH, O—$C_{1-3}$ alkyl, $OCF_3$, $C(O)NH_2$, $C(O)N(H)CH_3$, $C(O)N(CH_3)_2$, $C(O)H$, $C(O)CH_3$, $CO_2H$, $CO_2CH_3$, $SO_2CH_3$, or $SO_2NH_2$; $J^3$ is H, Cl, Br, F, CN, $C_{1-3}$ alkyl, OH, oxo, O—$C_{1-3}$ alkyl, $CF_3$, $OCF_3$, $C(O)NH_2$, $C(O)N(H)CH_3$, $C(O)N(CH_3)_2$, $C(O)H$, $C(O)CH_3$, $CO_2H$, $CO_2CH_3$, $SO_2CH_3$, or $SO_2NH_2$; and all other variables are as originally defined in Class C9 or Sub-class SC9-1.

Another sub-class of Class C9 (Sub-class SC9-3) includes the compounds of Formula IX and their pharmaceutically acceptable salts, wherein Q is —$CH_2CH_2CH_2$—, —CH═N—, —C(Cl)═N—, —N═CH—, or —N═N—; and all other variables are as originally defined in Class C9 or Sub-class SC9-2.

A tenth class of compounds of the present invention (Class C10) includes compounds of Formula IXa:

(IXa)

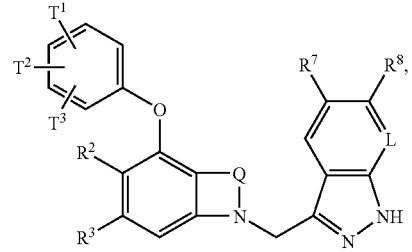

and pharmaceutically acceptable salts thereof, wherein all the variables are as originally defined in Class C9.

A sub-class of Class C10 (Sub-class SC10-1) includes the compounds of Formula IXa and their pharmaceutically acceptable salts, wherein all the variables are as originally defined in Class C9; and provided that when Q is —N═C($R^4$)—, then $R^4$ is H.

Another sub-class of Class C10 (Sub-class SC10-2) includes the compounds of Formula IXa and their pharmaceutically acceptable salts, wherein $J^1$ and $J^2$ are each independently H, Cl, Br, F, CN, $NO_2$, $C_{1-3}$ alkyl, $CF_3$, OH, O—$C_{1-3}$ alkyl, $OCF_3$, $C(O)NH_2$, $C(O)N(H)CH_3$, $C(O)N(CH_3)_2$, $C(O)H$, $C(O)CH_3$, $CO_2H$, $CO_2CH_3$, $SO_2CH_3$, or $SO_2NH_2$; $J^3$ is H, Cl, Br, F, CN, $C_{1-3}$ alkyl, OH, oxo, O—$C_{1-3}$ alkyl, $CF_3$, $OCF_3$, $C(O)NH_2$, $C(O)N(H)CH_3$, $C(O)N(CH_3)_2$, $C(O)H$, $C(O)CH_3$, $CO_2H$, $CO_2CH_3$, $SO_2CH_3$, or $SO_2NH_2$; and all other variables are as originally defined in Class C10 or Sub-class SC10-1.

An eleventh class of compounds of the present invention (Class C11) includes compounds of Formula IXb:

(IXb)

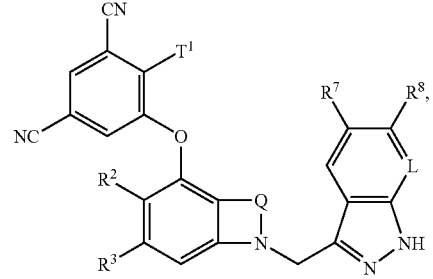

and pharmaceutically acceptable salts thereof, wherein Q is: (1) —CH═CH—, (2) —CH═CH—$CH_2$—, (3) —CH═CH—CH═CH—, (4) —$CH_2CH_2$—CH═CH—, (5) —CH═CH—$CH_2CH_2$—, (6) —C($R^4$)═N—, (7) —N═CH—, (8) —N═N—, or (9) $CH_2CH_2CH_2$;

$T^1$ is H or Cl;

$R^2$ and $R^3$ are each independently selected from the group consisting of H, Cl, Br, F and $C_{1-4}$ alkyl;

$R^4$ is H, $C_{1-4}$ alkyl, Cl, Br, or F;

L is N or N oxide; and one of $R^7$ and $R^8$ is H, OH, Cl, Br, F, $CH_3$, $OCH_3$, $O(CH_2)_{2-3}NH_2$, $CF_3$, $OCF_3$, $OCH_2CF_3$, $NH_2$, $N(H)CH_3$, $N(CH_3)_2$, $C(O)NH_2$, $C(O)N(H)CH_3$, or $C(O)N(CH_3)_2$; and the other of $R^7$ and $R^8$ is H.

A sub-class of Class C11 (Sub-class SC1-1) includes the compounds of Formula IXb and their pharmaceutically acceptable salts, wherein all of the variables are as originally defined in Class C11; and provided that when Q is —N=C(R$^4$)—, then R$^4$ is H.

Another sub-class of Class C11 (Sub-class SC11-2) includes the compounds of Formula IXb and their pharmaceutically acceptable salts, wherein Q is CH$_2$CH$_2$CH$_2$, —CH=N—, —C(Cl)=N—, —N=CH—, or —N=N—; and all other variables are as originally defined in Class C11.

A twelfth class of compounds of the present invention (Class C12) includes compounds of Formula IXc:

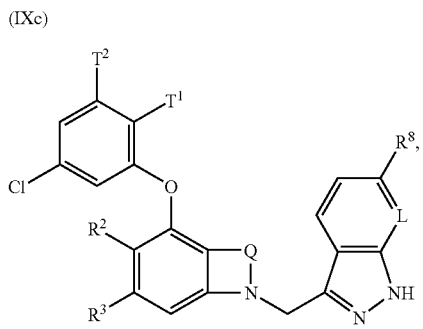

(IXc)

and pharmaceutically acceptable salts thereof, wherein:

T$^1$ is H or Cl;

T$^2$ is CN, CH(O), CH$_2$NH$_2$, or CH$_2$N(H)CH$_3$;

R$^8$ is H, OH, Cl, Br, F, CH$_3$, OCH$_3$, O(CH$_2$)$_{2-3}$NH$_2$, CF$_3$, OCF$_3$, OCH$_2$CF$_3$, NH$_2$, N(H)CH$_3$, N(CH$_3$)$_2$, C(O)NH$_2$, C(O)N(H)CH$_3$, or C(O)N(CH$_3$)$_2$; and Q, R$^2$, R$^3$, R$^4$ and L are as defined in Class C11.

A sub-class of Class C12 (Sub-class SC12-1) includes the compounds of Formula IXb and their pharmaceutically acceptable salts, wherein all of the variables are as originally defined in Class C12; and provided that when Q is —N=C(R$^4$)—, then R$^4$ is H.

Another sub-class of Class C12 (Sub-class SC12-2) includes the compounds of Formula IXc and their pharmaceutically acceptable salts, wherein Q is CH$_2$CH$_2$CH$_2$, —CH=N—, —C(Cl)=N—, —N=CH—, or —N=N—; and all other variables are as originally defined in Class C12.

A thirteenth class of compounds of the present invention (Class C13) includes compounds of Formula IXd:

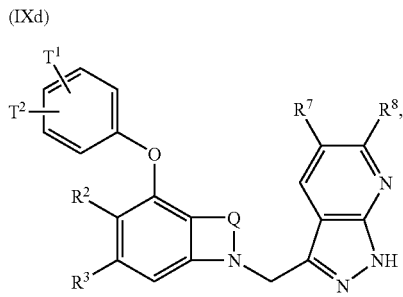

(IXd)

and pharmaceutically acceptable salts thereof, wherein:

Q is: (1) —CH(R$^4$)—, (2) —C(R$^4$)=C(R$^5$)—, (3) —CH(R$^4$)—CH(R$^5$)—, (4) —C(R$^4$)=C(R$^5$)—CH$_2$—, (5) —CH(R$^4$)—CH(R$^5$)—CH$_2$—, (6) —C(R$^4$)=C(R$^5$)—CH=CH—, (7) —CH(R$^4$)—CH(R$^5$)—CH=CH—, (8) —C(R$^4$)=C(R$^5$)—CH$_2$CH$_2$—, (9) —CH(R$^4$)—CH(R$^5$)—CH$_2$CH$_2$—, (10) —C(R$^4$)=N—, (11) —N=C(R$^4$)—; or (12) —N=N—; wherein the left-most atom in Q is the atom directly attached to the fused benzo;

T$^1$ and T$^2$ are each independently H, C$_{1-4}$ alkyl, halogen, CN, or CH=CH—CN;

R$^2$ and R$^3$ are each independently selected from the group consisting of: (1) H, (2) halogen, (3) C$_{1-4}$ alkyl, (4) CF$_3$, (5) O—C$_{1-4}$ alkyl, (6) OCF$_3$, and (7) N(R$^A$)R$^B$;

R$^4$ and R$^5$ are each independently selected from the group consisting of: (1) H, (2) C$_{1-4}$ alkyl, (3) O—C$_{1-4}$ alkyl, (4) CF$_3$, (5) OCF$_3$, and (6) halogen;

R$^7$ and R$^8$ are each independently selected from the group consisting of: (1) H, (2) OH, (3) halogen, (4) CN, (5) NO$_2$, (6) C$_{1-4}$ alkyl, (7) O—C$_{1-4}$ alkyl, (8) O(CH$_2$)$_{2-3}$N(R$^A$)R$^B$, (9) O(CH$_2$)$_{1-3}$C(O)R$^A$, (10) CF$_3$, (11) OCF$_3$, (12) O(CH$_2$)$_{1-2}$CF$_3$, (12) N(R$^C$)R$^D$, (13) N(R$^A$)—(CH$_2$)$_{2-3}$—N(R$^C$)R$^D$, and (14) C(O)N(R$^A$)R$^B$;

each R$^A$ is independently H or C$_{1-4}$ alkyl;
each R$^B$ is independently H or C$_{1-4}$ alkyl;
each R$^C$ is independently H or C$_{1-4}$ alkyl;
each R$^D$ is independently H or C$_{1-4}$ alkyl; and
alternatively and independently each pair of R$^C$ and R$^D$ together with the N atom to which they are both attached form a saturated monocyclic ring selected from the group consisting of:

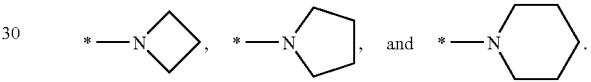

A sub-class of Class C13 (Sub-class SC13-1) includes the compounds of Formula IXd and their pharmaceutically acceptable salts, wherein all of the variables are as originally defined in Class C13; and provided that when Q is —N=C(R$^4$)—, then R$^4$ is H.

A fourteenth class of compounds of the present invention (Class C14) includes compounds of Formula IXe:

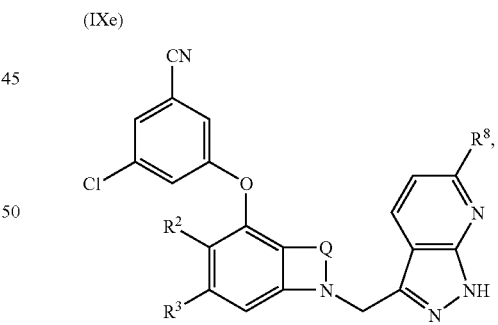

(IXe)

and pharmaceutically acceptable salts thereof, wherein:

Q is: (1) —CH=CH—, (2) —CH=CH—CH$_2$—, (3) —CH=CH—CH=CH—, (4) —CH$_2$CH$_2$—CH=CH—, (5) —CH=CH—CH$_2$CH$_2$—, (6) —C(R$^4$)=N—, (7) —N=C(R$^4$)—; or (8) —N=N—;

R$^2$ and R$^3$ are each independently selected from the group consisting of H, Cl, Br, F and C$_{1-4}$ alkyl;

R$^4$ is H, C$_{1-4}$ alkyl, Cl, Br, or F; and

R$^8$ is H, OH, Cl, Br, F, CH$_3$, OCH$_3$, O(CH$_2$)$_{2-3}$NH$_2$, CF$_3$, OCF$_3$, OCH$_2$CF$_3$, NH$_2$, N(H)CH$_3$, N(CH$_3$)$_2$, C(O)NH$_2$, C(O)N(H)CH$_3$, or C(O)N(CH$_3$)$_2$.

A sub-class of Class C14 (Sub-class SC14-1) includes the compounds of Formula IXe and their pharmaceutically acceptable salts, wherein all of the variables are as originally defined in Class C14; and provided that when Q is —N═C(R⁴)—, then R⁴ is H.

Another sub-class of Class C14 (Sub-class SC14-2) includes the compounds of Formula IXe and their pharmaceutically acceptable salts, wherein Q is —CH═N—, —C(Cl)═N—, —N═CH—, or —N═N—; R² is Br or Cl; R³ is H; and R⁸ is H or NH₂.

A fifteenth class of compounds of the present invention (Class C15) includes compounds of Formula X:

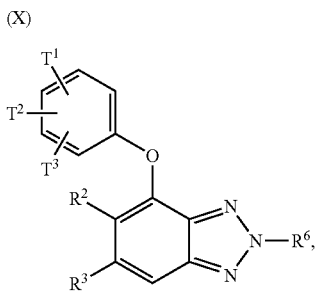

(X)

and pharmaceutically acceptable salts thereof, wherein all of the variables are as originally defined in Class C9.

A sub-class of Class C15 (Sub-class SC15-1) includes the compounds of Formula X and their pharmaceutically acceptable salts, wherein R⁶ is

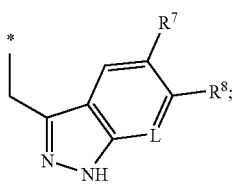

and all other variables are as originally defined in Class C15.

Another sub-class of Class C15 (Sub-class SC15-2) includes the compounds of Formula X and their pharmaceutically acceptable salts, wherein J¹ and J² are each independently H, Cl, Br, F, CN, NO₂, C₁₋₃ alkyl, CF₃, OH, O—C₁₋₃ alkyl, OCF₃, C(O)NH₂, C(O)N(H)CH₃, C(O)N(CH₃)₂, C(O)H, C(O)CH₃, CO₂H, CO₂CH₃, SO₂CH₃, or SO₂NH₂; J³ is H, Cl, Br, F, CN, C₁₋₃ alkyl, OH, oxo, O—C₁₋₃ alkyl, CF₃, OCF₃, C(O)NH₂, C(O)N(H)CH₃, C(O)N(CH₃)₂, C(O)H, C(O)CH₃, CO₂H, CO₂CH₃, SO₂CH₃, or SO₂NH₂; and all other variables are as originally defined in Class C15.

Another sub-class of Class C15 (Sub-class SC15-3) includes the compounds of Formula X and their pharmaceutically acceptable salts, wherein:

T¹ and T² and T³ are each independently H, C₁₋₄ alkyl, halogen, or CN;

R⁶ is

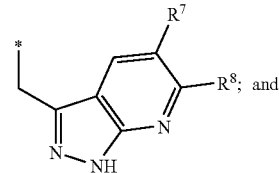

R² and R³ are each independently selected from the group consisting of H, Cl, Br, F and C₁₋₄ alkyl; one of R⁷ and R⁸ is H, OH, Cl, Br, F, CH₃, OCH₃, O(CH₂)₂₋₃NH₂, CF₃, OCF₃, OCH₂CF₃, NH₂, N(H)CH₃, N(CH₃)₂, C(O)NH₂, C(O)N(H)CH₃, or C(O)N(CH₃)₂; and the other of R⁷ and R⁸ is H.

Another sub-class of Class C15 (Sub-class SC15-4) includes the compounds of Formula X and their pharmaceutically acceptable salts, wherein:

T¹ and T² and T³ are each independently H, CH₃, Cl, or CN, with the proviso that at least one of T¹ and T² and T³ is Cl and at least one of T¹ and T² and T³ is CN;

R² and R³ are each independently selected from the group consisting of H, Cl, Br, F and C₁₋₄ alkyl;

R⁶ is

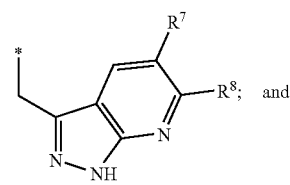

one of R⁷ and R⁸ is H, OH, Cl, Br, F, CH₃, OCH₃, NH₂, N(H)CH₃, or N(CH₃)₂.

A sixteenth class of compounds of the present invention (Class C16) includes compounds of Formula XI:

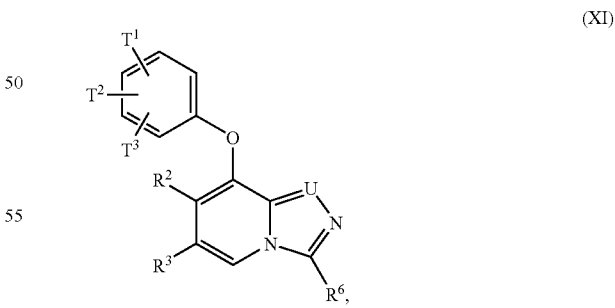

(XI)

and pharmaceutically acceptable salts thereof, wherein U is CH or N; all other variables are as originally defined in Class C9.

A sub-class of Class C16 (Sub-class SC16-1) includes the compounds of Formula XI and their pharmaceutically acceptable salts, wherein R⁶ is

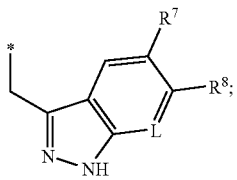

and all other variables are as originally defined in Class C16.

Another sub-class of Class C16 (Sub-class SC16-2) includes the compounds of Formula XI and their pharmaceutically acceptable salts, wherein $J^1$ and $J^2$ are each independently H, Cl, Br, F, CN, $NO_2$, $C_{1-3}$ alkyl, $CF_3$, OH, O—$C_{1-3}$ alkyl, $OCF_3$, $C(O)NH_2$, $C(O)N(H)CH_3$, $C(O)N(CH_3)_2$, C(O)H, $C(O)CH_3$, $CO_2H$, $CO_2CH_3$, $SO_2CH_3$, or $SO_2NH_2$; $J^3$ is H, Cl, Br, F, CN, $C_{1-3}$ alkyl, OH, oxo, O—$C_{1-3}$ alkyl, $CF_3$, $OCF_3$, $C(O)NH_2$, $C(O)N(H)CH_3$, $C(O)N(CH_3)_2$, C(O)H, $C(O)CH_3$, $CO_2H$, $CO_2CH_3$, $SO_2CH_3$, or $SO_2NH_2$; and all other variables are as originally defined in Class C15.

Another sub-class of Class C16 (Sub-class SC16-3) includes the compounds of Formula XI and their pharmaceutically acceptable salts, wherein:

$T^1$ and $T^2$ and $T^3$ are each independently H, $C_{1-4}$ alkyl, halogen, or CN;

$R^6$ is

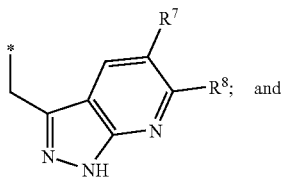 and $R^2$ and $R^3$ are each independently selected from the group consisting of H, Cl, Br, F and $C_{1-4}$ alkyl; one of $R^7$ and $R^8$ is H, OH, Cl, Br, F, $CH_3$, $OCH_3$, $O(CH_2)_{2-3}NH_2$, $CF_3$, $OCF_3$, $OCH_2CF_3$, $NH_2$, $N(H)CH_3$, $N(CH_3)_2$, $C(O)NH_2$, $C(O)N(H)CH_3$, or $C(O)N(CH_3)_2$; and the other of $R^7$ and $R^8$ is H.

Another sub-class of Class C16 (Sub-class SC16-4) includes the compounds of Formula XI and their pharmaceutically acceptable salts, wherein:

$T^1$ and $T^2$ and $T^3$ are each independently H, $CH_3$, Cl, or CN, with the proviso that at least one of $T^1$ and $T^2$ and $T^3$ is Cl and at least one of $T^1$ and $T^2$ and $T^3$ is CN;

$R^2$ and $R^3$ are each independently selected from the group consisting of H, Cl, Br, F and $C_{1-4}$ alkyl;

$R^6$ is

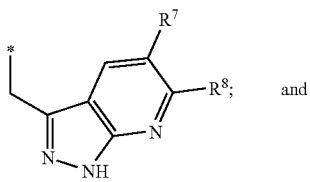

one of $R^7$ and $R^8$ is H, OH, Cl, Br, F, $CH_3$, $OCH_3$, $NH_2$, $N(H)CH_3$, or $N(CH_3)_2$.

A seventeenth class of the present invention (Class C17) includes compounds selected from the group consisting of the compounds set forth in Examples 1-7, 9-13 and 15-29 and their pharmaceutically acceptable salts. A sub-class of Class C17 (Sub-class SC17-1) includes compounds selected from the group consisting of the compounds set forth in Examples 1 to 4 and their pharmaceutically acceptable salts.

Another embodiment of the present invention is a compound of Formula I, or a pharmaceutically acceptable salt thereof, as originally defined or as defined in any of the foregoing embodiments, aspects, classes or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest purity level governs. A compound or salt of 100% purity is one which is free of detectable impurities as determined by a standard method of analysis. With respect to a compound of the invention which has one or more asymmetric centers and can occur as mixtures of stereoisomers, a substantially pure compound can be either a substantially pure mixture of the stereoisomers or a substantially pure individual diastereomer or enantiomer.

The present invention also includes prodrugs of the compounds of Formula I. The term "prodrug" refers to a derivative of a compound of Formula I, or a pharmaceutically acceptable salt thereof, which is converted in vivo into Compound I. Prodrugs of compounds of Formula I can exhibit enhanced solubility, absorption, and/or lipophilicity compared to the compounds per se, thereby resulting in increased bioavailability and efficacy. The in vivo conversion of the prodrug can be the result of an enzyme-catalyzed chemical reaction, a metabolic chemical reaction, and/or a spontaneous chemical reaction (e.g., solvolysis). When the compound contains, for example, a hydroxy group, the prodrug can be a derivative of the hydroxy group such as an ester (—OC(O)R), a carbonate ester (—OC(O)OR), a phosphate ester (—O—P(=O)(OH)$_2$), or an ether (—OR). Other examples include the following: When the compound of Formula I contains a carboxylic acid group, the prodrug can be an ester or an amide, and when the compound of Formula I contains a primary amino group or another suitable nitrogen that can be derivatized, the prodrug can be an amide, carbamate, urea, imine, or a Mannich base. One or more functional groups in Compound I can be derivatized to provide a prodrug thereof. Conventional procedures for the selection and preparation of suitable prodrug derivatives are described, for example, in *Design of Prodrugs*, edited by H. Bundgaard, Elsevier, 1985; J. J. Hale et al., *J. Med. Chem.* 2000, vol. 43, pp. 1234-1241; C. S. Larsen and J. Ostergaard, "Design and application of prodrugs" in: *Textbook of Drug Design and Discovery*, 3$^{rd}$ edition, edited by C. S. Larsen, 2002, pp. 410-458; and Beaumont et al., *Current Drug Metabolism* 2003, vol. 4, pp. 461-458; the disclosures of each of which are incorporated herein by reference in their entireties.

Another embodiment of the present invention (alternatively referred to as "Embodiment PD1") is a prodrug of a compound of Formula I as originally defined above.

Another embodiment of the present invention (Embodiment PD2) is a compound of Formula I-P:

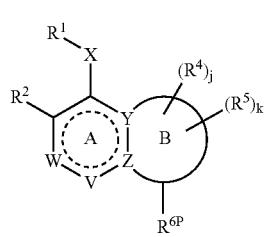

(I-P)

wherein:

$R^{6P}$ is attached to the ring atom in B which is adjacent to shared atom Z or which is adjacent to the ring atom that is adjacent to Z, and is

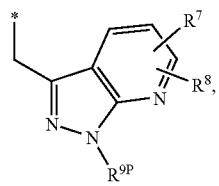

wherein each ring N is optionally an N-oxide;

$R^{9P}$ is $PO(OH)O^- M^+$; $PO(O^-)_2.2M^+$; $PO(O^-)_2.M^{2+}$; or an acid salt of:

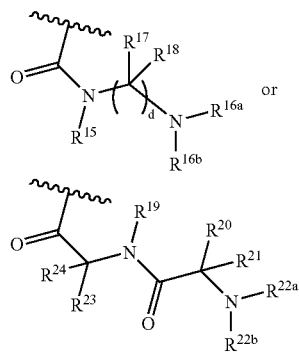

$M^+$ is a pharmaceutically acceptable monovalent counterion;
$M^{2+}$ is a pharmaceutically acceptable divalent counterion;
$R^{15}$ is H, $C_{1-6}$ alkyl, $(CH_2)_{2-3}CF_3$, AryA, or HetA;
$R^{16a}$ and $R^{16b}$ are each independently H, $C_{1-6}$ alkyl, $(CH_2)_{2-3}$ $CF_3$, AryA, or HetA;
each $R^{17}$ is independently H or $C_{1-6}$ alkyl;
each $R^{18}$ is independently H or $C_{1-6}$ alkyl;
alternatively, $R^{15}$ together with an $R^{17}$ or $R^{18}$ and the atoms to which each is attached and any carbons in a chain therebetween form a 5- to 7-membered, saturated or unsaturated monocyclic ring optionally containing a heteroatom in addition to the N atom to which $R^{15}$ is attached, wherein the optional heteroatom is selected from N, O and S, where the S is optionally oxidized to S(O) or $S(O)_2$;
alternatively, $R^{16a}$ together with an $R^{17}$ or $R^{18}$ and the atoms to which each is attached and any carbons in a chain therebetween form a 5- to 7-membered, saturated or unsaturated monocyclic ring optionally containing a heteroatom in addition to the N atom to which $R^{16a}$ is attached, wherein the optional heteroatom is selected from N, O and S, where the S is optionally oxidized to S(O) or $S(O)_2$;
alternatively, an $R^{17}$ together with the $R^{18}$ attached to the same carbon atom form a 5- or 6-membered, saturated monocyclic ring optionally containing a heteroatom, wherein the optional heteroatom is selected from N, O and S, where the S is optionally oxidized to S(O) or $S(O)_2$;
$R^{19}$ is H or $C_{1-6}$ alkyl;
$R^{20}$ is H or $C_{1-6}$ alkyl;
$R^{21}$ is H or $C_{1-6}$ alkyl;
$R^{22a}$ and $R^{22b}$ are each independently H, $C_{1-6}$ alkyl, $(CH_2)_{2-3}CF_3$, AryA, or HetA;
$R^{23}$ is H or $C_{1-6}$ alkyl;
$R^{24}$ is H or $C_{1-6}$ alkyl;
alternatively, $R^{19}$ together with $R^{23}$ or $R^{24}$ and the atoms to which each is attached form a 5- to 7-membered, saturated or unsaturated monocyclic ring optionally containing a heteroatom in addition to the N atom to which $R^{19}$ is attached, wherein the optional heteroatom is selected from N, O and S, where the S is optionally oxidized to S(O) or $S(O)_2$;
alternatively, $R^{20}$ and $R^{21}$ together with the carbon atom to which both are attached form a 5- or 6-membered, saturated monocyclic ring optionally containing a heteroatom, wherein the optional heteroatom is selected from N, O and S, where the S is optionally oxidized to S(O) or $S(O)_2$;
alternatively, $R^{22a}$ together with an $R^{20}$ or $R^{21}$ and the atoms to which each is attached form a 5- to 7-membered, saturated or unsaturated monocyclic ring optionally containing a heteroatom in addition to the N atom to which $R^{22a}$ is attached, wherein the optional heteroatom is selected from N, O and S, where the S is optionally oxidized to S(O) or $S(O)_2$;
alternatively, $R^{23}$ and $R^{24}$ together with the carbon atom to which both are attached form a 5- or 6-membered, saturated monocyclic ring optionally containing a heteroatom, wherein the optional heteroatom is selected from N, O and S, where the S is optionally oxidized to S(O) or $S(O)_2$;
wherein the monocyclic ring formed by combining $R^{15}$ together with an $R^{17}$ or $R^{18}$, the monocyclic ring formed by combining $R^{16a}$ together with an $R^{17}$ or $R^{18}$, the monocyclic ring formed by combining $R^{17}$ together with an $R^{18}$, the monocyclic ring formed by combining $R^{19}$ together with an $R^{23}$ or $R^{24}$, the monocyclic ring formed by combining $R^{20}$ together with an $R^{21}$, the monocyclic ring formed by combining $R^{22a}$ together with an $R^{20}$ or $R^{21}$, and the monocyclic ring formed by combining $R^{23}$ together with an $R^{24}$, are each independently and optionally substituted with from 1 to 3 substituents each of which is independently: (1) $C_{1-6}$ alkyl, (2) $C_{1-6}$ haloalkyl, (3) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $SO_2R^A$, or $SO_2N(R^A)R^B$, (4) O—$C_{1-6}$ alkyl, (5) O—$C_{1-6}$ haloalkyl, (6) OH, (7) oxo, (8) halogen, (9) CN, (10) $NO_2$, (11) $N(R^A)R^B$, (12) $C(O)N(R^A)R^B$, (13) $C(O)R^A$, (14) $C(O)$—$C_{1-6}$ haloalkyl, (15) $C(O)OR^A$, (16) $OC(O)N(R^A)R^B$, (17) $SR^A$, (18) $S(O)R^A$, (19) $S(O)_2R^A$, (20) $S(O)_2N(R^A)R^B$, (21) $N(R^A)COR^B$, or (22) $N(R^A)SO_2R^B$;
d is an integer equal to 2, 3, or 4; and
all other variables are as originally defined above for a compound of Formula I.

In the definition of the monocyclic ring formed by combining $R^{15}$ together with an $R^{17}$ or $R^{18}$, the phrase "any carbons in a chain therebetween" refers to the carbon chain $[C(R^{17})R^{18}]_{2-4}$. If the ring is formed by combining $R^{15}$ with the $R^{17}$ or $R^{18}$ on the adjacent carbon, there are no carbons therebetween as exemplified by structure A below, wherein the arrow symbolizes the joining of $R^{15}$ and $R^{17}$ to form a ring. If the ring is formed by combining $R^{15}$ with the $R^{17}$ or $R^{18}$ on a non-adjacent carbon, there is at least one carbon therebetween as exemplified by structure B below. Analogous considerations apply with respect to the monocyclic ring formed by combining $R^{16a}$ together with an $R^{17}$ or $R^{18}$.

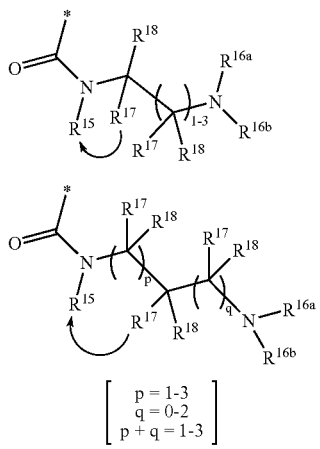

(A)

(B)

$$\begin{bmatrix} p = 1-3 \\ q = 0-2 \\ p + q = 1-3 \end{bmatrix}$$

Another embodiment of the present invention (Embodiment PD3) is a compound of Formula I-P as defined in Embodiment PD2; and provided that (A) when ring B is

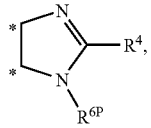

then $R^4$ is H; and (B) ring B is not

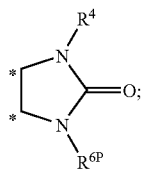

wherein the asterisks on ring B denote the points of attachment to ring A.

Another embodiment of the present invention (Embodiment PD4) is a compound of Formula I-P as defined in Embodiment PD2, wherein $R^{6P}$ is attached to the ring atom in B which is adjacent to shared atom Z; HetE and HetF are as defined in Embodiment E2; and all other variables are as defined in Embodiment PD2.

Another embodiment of the present invention (Embodiment PD5) is a compound of Formula I-P as defined in Embodiment PD4; and provided that (A) when ring B is

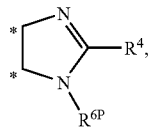

then $R^4$ is H; and (B) ring B is not

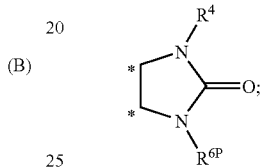

wherein the asterisks on ring B denote the points of attachment to ring A.

Another embodiment of the present invention (Embodiment PD6) is a compound of Formula I-P, wherein the compound is selected from the group consisting of:

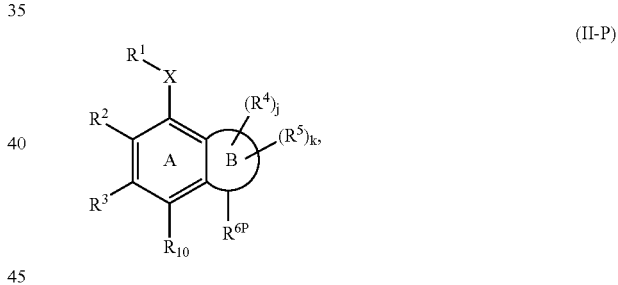

(II-P)

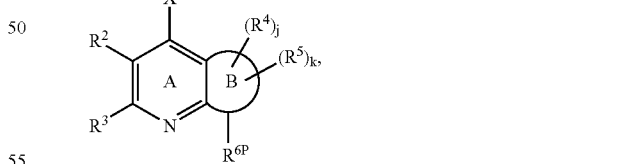

(III-P)

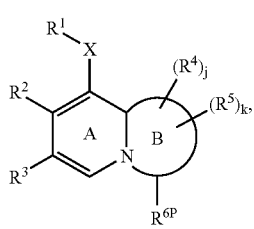

(IV-P)

-continued

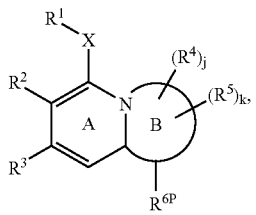
(V-P)

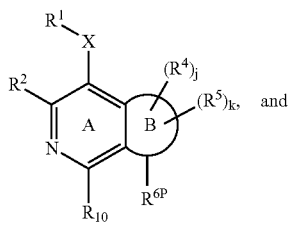
(VI-P)

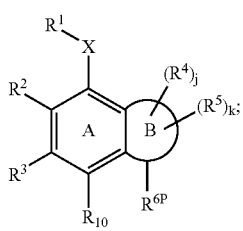
(VII-P)

wherein all of the variables are as defined in Embodiment PD2 or Embodiment PD3.

Another embodiment of the present invention (Embodiment PD7) is a compound of Formula I-P, wherein the compound is selected from the group consisting of compounds of Formula I-P, III-P, IV-P, V-P, and VI-P as defined in Embodiment PD6 wherein all of the variables are as defined in Embodiment PD4 or Embodiment PD5.

Another embodiment of the present invention (Embodiment PD8) is a compound of Formula I-P, wherein the compound is selected from the group consisting of compounds of Formula IIa-P, IIb-P, IIc-P, IId-P, IIe-P, IIf-P, IIg-P, IIh-P, IIi-P, IIj-P, IIk-P, IIl-P, IIm-P, IIn-P, IIo-P, IIp-P, IIq-P, IIr-P, IIIa-P, IVa-P, IVb-P, IVc-P, Va-P, VIa-P, and VIIa-P wherein these formulas are identical to Formulas IIa, IIb, IIc, IId, IIe, IIf, IIg, IIh, IIi, IIj, IIk, IIl, IIm, IIn, IIo, IIp, IIq, IIr, IIIa, IVa, IVb, IVc, Va, VIIa and VIIa respectively as set forth above in Class C2, except that $R^6$ is replaced with $R^{6P}$; and wherein all of the variables are as defined in Embodiment PD2 or Embodiment PD3.

Another embodiment of the present invention (Embodiment PD9) is a compound of Formula I-P, wherein the compound is selected from the group consisting of compounds of Formula IIa-P, IIb-P, IIc-P, IId-P, IIe-P, IIf-P, IIg-P, IIh-P, IIi-P, IIj-P, IIk-P, IIl-P, IIm-P, IIn-P, IIo-P, IIp-P, IIq-P, IIr-P, IIIa-P, IVa-P, IVb-P, Va-P and VIa-P wherein these formulas are identical to Formulas IIa, IIb, IIc, IId, IIe, IIf, IIg, IIh, IIi, IIj, IIk, IIl, IIm, IIn, IIo, IIp, IIq, IIr, IIIa, IVa, IVb, Va and VIa respectively as set forth above in Class C2, except that $R^6$ is replaced with $R^{6P}$; and wherein all of the variables are as defined in Embodiment PD4 or Embodiment PD5.

Another embodiment of the present invention (Embodiment PD10) is a compound of Formula I-P, wherein $R^{6P}$ is

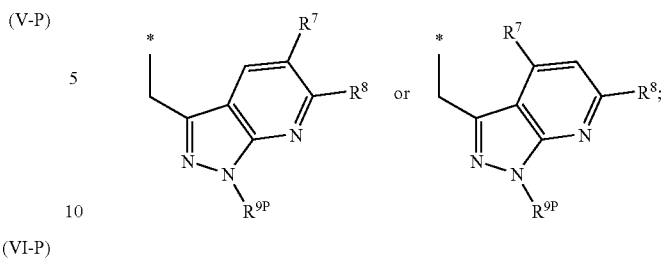

and X, $R^1$, $R^2$, $R^3$, $R^4$, $R^5$, $R^7$, $R^8$, $R^{10}$, $R^{11}$, $R^{12}$, AryA, $R^A$, $R^B$, $R^C$ and $R^D$ are each as defined in Class C6 set forth above; and all other variables (including $R^{9P}$) are as defined in Embodiment PD2.

Another embodiment of the present invention (Embodiment PD11) is a compound of Formula I-P, or a pharmaceutically acceptable salt thereof, wherein all the variables are as originally defined in Embodiment PD10; and provided that:
(A) when ring B is

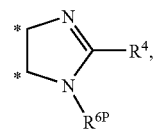

then $R^4$ is H; and (B) ring B is not

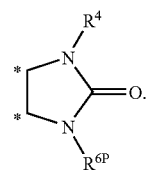

Another embodiment of the present invention (Embodiment PD12) is a compound of Formula I-P, wherein V and W are both CH; Z and Y are both C; ring A is benzo; ring B is a 4- to 7-membered saturated or unsaturated ring containing from 1 to 3 N atoms; and all other variables are as defined in Embodiment PD10 or Embodiment PD11.

Another embodiment of the present invention (Embodiment PD13) is a compound of Formula VIII-P:

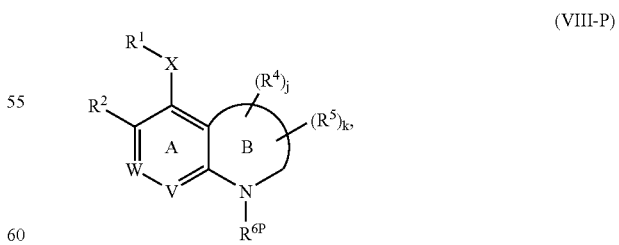
(VIII-P)

wherein all of the variables are as defined in any one of Embodiments PD2, PD3, PD4 and PD5. Compounds of Formula VIII-P as defined in Embodiments PD2, PD3, PD4 and PD5 respectively and wherein X is O form classes of compounds of interest.

Another embodiment of the present invention (Embodiment PD14) is a compound of Formula IX-P:

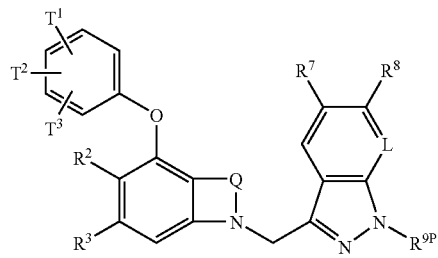

(IX-P)

wherein L, Q, $T^1$, $T^2$, $R^2$, $R^3$, $R^4$, $R^5$, $R^7$, $R^8$, $R^A$, $R^B$, $R^C$ and $R^D$ are as defined in Class C9; and $R^{9P}$ is as defined in Embodiment PD2.

Another embodiment of the present invention (Embodiment PD15) is a compound of Formula IX-P as defined in Embodiment PD14; and provided that (A) when Q is —N=C($R^4$)—, then $R^4$ is H.

Another embodiment of the present invention (Embodiment PD16) is a compound of Formula IX-P, wherein $J^1$ and $J_2$ are each independently H, Cl, Br, F, CN, $NO_2$, $C_{1-3}$ alkyl, $CF_3$, OH, O—$C_{1-3}$ alkyl, $OCF_3$, $C(O)NH_2$, $C(O)N(H)CH_3$, $C(O)N(CH_3)_2$, C(O)H, $C(O)CH_3$, $CO_2H$, $CO_2CH_3$, $SO_2CH_3$, or $SO_2NH_2$; $J^3$ is H, Cl, Br, F, CN, $C_{1-3}$ alkyl, OH, oxo, O—$C_{1-3}$ alkyl, $CF_3$, $OCF_3$, $C(O)NH_2$, $C(O)N(H)CH_3$, $C(O)N(CH_3)_2$, C(O)H, $C(O)CH_3$, $CO_2H$, $CO_2CH_3$, $SO_2CH_3$, or $SO_2NH_2$; and all other variables are as defined in Embodiment PD14 or Embodiment PD15.

Another embodiment of the present invention (Embodiment PD17) is a compound of Formula IX-P, wherein Q is —$CH_2CH_2CH_2$—, —CH=N—, —C(Cl)=N—, —N=CH—, or —N=N—; and all other variables are as originally defined in Embodiment PD14 or Embodiment PD16.

Another embodiment of the present invention (Embodiment PD18) is a compound of Formula IXa-P:

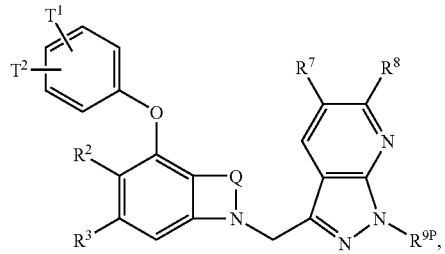

(IXa-P)

wherein Q, $T^1$, $T^2$, $R^2$, $R^3$, $R^4$, $R^5$, $R^7$, $R^8$, $R^A$, $R^B$, $R^C$ and $R^D$ are as defined in Class C13; and $R^{9P}$ is as defined in Embodiment PD2.

Another embodiment of the present invention (Embodiment PD19) is a compound of Formula IXa-P as defined in Embodiment PD18; and provided that when Q is —N=C($R^4$)—, then $R^4$ is H.

Another embodiment of the present invention (Embodiment PD20) is a compound of Formula IXb-P:

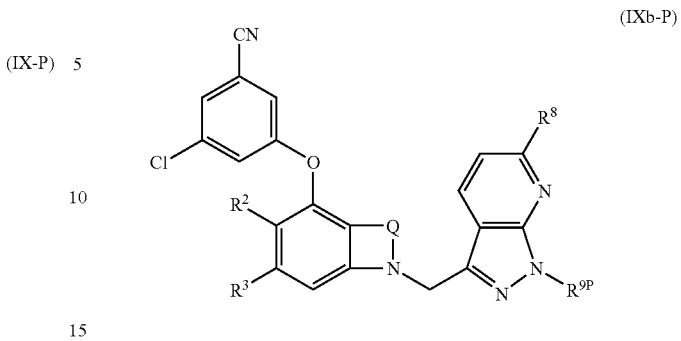

(IXb-P)

wherein Q, $R^2$, $R^3$, $R^4$ and $R^8$ are as defined in Class C14 set forth above; and $R^{9P}$ is as defined in Embodiment PD2.

Another embodiment of the present invention (Embodiment PD21) is a compound of Formula IXb-P as defined in Embodiment PD20; and provided that when Q is —N=C($R^4$)—, then $R^4$ is H.

Another embodiment of the present invention (Embodiment PD22) is a compound selected from the group consisting of:

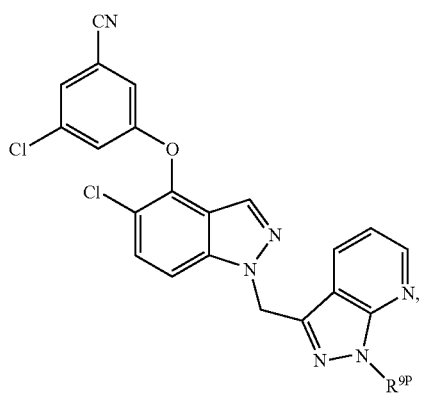

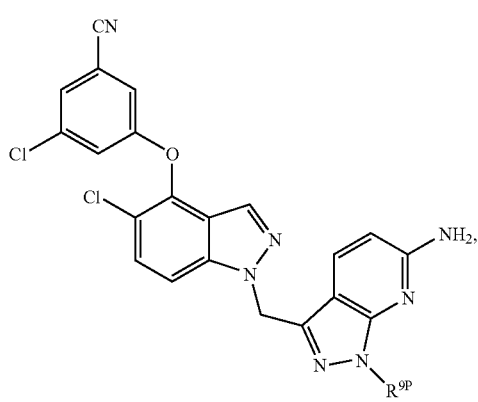

-continued
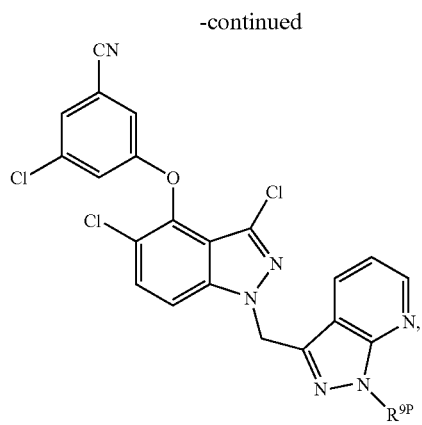
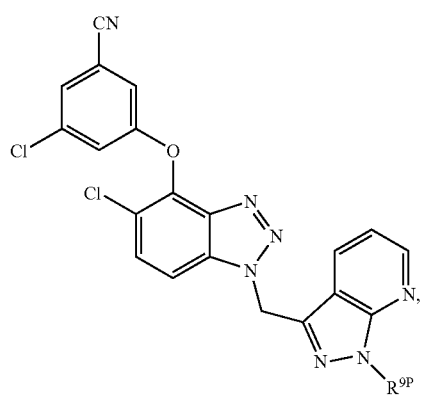
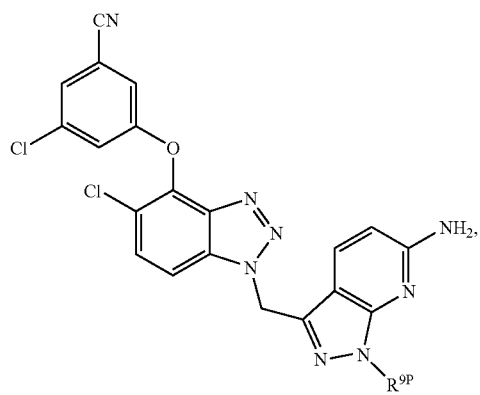
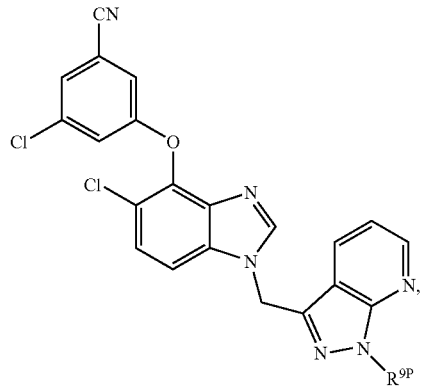
-continued
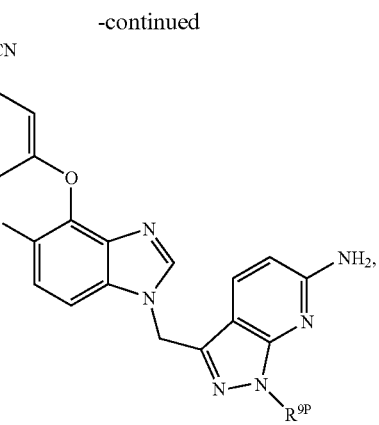
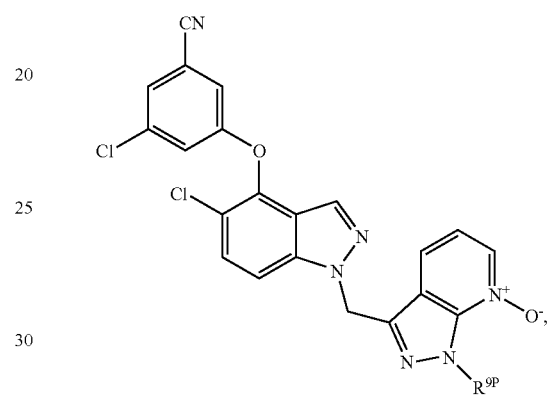
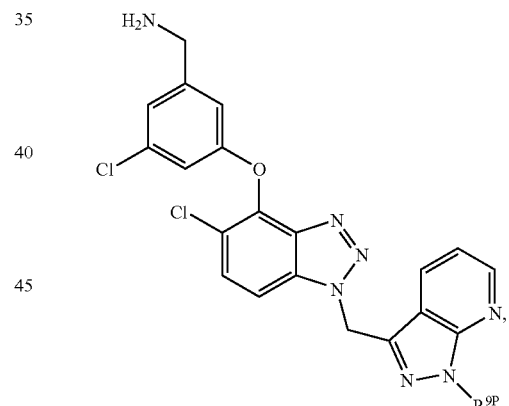
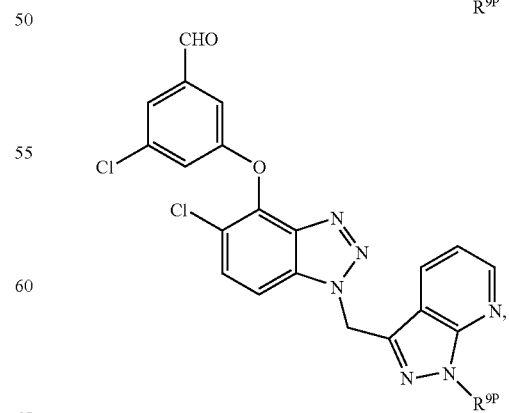

-continued
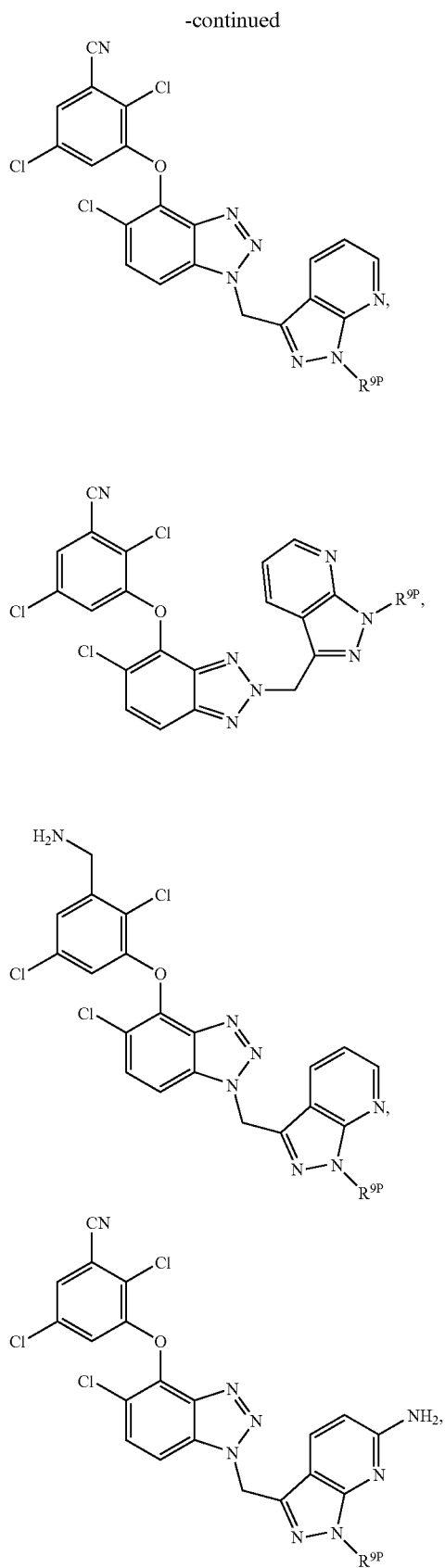
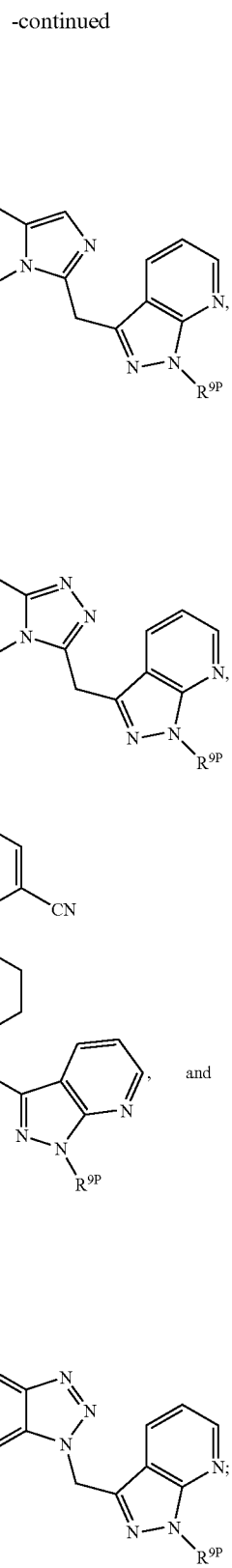
wherein $R^{9P}$ is as defined in Embodiment PD2.
Another embodiment of the present invention (Embodiment PD23) is a compound as defined in any one of Embodiments PD2 to PD22, wherein $R^{9P}$ is $PO(OH)O^-.M^+$; $PO(O^-)_2.2M^+$; $PO(O^-)_2.M^{2+}$; or an acid salt of:

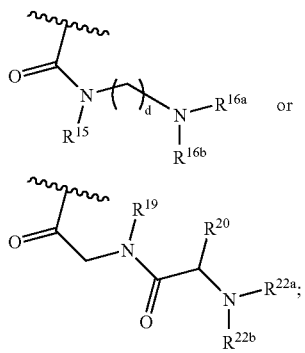

$M^+$ is a pharmaceutically acceptable monovalent counterion;

$M^{2+}$ is a pharmaceutically acceptable divalent counterion;

$R^{15}$ is H or $C_{1-4}$ alkyl;

$R^{16a}$ and $R^{16b}$ are each independently H or $C_{1-4}$ alkyl;

$R^{19}$ is H or $C_{1-4}$ alkyl;

$R^{20}$ is H or $C_{1-4}$ alkyl;

$R^{22a}$ and $R^{22b}$ are each independently H or $C_{1-4}$ alkyl; and d is an integer equal to 2, 3, or 4.

Another embodiment of the present invention (Embodiment PD24) is a compound as defined in any one of Embodiments PD2 to PD22, wherein $R^{9P}$ is an acid salt of:

A class of the preceding embodiment (Class C1-PD24) includes compounds as defined in Embodiment PD24, wherein the acid salt in the definition of $R^{9P}$ is a hydrochloride salt.

Another embodiment of the present invention (Embodiment PD25) is a compound selected from the group consisting of:

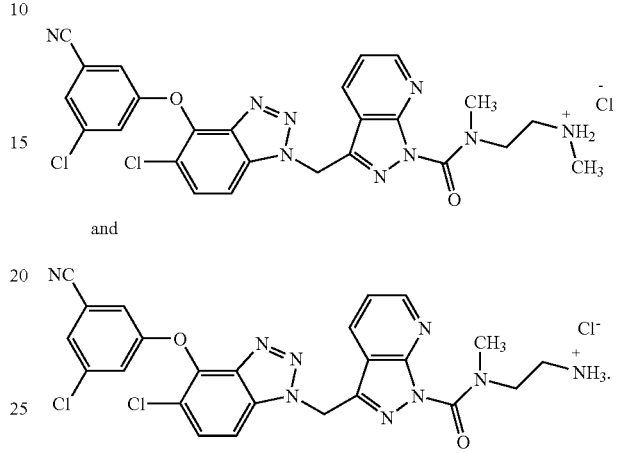

Pharmaceutically acceptable monovalent counterions ($M^+$) suitable for use in the prodrugs of the invention described in the foregoing embodiments include $NH_4^+$, alkali metal cations (e.g., $Na^+$ or $K^+$), and cations from alkylamines, hydroxyalkylamines (e.g., tris(hydroxymethyl)methylamine), choline, lysine, arginine, histidine, and N-methyl-D-glucamine. Suitable divalent counterions ($M^{2+}$) include the cations of alkaline earth metals such as $Mg^{2+}$ and $Ca^{2+}$. Additional pharmaceutically acceptable salts of basic drugs (pharmaceutically acceptable monovalent and divalent counterions) are described in P. L. Gould, *Int. J. Pharm.* 1986, vol. 33 pp. 201-217 and S. M. Berge et al., *J. Pharm. Sci.,* 1977, vol. 66, pp. 1-19.

Acid salts suitable for use in the prodrugs of the invention described in the foregoing embodiments include the salts of organic and inorganic acids. Suitable salts of inorganic acids include the salts of hydrochloric acid, sulfuric acid, alkali metal bisulfates (e.g., $KHSO_4$), and the like. Suitable salts of organic acids include the salts of carboxylic acids and sulfonic acids, such as alkylcarboxylic acids (e.g., acetic acid, propanoic acid, butyric acid, etc.), fluoroalkylcarboxlic acids (e.g., trifluoroacetic acid), arylcarboxylic acids (benzoic acid), alkylsulfonic acids (e.g., ethylsulfonic acid), fluoroalkylsulfonic acids (e.g., trifluoromethylsulfonic acid), and arylsulfonic acids (e.g., benzenesulfonic acid or toluenesulfonic acid).

While not wishing to be bound by any particular theory, it is believed that the compounds set forth in Embodiments PD2 to PD25 act as prodrugs, wherein the compound is relatively stable at low pH (e.g., pH=1 to 3) but will convert by hydrolysis or cyclization to its free base at physiological pH (e.g., a pH of greater than about 7), thereby releasing the active substance in vivo. This reaction is exemplified as follows for a hydrochloride salt:

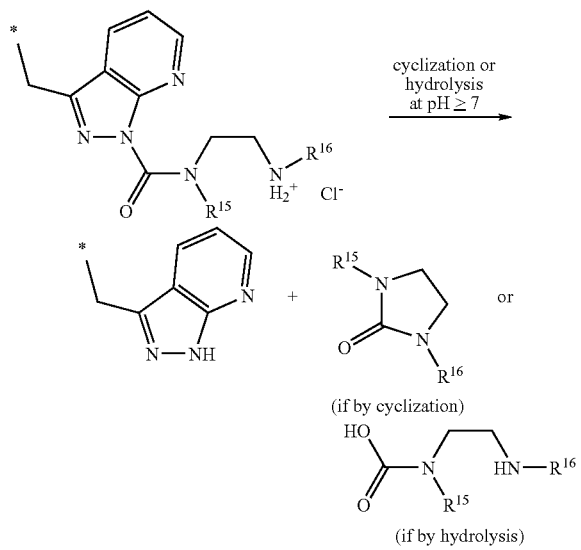

Other embodiments of the present invention include the following:

(a) A pharmaceutical composition comprising an effective amount of a compound of Formula I as defined above, or a prodrug or pharmaceutically acceptable salt thereof, and a pharmaceutically acceptable carrier.

(b) A pharmaceutical composition which comprises the product prepared by combining (e.g., mixing) an effective amount of a compound of Formula I as defined above, or a prodrug or pharmaceutically acceptable salt thereof, and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, HIV reverse transcriptase inhibitors other than a compound of Formula I, HIV integrase inhibitors, HIV fusion inhibitors, and HIV entry inhibitors.

(e) A combination which is (i) a compound of Formula I as defined above, or a prodrug or pharmaceutically acceptable salt thereof, and (ii) an anti-HIV agent selected from the group consisting of HIV antiviral agents, immunomodulators, and anti-infective agents; wherein Compound I and the anti-HIV agent are each employed in an amount that renders the combination effective for inhibition of HIV reverse transcriptase, for treatment or prophylaxis of infection by HIV, or for treatment, prophylaxis of, or delay in the onset or progression of AIDS.

(f) The combination of (e), wherein the anti-HIV agent is an antiviral selected from the group consisting of HIV protease inhibitors, HIV reverse transcriptase inhibitors other than a compound of Formula I, HIV integrase inhibitors, HIV fusion inhibitors, and HIV entry inhibitors.

(g) A method for the inhibition of HIV reverse transcriptase in a subject in need thereof which comprises administering to the subject an effective amount of a compound of Formula I or a prodrug or pharmaceutically acceptable salt thereof.

(h) A method of the prophylaxis or treatment of infection by HIV (e.g., HIV-1) in a subject in need thereof which comprises administering to the subject an effective amount of a compound of Formula I or a prodrug or pharmaceutically acceptable salt thereof.

(i) The method of (h), wherein the compound of Formula I is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, and HIV entry inhibitors.

(j) A method for the prophylaxis, treatment or delay in the onset or progression of AIDS in a subject in need thereof which comprises administering to the subject an effective amount of a compound of Formula I or a prodrug or pharmaceutically acceptable salt thereof.

(k) The method of (j), wherein the compound is administered in combination with an effective amount of at least one other HIV antiviral other than a compound of Formula I, selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, and HIV entry inhibitors.

(l) A method for the inhibition of HIV reverse transcriptase in a subject in need thereof which comprises administering to the subject the pharmaceutical composition of (a), (b), (c) or (d) or the combination of (e) or (f).

(m) A method for the prophylaxis or treatment of infection by HIV (e.g., HIV-1) in a subject in need thereof which comprises administering to the subject the pharmaceutical composition of (a), (b), (c) or (d) or the combination of (e) or (f).

(n) A method for the prophylaxis, treatment, or delay in the onset or progression of AIDS in a subject in need thereof which comprises administering to the subject the pharmaceutical composition of (a), (b), (c) or (d) or the combination of (e) or (f).

The present invention also includes a compound of Formula I, or a prodrug or pharmaceutically acceptable salt thereof, (i) for use in, (ii) for use as a medicament for, or (iii) for use in the preparation of a medicament for: (a) therapy (e.g., of the human body), (b) medicine, (c) inhibition of HIV reverse transcriptase, (d) treatment or prophylaxis of infection by HIV, or (e) treatment, prophylaxis of, or delay in the onset or progression of AIDS. In these uses, the compounds of the present invention can optionally be employed in combination with one or more anti-HIV agents selected from HIV antiviral agents, anti-infective agents, and immunomodulators.

Additional embodiments of the invention include the pharmaceutical compositions, combinations and methods set forth in (a)-(n) above and the uses (i)(a)-(e) through (iii)(a)-(e) set forth in the preceding paragraph, wherein the compound of the present invention employed therein is a compound of one of the embodiments, aspects, classes or subclasses described above. In all of these embodiments etc., the compound may optionally be used in the form of a prodrug or pharmaceutically acceptable salt.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or its prodrug or salt and a pharmaceutically acceptable carrier and optionally one or more excipients, it is understood that the term "substantially pure" is in reference to a compound of Formula I or its prodrug or salt per se.

Still additional embodiments of the present invention include the pharmaceutical compositions, combinations and methods set forth in (a)-(n) above and the uses (i)(a)-(e) through (iii)(a)-(e) set forth above, wherein the HIV of interest is HIV-1. Thus, for example, in the pharmaceutical composition (d), the compound of Formula I is employed in an amount effective against HIV-1 and the anti-HIV agent is an HIV-1 antiviral selected from the group consisting of HIV-1 protease inhibitors, HIV-1 reverse transcriptase inhibitors other than a compound of Formula I, HIV-1 integrase inhibitors, HIV-1 fusion inhibitors and HIV-1 entry inhibitors.

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and isopropyl, ethyl and methyl.

The term "alkenyl" refers to a monovalent straight or branched chain aliphatic hydrocarbon radical containing one carbon-carbon double bond and having a number of carbon atoms in the specified range. Thus, for example, "$C_2$-$C_6$ alkenyl" (or "$C_{2-6}$ alkenyl") refers to all of the hexenyl and pentenyl isomers as well as 1-butenyl, 2-butenyl, 3-butenyl, isobutenyl, 1-propenyl, 2-propenyl, and ethenyl (or vinyl). A class of alkenyls of interest with respect to the invention are alkenyls of formula —CH═CH—$(CH_2)_{1-3}CH_3$.

The term "alkynyl" refers to a monovalent straight or branched chain aliphatic hydrocarbon radical containing one carbon-carbon triple bond and having a number of carbon atoms in the specified range. Thus, for example, "$C_2$-$C_6$ alkynyl" (or "$C_{2-6}$ alkynyl") refers to all of the hexynyl and pentynyl isomers as well as 1-butynyl, 2-butynyl, 3-butynyl, 1-propynyl, 2-propynyl, and ethynyl.

The term "alkylene" refers to any divalent linear or branched chain aliphatic hydrocarbon radical having a number of carbon atoms in the specified range. Thus, for example, "—$C_{1-6}$ alkylene-" refers to any of the $C_1$ to $C_6$ linear or branched alkylenes, and "—$C_{1-4}$ alkylene-" refers to any of the $C_1$ to $C_4$ linear or branched alkylenes. A class of alkylenes of interest with respect to the invention is —$(CH_2)_{1-6}$—, and sub-classes of particular interest include —$(CH_2)_{1-4}$—, —$(CH_2)_{2-4}$—, —$(CH_2)_{1-3}$—, —$(CH_2)_{2-3}$—, —$(CH_2)_{1-2}$—, and —$CH_2$—. Another sub-class of interest is an alkylene selected from the group consisting of —$CH_2$—, —CH($CH_3$)—, and —C($CH_3$)$_2$—.

The term "cycloalkyl" refers to any monocyclic ring of an alkane having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.). A fluoroalkyl of particular interest is $CF_3$.

The term "C(O)" refers to carbonyl. The terms "S(O)$_2$" and "SO$_2$" each refer to sulfonyl. The term "S(O)" refers to sulfinyl.

The term "contain" in the proviso that "no more than two of V, W, Y and Z contain N" means that no more than two of V, W, Y and Z provide a ring nitrogen in ring A. It is understood that the substituents $R^{11}$ in $N(R^{11})$ and $R^{12}$ in $N(R^{12})$ can contain N.

An asterisk ("*") as the end of an open bond in a chemical group denotes the point of attachment of the group to the rest of the compound.

The term "aryl" refers to (i) phenyl, (ii) 9- or 10-membered bicyclic, fused carbocylic ring systems in which at least one ring is aromatic, and (iii) 11- to 14-membered tricyclic, fused carbocyclic ring systems in which at least one ring is aromatic. Suitable aryls include, for example, phenyl, naphthyl, tetrahydronaphthyl (tetralinyl), indenyl, anthracenyl, and fluorenyl. A class of aryls of interest with respect to the invention is phenyl and napthyl. An aryl of particular interest is phenyl.

The term "heteroaryl" refers to (i) a 5- or 6-membered heteroaromatic ring containing from 1 to 4 heteroatoms independently selected from N, O and S, wherein each N is optionally in the form of an oxide, (ii) a 9- or 10-membered bicyclic fused ring system, or (iii) an 11- to 16-membered tricyclic fused ring system, wherein the fused ring system of (ii) or (iii) contains from 1 to 6 heteroatoms independently selected from N, O and S, wherein each ring in the fused ring system contains zero, one or more than one heteroatom, at least one ring is aromatic, each N is optionally in the form of an oxide, and each S in a ring which is not aromatic is optionally S(O) or S(O)$_2$. Suitable 5- and 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl (e.g., benzo-1,3-dioxolyl;

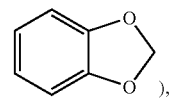

), benzopiperidinyl, benzisoxazolyl, benzoxazolyl, chromanyl, isochromanyl, benzothienyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl (i.e.,

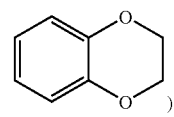

).

Suitable tricyclic heteroaryls include, for example, xanthyl and carbazolyl.

Examples of 4- to 7-membered, saturated heterocyclic rings within the scope of this invention (see HetF) include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, mono-unsaturated heterocyclic rings within the scope of this invention (see HetF) include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings and ring systems suitable for use in the present invention are not limited to those listed in the preceding paragraphs. These rings and ring systems are merely representative.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. As another example, an aryl or heteroaryl described as optionally substituted with "from 1 to 6 substituents" is intended to include as aspects thereof, an aryl or heteroaryl substituted with 1 to 6 substituents, 2 to 6 substituents, 3 to 6 substituents, 4 to 6 substituents, 5 to 6 substituents, 6 substituents, 1 to 5 substituents, 2 to 5 substituents, 3 to 5 substituents, 4 to 5 substituents, 5 substituents, 1 to 4 substituents, 2 to 4 substituents, 3 to 4 substituents, 4 substituents, 1 to 3 substituents, 2 to 3 substituents, 3 substituents, 1 to 2 substituents, 2 substituents, and 1 substituent.

When any variable (e.g., $R^A$ or $R^B$) occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., cycloalkyl, aryl, or heteroaryl) provided such ring substitution is chemically allowed and results in a stable compound.

As a result of the selection of substituents and substituent patterns, certain compounds of the present invention can exhibit tautomerism such as keto-enol tautomerism. All tautomeric forms of these compounds, whether present individually or in mixtures, are within the scope of the present invention. For example, in compounds of the present invention where a hydroxy (—OH) substituent is permitted on a heteroaromatic ring and keto-enol tautomerism is possible, it is understood that the substituent might in fact be present, in whole or in part, in the keto form.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I.

As a result of the selection of substituents and substituent patterns, certain compounds of the present invention can have asymmetric centers and can occur as mixtures of stereoisomers, or as individual diastereomers, or enantiomers. All isomeric forms of these compounds, whether individually or in mixtures, are within the scope of the present invention.

The methods of the present invention involve the use of compounds of the present invention in the inhibition of HIV reverse transcriptase (e.g., wild type HIV-1 and/or mutant strains thereof), the prophylaxis or treatment of infection by human immunodeficiency virus (HIV) and the prophylaxis, treatment or delay in the onset or progression of consequent pathological conditions such as AIDS. Prophylaxis of AIDS, treating AIDS, delaying the onset or progression of AIDS, or treating or prophylaxis of infection by HIV is defined as including, but not limited to, treatment of a wide range of states of HIV infection: AIDS, ARC (AIDS related complex), both symptomatic and asymptomatic, and actual or potential exposure to HIV. For example, the present invention can be employed to treat infection by HIV after suspected past exposure to HIV by such means as blood transfusion, exchange of body fluids, bites, accidental needle stick, or exposure to patient blood during surgery. As another example, the present invention can also be employed to prevent transmission of HIV from a pregnant female infected with HIV to her unborn child or from an HIV-infected female who is nursing (i.e., breast feeding) a child to the child via administration of an effective amount of Compound I or a pharmaceutically acceptable salt thereof.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. When compounds employed in the present invention carry an acidic moiety (e.g., —COOH or a phenolic group), suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of Formula I mean providing the compound or a prodrug of the compound to the individual in need of treatment or prophylaxis. When a compound or a prodrug thereof is provided in combination with one or more other active agents (e.g., antiviral agents useful for treating or prophylaxis of HIV infection or AIDS), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV reverse transcriptase (wild type and/or mutant strains thereof) and thereby elicit the response being sought (i.e., an "inhibition effective amount"). When the active compound (i.e., active ingredient) is administered as the salt, references to the amount of active ingredient are to the free form (i.e., the non-salt form) of the compound.

In the method of the present invention (i.e., inhibiting HIV reverse transcriptase, treating or prophylaxis of HIV infection or treating, prophylaxis of, or delaying the onset or progression of AIDS), the compounds of Formula I, optionally in the form of a salt or a prodrug, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18$^{th}$ edition, edited by A. R. Gennaro, Mack Publishing Co., 1990 and in *Remington—The Science and Practice of Pharmacy*, 21st edition, Lippincott Williams & Wilkins, 2005.

The compounds of Formula I can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In one embodiment, a compound of Formula I such as the compound of Example 1 can be administered to adult humans orally in the form of a tablet or capsule containing the compound in an amount in a range of from about 40 mg to about 900 mg, wherein the tablet or capsule is administered once per day or twice per day. In another embodiment, a compound of Formula I such as the compound of Example 1 can be administered to adult humans orally in the form of a tablet or capsule containing the compound in an amount in a range of from about 40 mg to about 320 mg, wherein the tablet or capsule is administered once per day or twice per day.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS, such as those disclosed in Table 1 of WO 01/38332 or in the Table in WO 02/30930. Suitable HIV antivirals for use in combination with the compounds of the present invention include, for example, those listed in Table A as follows:

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |

TABLE A-continued

| Name | Type |
| --- | --- |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| efavirenz, EFV, Sustiva ®, Stocrin ® | nnRTI |
| efavirenz + emtricitabine + tenofovir DF, Atripla ® | nnRTI + nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., abacavir sulfate, indinavir sulfate, atazanavir sulfate, nelfinavir mesylate.

It is understood that the scope of combinations of the compounds of this invention with anti-HIV agents is not limited to the HIV antivirals listed in Table A and/or listed in the above-referenced Tables in WO 01/38332 and WO 02/30930, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57$^{th}$ edition (2003), the 58$^{th}$ edition (2004), the 59$^{th}$ edition (2005), and subsequent editions thereof. The dosage ranges for a compound of the invention in these combinations are the same as those set forth above.

Abbreviations employed herein include the following:

ACN=acetonitrile; AIDS=acquired immunodeficiency syndrome; BOC or Boc=t-butyloxycarbonyl; (BOC)$_2$O (or BOC$_2$O)=di-t-butyl carbonate; Bn-p-OMe=p-methoxybenzyl; BrdUTP=bromodeoxyuridine triphosphate; n-Bu=n-butyl; t-Bu=t-butyl; CHAPS=3-[(3-cholamidopropyl)-dimethylammonio]-1-propane-sulfonate; DCE=1,2-dichloroethane; DCM=dichloromethane; DMAP=4-dimethylaminopyridine; DMF=dimethylformamide; DMPU=1,3-dimethyl-3,4,5,6-tetrahydro-2(1H)-pyrimidinone (or N,N'-dimethylpropyleneurea); DMSO=dimethylsulfoxide; dNTP=deoxynucleoside triphosphate; DPPA=diphenylphosphoryl azide; EDC=1-ethyl-3-(3-dimethylaminopropyl)carbodiimide; EGTA=ethylene glycol bis(2-aminoethyl ether)-N,N,N',N'-tetraacetic acid; Et=ethyl; EtOAc=ethyl acetate; EtOH=ethanol; HOAT=1-hydroxy-7-azabenzotriazole; HPMCAS-LF=hydroxypropylmethylcellulose acetate succinate-low fine (powder); HPLC=high-performance liquid chromatography; HRMS=high resolution mass spectroscopy; IPA=isopropyl alcohol; LAH=lithium aluminum hydride; LC=liquid chromatography; LDA=lithium diisopropylamide; LRMS=low resolution mass spectroscopy; mCPBA=meta-chloroperbenzoic acid; MeOH=methanol; NBS=N-bromosuccinimide; NMP=N-methylpyrrolidinone; NMR=nuclear magnetic resonance; Ph=phenyl; PMB=para-methoxybenzyl; TEA=triethylamine; TFA=trifluoroacetic acid; THF=tetrahydrofuran; Tos=tosyl.

The compounds of the present invention can be readily prepared according to the following reaction schemes and examples, or modifications thereof, using readily obtainable starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Scheme A depicts a general method suitable for the preparation of compounds of the invention with a nitrogen atom in ring B adjacent to a carbon shared with ring A, wherein the fused bicyclic A-1 is coupled with 1-Boc-1H-pyrazolo[3,4-b]pyridin-3-yl methylene bromide A-2 in the presence of a base (e.g., an alkali metal carbonate such as CsCO$_3$) and then the Boc protective group is removed by treating the coupled product with a suitable acid (e.g., TFA) to afford A-3. An alkyl group can be introduced at the 1-position of the pyrazolopyridinyl group by reaction of A-3 with an alkyl halide.

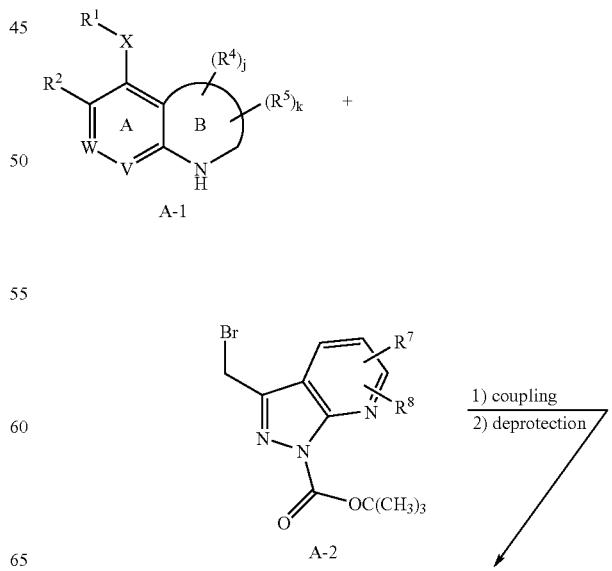

-continued

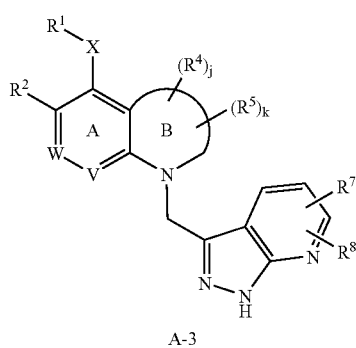

A-3

Representative examples of starting substrate A-1 include the following:

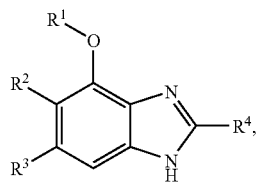

A-1a

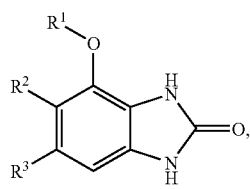

A-1b

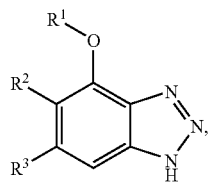

A-1c

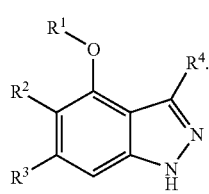

A-1d

Substrates of Formula A-1a can be prepared in accordance with Scheme B:

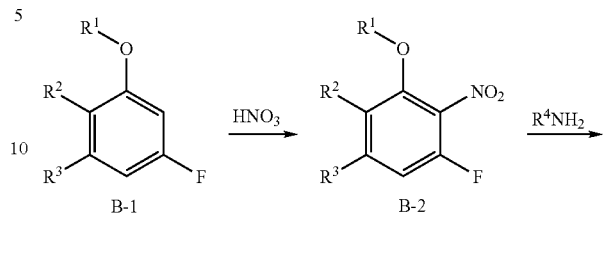

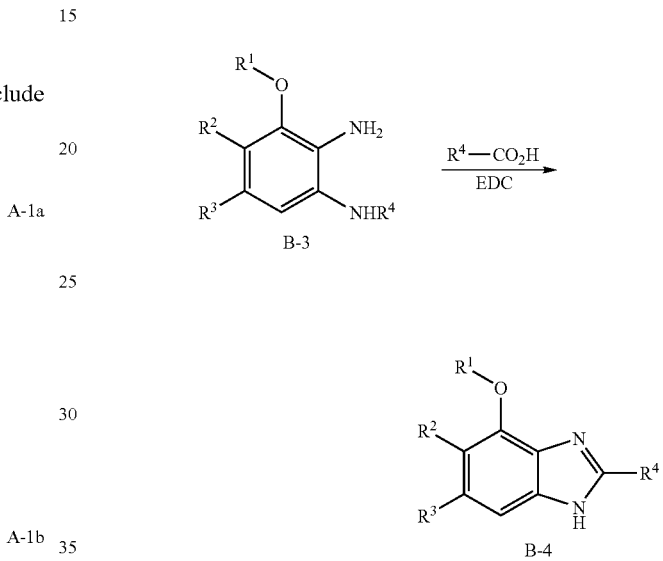

Substrates of Formula A-1b can be prepared in accordance with Scheme B':

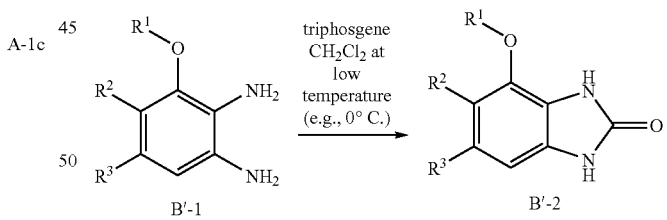

Representative methods for preparing reactants of formula A-1 and A-2 are further described in the examples below.

Scheme C depicts the preparation of benzotriazolyl compounds of the present invention, wherein the nitro group on the 2-amino-nitrobenzene derivative C-1 can be reduced to the corresponding dianiline C-2 through catalytic hydrogenation or by the action of tin II chloride. The dianiline can undergo cyclization to the corresponding triazole C-3 upon diazotization. Alkylation of the triazole can be accomplished through reaction with a suitable electrophile such as $R^6$ (which may require protection) in the presence of a base to afford either C-4 or C-6.

Scheme C

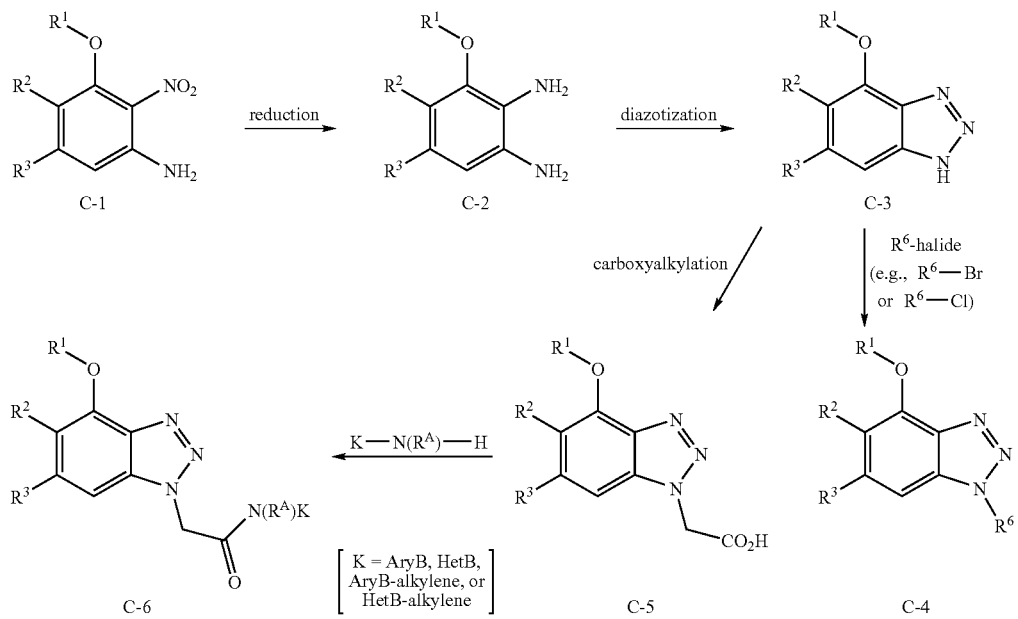

Scheme D depicts the preparation of pyrazolopyridine and imidazopyridine compounds of the invention, wherein a hydrazino or aminomethylpyridine D-1 can be acylated with the requisite carboxylic acid to provide acylate D-2, which can be cyclized dehydratively using phosphorous oxychloride to afford D-3.

Scheme D

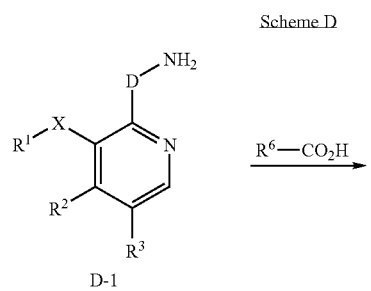

-continued

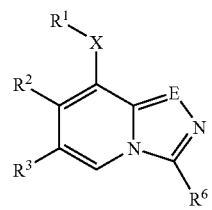

D = $CH_2$ or NH
E = CH or N

Scheme E depicts the preparation of benzopyrazolyl and indazolyl compounds of the invention wherein the arylboronic acid E-1 can be coupled with a suitable phenol or aniline (i.e., $R^1XH$) in the presence of a copper carboxylate (e.g., copper acetate) to provide the aryl ether or aryl amine E-2, which can be deprotonated and acylated to provide aldehyde or ketone E-3. The aldehyde or ketone can be further reacted with hydrazine to afford the corresponding benzopyrazole or indazole penultimate E-4, which can be alkylated with a suitable $R^6$ halide ($R^6$ may require protection) to provide the compound of the invention E-5.

Scheme E

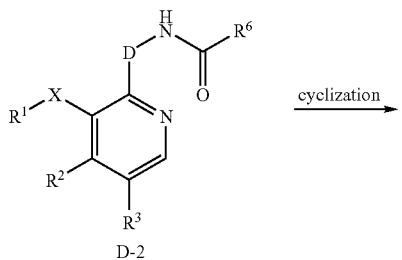

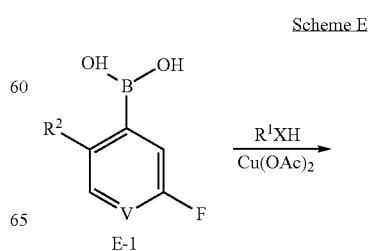

-continued

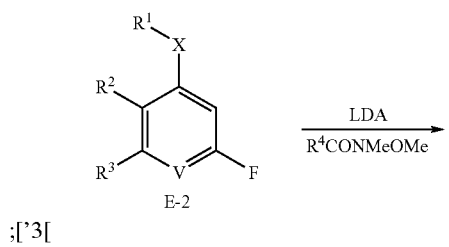

[3'];

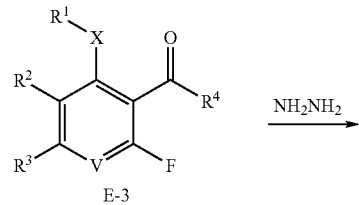

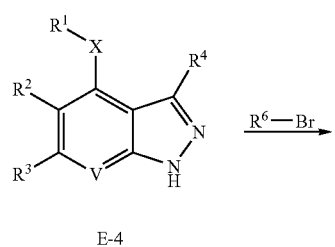

[X = O or N(R^A)]

Scheme F depicts another route for preparing compounds of the invention, wherein the aryl ether or aryl amine E-2 can be deprotonated and quenched with methylchloroformate to provide the ester F-1. Nucleophilic displacement of the fluorine in F-1 with a suitably protected amine (exemplified by PMB in Scheme F) can provide F-2, which can be converted to the corresponding diamine F-3 through a Curtius rearrangement. Following deprotection (e.g., treatment of the PMB with acid), the diamine can be converted to a variety of heterocycles including, for example, the triazole F-4 shown in Scheme F.

Scheme F

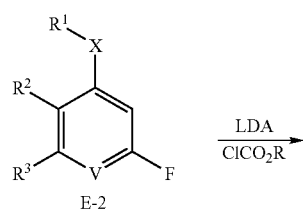

-continued

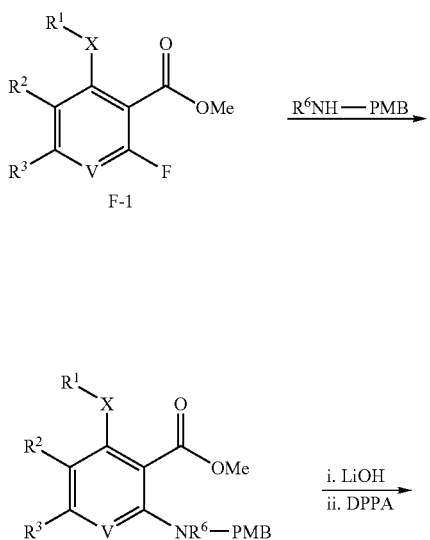

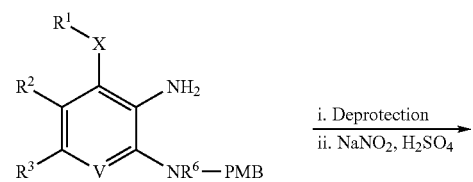

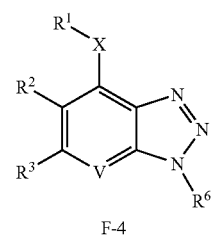

Scheme G depicts a representative preparation of a pro-drug of the present invention, wherein the benzotriazolyl compound of the present invention G-1 can be treated with a Boc-protected amine in the presence of a phosgene to afford acylated amine G-2, which can then be deprotected by treatment with a suitable acid (e.g., HCl or TFA) to provide desired pro-drug G-3.

Scheme G

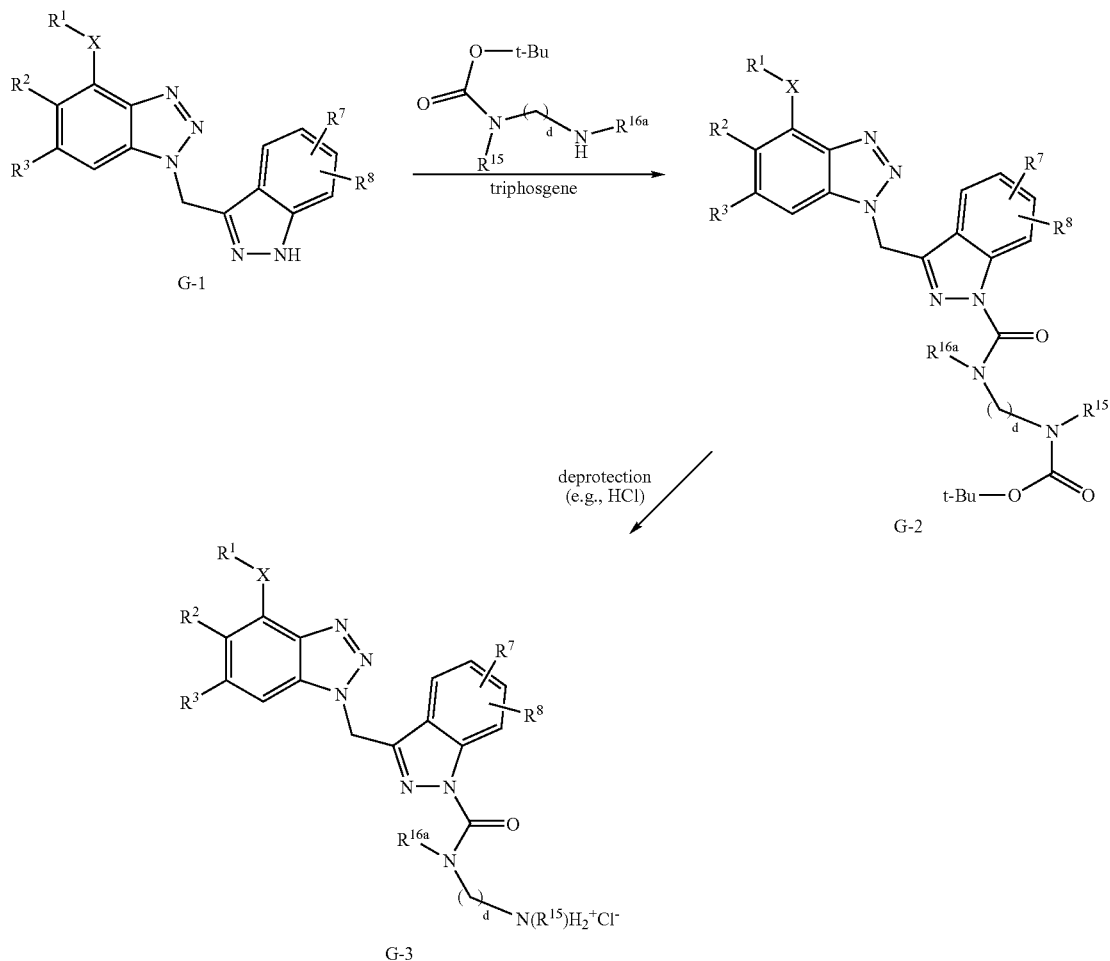

In the methods for preparing compounds of the present invention set forth in the foregoing schemes, functional groups in various moieties and substituents (e.g., $R^6$ in Scheme C, $R^6$ in Scheme E, $R^6$ in Scheme F, as well as other groups explicitly or implicitly referred to in the foregoing schemes) may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protective groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 3$^{rd}$ edition, 1999, and 2$^{nd}$ edition, 1991. The protecting groups may be removed at a convenient subsequent stage using methods known in the art. Alternatively the interfering group can be introduced into the molecule subsequent to the reaction step of concern.

The following examples serve only to illustrate the invention and its practice. The examples are not to be construed as limitations on the scope or spirit of the invention. References in the following examples to "room temperature" means a temperature of from about 20° C. to about 25° C.

Intermediate 1

1-(tert-Butyl)-3-(bromomethyl)-1H-pyrazolo[3,4-b]pyridine-1-carboxylate

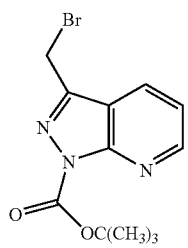

Intermediate I was prepared in accordance with the procedure described in Henke et al., *J. Med. Chem.* 1997, 40: p. 2706. More particularly:

Step 1: 1-(2-fluoropyridine-3-yl)ethanone

A solution of 3.13 mL (30.90 mmol) of freshly distilled diisopropylamine in 10 mL of anhydrous THF under nitrogen cooled to −78° C. was treated dropwise with 19.31 mL (30.90 mmol) of a 1.6 M solution of n-BuLi in hexanes. The resulting solution was stirred at −78° C. for approximately 20 minutes, and was briefly (5-10 minutes) warmed to −40° C., then recooled to −78° C. At 30 minutes post addition, 3.00 g (30.90 mmol) of 2-fluoropyridine was added dropwise to the reaction. The resulting solution was stirred at −78° C. for 30 minutes. The reaction was treated dropwise with a solution of 3.16 mL (30.90 mmol) of the Weinreb amide (i.e., N-methoxy-n-methylacetamide) in 30 mL of THF. The resulting solution was stirred 18 hours, allowing the bath to slowly evaporate and the reaction temperature to rise to room temperature. The reaction was treated with 5 mL of 1N HCl, and was concentrated to remove most of the THF. The residue was extracted twice with EtOAc, and the combined extracts were washed with 1N HCl, saturated aqueous $NaHCO_3$ solution, and brine, and were dried over anhydrous $MgSO_4$. Filtration and concentration of the filtrate provided a crude orange oil, which was purified by flash chromatography over silica gel with 3:1 hexanes/EtOAc to provide 1.10 g of the title product as an orange oil. $^1$H NMR ($CDCl_3$): δ 2.72 (s, 3H), 7.33 (m, 1H), 8.34 (m, 1H), 8.41 (m, 1H).

Step 2: 3-methyl-1H-pyrazolo[3,4-b]pyridine (36-2)

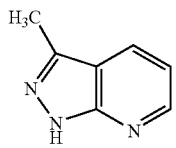

A stirred solution of 1.10 g (7.91 mmol) of 1-(2-fluoropyridine-3-yl)ethanone in 5 mL of ethylene glycol under nitrogen was treated with 265 μL (8.31 mmol) of hydrazine. This solution was stirred for 2 hours at room temperature and then heated at 165° C. for 1.5 hours. The solution was cooled to room temperature, poured into $CH_2Cl_2$ (25 mL), and extracted with $H_2O$ (2×50 mL). The organic portions were combined, dried ($MgSO_4$), filtered and concentrated in vacuo to give the title product as a fluffy off-white solid. $^1$H NMR ($CDCl_3$): δ 2.61 (s, 3H), 7.14 (m, 1H), 8.06 (dd, 1H), 8.58 (dd, 1H), 11.18 (br s, 1H).

Step 3: tert-butyl 3-methyl-1H-pyrazolo[3,4-b]pyridine-1-carboxylate

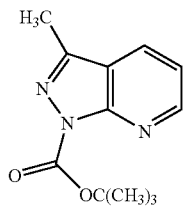

A stirred solution of 692 mg (5.20 mmol) of 3-methyl-1H-pyrazolo[3,4-b]pyridine in 25 mL of acetonitrile under nitrogen was cooled to 0° C. in an ice bath, and was treated with 635 mg (5.20 mmol) of DMAP and 761 μL (5.46 mmol) of triethylamine. A solution of 1.36 g (6.24 mmol) of $(BOC)_2O$ in 5 mL acetonitrile was then added dropwise using an addition funnel. Upon completion of addition, the ice bath was removed and the mixture was stirred for an additional 18 hours at room temperature. Solvent was removed in vacuo, and the residue was partitioned between EtOAc and $H_2O$. The organic layer was separated, dried ($MgSO_4$), filtered and concentrated in vacuo to an orange oil. This crude material was purified by flash chromatography over silica gel with 1:1 ethyl acetate/hexanes to give the title product as a clear oil. $^1$H NMR ($CDCl_3$): δ 1.74 (s, 9H), 2.60 (s, 3H), 7.29 (m, 1H), 8.02 (dd, 1H), 8.74 (dd, 1H).

Step 4: 1-(tert-butyl)-3-(bromomethyl)-1H-pyrazolo[3,4-b]pyridine-1-carboxylate

A stirred solution of 934 mg (4.00 mmol) of tert-butyl 3-methyl-1H-pyrazolo[3,4-b]pyridine-1-carboxylate in 10 mL of $CCl_4$ was heated to reflux, and then a mixture of 783 mg (4.40 mmol) of NBS and 97 mg (0.40 mmol) of benzoyl peroxide was added portion-wise over 5 minutes as a solid. The resulting solution was heated at reflux for 5 hours and then allowed to cool to room temperature. The reaction mixture was filtered through a pad of Celite to remove precipitated succinimide, and the filtrate was concentrated in vacuo. The crude residue was purified by flash chromatography over silica gel with 1:2 ethyl acetate/hexanes to the title product as a solid. $^1$H NMR ($CDCl_3$): δ 1.76 (s, 9H), 4.78 (s, 2H), 7.35 (q, 1H), 8.24 (dd, 1H), 8.77 (dd, 1H).

Intermediate 2

3-(Chloromethyl)-N,1-bis(4-methoxybenzyl)-1H-pyrazolo[3,4-b]pyridin-6-amine

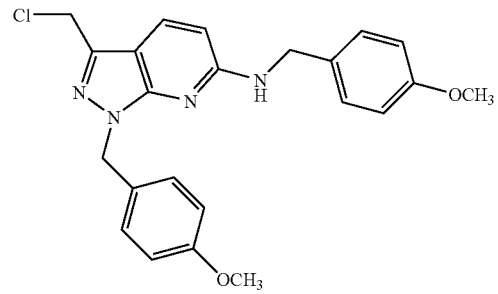

Step 1: tert-Butyl 6-fluoro-1-(4-methoxybenzyl)-1H-pyrazolo[3,4-b]pyridine-3-carboxylate

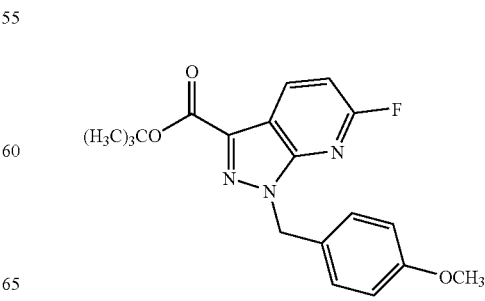

To a solution of tert-butyl 6-fluoro-1H-pyrazolo[3,4-b]pyridine-3-carboxylate (29.55 g, 125 mmol) in THF (300 mL) cooled in an ice bath was added KOtBu (13.98 g, 125 mmol) at such a rate as to maintain the temperature between 5-10° C., and then 4-methoxybenzyl bromide (18.2 mL, 125 mmol) was added. The resulting mixture was stirred in an ice bath for 1 hour and then stirred at room temperature for 18 hours. The resulting suspension was quenched with saturated aqueous NH$_4$Cl (200 mL) and then extracted with EtOAc (2×300 mL). The combined organic extracts were washed with brine, dried with MgSO$_4$ and the solvent removed in vacuo. The resulting residue was purified on a silica gel (1000 g) column (0-11% EtOAc/hexanes) to give the title compound. LRMS (M+1)=380.1

Step 2: tert-Butyl 1-(4-methoxybenzyl)-6-[(4-methoxybenzyl)amino]-1H-pyrazolo[3,4-b]pyridine-3-carboxylate

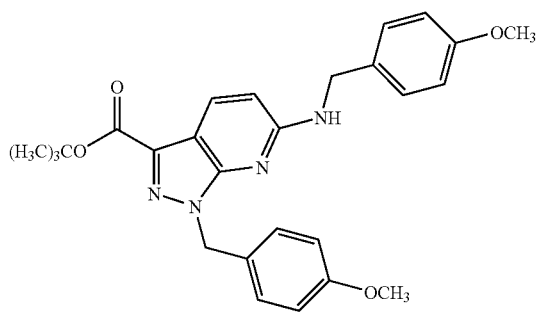

To a solution of tert-butyl 6-fluoro-1-(4-methoxybenzyl)-1H-pyrazolo[3,4-b]pyridine-3-carboxylate (2.55 g, 7.14 mmol) in NMP (30 mL) was added 4-methoxybenzylamine (2.80 mL, 21.41 mmol). The resulting mixture was then heated to 80° C. for 2 hours, after which the mixture was diluted with water (200 mL) and extracted with EtOAc (2×200 mL). The combined extracts were washed with water (100 mL), dried with MgSO$_4$, filtered, absorbed onto silica gel (17 g) and removed the solvent in vacuo. This solid was purified on silica gel (80 g) column (0-100% EtOAc/CH$_2$Cl$_2$ to give the title compound. LRMS (M+1)=474.0

Step 3: {1-(4-Methoxybenzyl)-6-[(4-methoxybenzyl)amino]-1H-pyrazolo[3,4-b]pyridin-3-yl}methanol

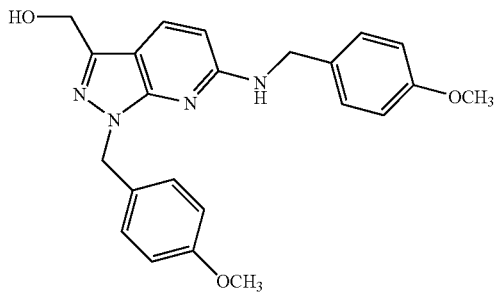

To a solution of tert-butyl 1-(4-methoxybenzyl)-6-[(4-methoxybenzyl)amino]-1H-pyrazolo[3,4-b]pyridine-3-carboxylate (2.65 g, 5.58 mmol) in 30 mL THF cooled in an ice bath was added a 2M solution of LiAlH$_4$ in THF (3.49 mL, 6.98 mmol). The resulting mixture was stirred cold for 20 minutes and then warmed to room temperature and then left at room temperature for 2.5 hours. The mixture was then diluted with THF (50 mL) and then treated sequentially with water (265 µL), 15% NaOH (265 µL) and water (795 µL) and then stirred for 30 minutes. The resulting suspension was filtered through diatomaceous earth and the resulting cake was rinsed with THF (50 mL). The combined filtrates were preabsorbed onto silica gel (15) and the solvent removed in vacuo. This solid was purified on silica gel (80 g) column (0-20% MeOH/CH$_2$Cl$_2$) to give the title compound. LRMS (M+1)=404.9

Step 4: 3-(Chloromethyl)-N,1-bis(4-methoxybenzyl)-1H-pyrazolo[3,4-b]pyridin-6-amine To a slurry of {1-(4-methoxybenzyl)-6-[(4-methoxybenzyl)amino]-1H-pyrazolo[3,4-b]pyridin-3-yl}methanol (1.49 g, 3.68 mmol) in chloroform (15 mL) cooled in an ice bath was added thionyl chloride (538 µL, 7.37 mmol). The resulting mixture was then allowed to warm to room temperature and left at room temperature for 30 minutes. The reaction was determined by LCMS monitoring not to be complete not complete, so the reaction mixture was re-cooled in an ice bath, treated with additional thionyl chloride (100 µL), and then stirred at room temperature for 30 minutes. The reaction mixture was then poured into aqueous NaHCO$_3$, extracted into CHCl$_3$ and the solvent removed in vacuo. This residue was purified on a silica gel (120 g) column (0-60% EtOAc/CHCl$_3$ to give the title compound. LRMS (M+1)=422.9

Example 1

3-Chloro-5-{[5-chloro-1-(1H-pyrazolo[3,4-b]pyridin-3-ylmethyl)-1H-indazol-4-yl]oxy}benzonitrile

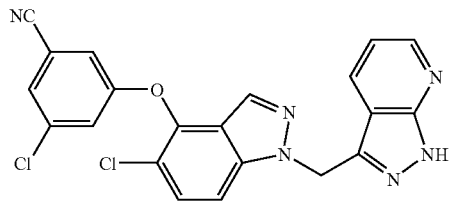

Step 1: 3-Bromo-5-chlorophenyl 2-chloro-5-fluorophenyl ether

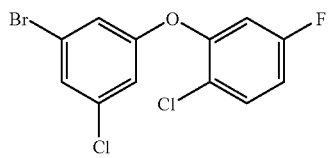

To a solution of 2-chloro-5-fluorophenol (82.3 g, 562 mmol) and 1-bromo-3-chloro-5-fluorobenzene (124 g, 590 mmol) in NMP (200 mL) was added potassium carbonate (155 g, 1.123 mol). The resulting mixture was then heated to 140° C. and maintained at 140° C. for hours, after which the mixture was poured into water (1500 mL) and extracted with EtOAc (2500+1500 mL). The combined extracts were washed with water and brine. This solution was concentrated on the rotary evaporator and the residue was distilled at high vacuum at 135-190° C. to give the title compound as a clear, colorless liquid. ¹H NMR (CDCl₃) δ 7.45 (dd, 1H, J=9.0 and 4.5 hz), 7.28 (dd, 1H, J=1.7 Hz), 7.26 (s, 1H), 7.00 (dd, 1 h, J=1.95 Hz), 6.92 (ddd, 1H, J=10.5, 7.6 and 2.7 Hz), 6.89 (dd, 1H, J=1.95 Hz).

Step 2: 2-(3-Bromo-5-chlorophenoxy)-3-chloro-6-fluorobenzaldehyde

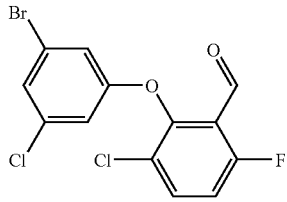

To a solution of 3-bromo-5-chlorophenyl 2-chloro-5-fluorophenyl ether (100 g, 298 mmol) in THF (300 mL) cooled to −78° C. over a dry ice/acetone bath was added 1.8M lithium diisopropylamide in hexanes/THF/ethylbenzene (174 mL, 313 mmol) over 10 min. The resulting mixture was stirred for 20 minutes and then treated with DMF (46.1 mL, 595 mmol). The DMF-treated mixture was then removed from the cooling bath and allowed to warm to room temperature and then left at room temperature for 1 hour. The reaction mixture was then quenched with water (1000 mL) and extracted with EtOAc (3×500 mL). The combined extracts were washed with water (500 mL), dried over MgSO₄, and concentrated in vacuo. This residue was purified on a silica gel column (0-40% CH₂Cl₂/hexanes) to give the title product. LRMS (M−18+1)=346.7

Step 3: 4-(3-Bromo-5-chlorophenoxy)-5-chloro-1H-indazole

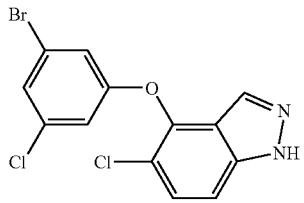

To a suspension of 2-(3-bromo-5-chlorophenoxy)-3-chloro-6-fluorobenzaldehyde (77.5 g, 213 mmol) in ethanol (120 mL) was added hydrazine hydrate (31 mL, 639 mmol). The resulting mixture was then heated at reflux for 4 days, after which the mixture was cooled to room temperature, diluted with water (100 mL) and the resulting solid was filtered. The solid was absorbed onto silica gel (300 g) and purified on a silica gel (1500 g) column (0-40% EtOAc/CH₂Cl₂) to give the title product as a white solid. LRMS (M+1)=358.8

Step 4: 3-Chloro-5-[(5-chloro-1H-indazol-4-yl)oxy]benzonitrile

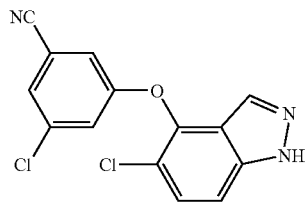

To a suspension of 4-(3-bromo-5-chlorophenoxy)-5-chloro-1H-indazole (40 g, 112 mmol) and zinc cyanide (15.74 g, 134 mmol) in DMF (400 mL) was added palladium tetrakis triphenylphosphine (38.7 g, 33.5 mmol) and heated to 90° C. for 1 hour. After this time, the reaction was cooled to room temperature and partitioned between saturated aq. NH₄Cl (500 mL), water (500 mL) and EtOAc (2×1000 mL). The combined extracts were dried over MgSO₄, absorbed onto silica gel (200 g) and the solvent removed in vacuo. This solid was purified on a silica gel (1000 g) column (0-10% EtOAc/CH₂Cl₂) to give the title compound as a white solid. LRMS (M+1)=303.9

Step 5: 3-Chloro-5-{[5-chloro-1-(1H-pyrazolo[3,4-b]pyridin-3-ylmethyl)-1H-indazol-4-yl]oxy}benzonitrile To a suspension of 3-chloro-5-[(5-chloro-1H-indazol-4-yl)oxy]benzonitrile (24 g, 79 mmol) and tert-butyl 3-(bromomethyl)-1H-pyrazolo[3,4-b]pyridine-1-carboxylate (=Intermediate 1; 24.63 g, 79 mmol) in DMF (150 mL) at 0° C. was added cesium carbonate (51.4 g, 158 mmol). The resulting mixture was allowed to warm to room temperature and then stirred at room temperature for 2 hours, after which the mixture was partitioned between water (1000 mL) and EtOAc (1000 mL). The organic extract was washed with water (1000 mL) and then with brine (200 mL), dried over MgSO₄ and the solvent removed in vacuo. This residue was purified on a silica gel (500 g) column (0-10% acetonitrile/CH₂Cl₂) to give the Boc-protected form of the title compound. This material was dissolved in TFA (50 mL) and allowed to stand at room temperature for 10 minutes, after which the solvent was removed in vacuo. The resulting solid was then preabsorbed onto silica gel (50 g) and purified on silica gel (330 g) column (10-30% acetonitrile/CH₂Cl₂) to give the title compound as a white solid.
¹H NMR (DMSO-d₆): δ 13.65 (s, 1H), 8.49 (d, J=4.6 Hz, 1H), 7.91 (d, J=8.3 Hz, 1H). 7.89 (s, 1H), 7.82 (d, J=8.8 Hz, 1H), 7.62 (d, J=8.6 Hz, 1H), 7.47 (m, 1H), 7.39 (m, 1H), 7.13 (dd, J=7.7 and 4.6 Hz, 1H), 6.05 (s, 2H) ppm. LRMS (M+1)=434.7

Example 1A

Alternative preparation of 3-chloro-5-{[5-chloro-1-(1H-pyrazolo[3,4-b]pyridin-3-ylmethyl)-1H-indazol-4-yl]oxy}benzonitrile Step 1: 3-Bromo-5-chlorophenyl 2-chloro-5-fluorophenyl ether A round bottom flask (100 L) was charged with K₂CO₃ (11.410 kg; 82.56 moles; 3.00 eqs.), DMSO (40 L), and 1-bromo-3-chloro-5-fluorobenzene (5.82 kg, 27.79 moles; 1.00 eq.). The resulting white slurry was degassed for 10 minutes using a subsurface stream of nitrogen, after which 2-chloro-5-fluorophenol (1.2 kg) was added through a dropping funnel. The reaction mixture was then heated to 150° C., and a second portion 2-chloro-5-fluorophenol (4.56 kg) was added in batches of about 0.5-0.6 kg batch over 7 hours. The mixture was then aged at 150° C. for 12 hours, and cooled to room temperature. About half of the mixture was transferred to an extractor (100 L) filled with water (30 L), extracted with heptane (45 L), and then washed with water (18 L). The other half of the mixture was worked up in the same manner. The combined organic layers were filtered through a silica pad (22 kg), washed with heptane (50 L), and concentrated on a rotavap with a bath temperature of 50° C.-60° C. to provide a clear colorless viscous oil that solidified after cooling to room temperature.

Step 2: 2-(3-Bromo-5-chlorophenoxy)-3-chloro-6-fluorobenzaldehyde

A round bottom flask was charged with diisopropylamine (1.336 kg, 13.20 moles; 1.2 eqs.) and THF (25 L), and the mixture cooled to −16° C. in a dry ice/acetone bath. A solution of n-butyl lithium (2.5 M; 12.65 moles; 1.17 eqs.) in hexane was added over 25 minutes, while keeping the temperature below 1° C., after which the mixture was aged 20 minutes and then cooled to below −70° C. 3-Bromo-5-chlorophenyl 2-chloro-5-fluorophenyl ether (3.638 kg; 10.8 moles; 1.0 eq.) in THF (4 L) was then added over 35 minutes. The reaction mixture was kept below −60° C. and aged for 1.5 hours, after which DMF (3.683 kg; 50.4 moles; 1.2 eq.) was added over 15 minutes. After aging the mixture a further 50 minutes, the reaction mixture was warmed to −20° C. and quenched with water (5 L). The mixture was then warmed to 15° C., transferred to an extractor (100 L) filled with water (20 L), and extracted with EtOAc (28 L). The organic layer was washed with water (22 L), 1N HCl (25 L), and brine (18 L), and then concentrated to 15 L. Heptane (25 L) was added to the concentrate, and the resulting solution was heated to 60° C. and then concentrated to 18 L as it was cooled to 11° C. The dark yellow suspension was filtered and washed with heptane (5 L), and dried overnight to provide the title product as a solid.

Step 3: 4-(3-Bromo-5-chlorophenoxy)-5-chloro-1H-indazole

A suspension of 2-(3-bromo-5-chlorophenoxy)-3-chloro-6-fluorobenzaldehyde fluorobenzaldehyde (4.5 kg; 12.36 moles; 1.0 eq.) in DMSO (18 L) was degassed, after which hydrazine monohydrate (6.192 kg; 123.7 moles; 10.0 eqs.) was added over 20 minutes at room temperature. The reaction solution was degassed again, stirred at room temperature for 15 minutes, heated to 73° C., and then aged for 16 hours. After the mixture was cooled to room temperature, isopropanol (15 L) and then water (40 L) were added, and the resulting mixture cooled to room temperature, filtered under pressure, and washed with isopropanol:water (1:2; 10 L), water (12 L), and heptane (12 L). The title product as a solid was obtained after drying at 30° C.-35° C. under vacuum for four days.

Step 4: 3-Chloro-5-[(5-chloro-1H-indazol-4-yl)oxy]benzonitrile

Bromine (154 g; 0.964 mole; 0.10 eq.) was added to a slurry of zinc (particle size <10 microns; 192 g; 2.940 moles; 0.30 eq.) in DMF (10 L) at room temperature. The resulting mixture was then stirred fast for 30 minutes while 4-(3-bromo-5-chlorophenoxy)-5-chloro-1H-indazole (3.508 kg; 9.798 moles; 1.00 eq., zinc cyanide (690 g; 5.879 moles; 0.60 eq.), triphenylphosphine (308 g; 1.176 moles; 0.12 eq.), palladium acetate (66 g; 0.294 mole; 0.03 eq.) and DMF (11 L) were added at room temperature. The reaction mixture was then degassed for 15 minutes using a subsurface stream of nitrogen, heated to 85° C., and then aged for 4.5 hours. The reaction mixture was then cooled to room temperature and stirred overnight. The reaction mixture was then diluted with THF (18 L) and heated to 50° C., after which aqueous EDTA.3Na (0.5M, 20 L) was added and the mixture aged at 50° C.-60° C. for 1 hour. The mixture was then filtered through solka floc and washed with THF (20 L), and the filtrate transferred to an extractor (100 L) filled with brine (15 L) and separated. The aqueous layer was extracted with EtOAc (15 L), and the combined organic layers were washed with a second portion of EDTA.3Na (0.5M, 20 L), then water (20 L), and then brine (15 L). The solution was treated with activated carbon (Darko KB), filtered through solka floc, concentrated to a slurry of less than 10 L, switched to toluene (6 L), concentrated to half volume, heated to 40° C., added heptane (6 L), and cooled below 25° C. The resulting slurry was filtered, washed with extra toleuene:heptane (1:3; 4 L), heptane (4 L), and dried to provide the title product as a solid.

Step 5: 3-chloro-5-{[5-chloro-1-(1-t-butyloxycarbonyl-1H-pyrazolo[3,4-b]pyridin-3-ylmethyl)-1H-indazol-4-yl]oxy}benzonitrile A 4-necked round bottom flask (75 L) under nitrogen and equipped with a mechanical stirrer, a thermocouple and an addition funnel was placed on a steam bath. 3-Chloro-5-[(5-chloro-1H-indazol-4-yl)oxy]benzonitrile (2.07 kg; 6.12 moles; 1.0 eq.), 1-(tert-butyl)-3-(bromomethyl)-1H-pyrazolo[3,4-b]pyridine-1-carboxylate (2.48 kg; 7.95 moles; 1.30 eqs.) were charged to the flask, followed by the addition of DMF (11.2 L). The mixture was cooled to 3.1° C. with ice-water, after which DBU (1.46 L; 9.79 moles; 1.60 eqs.) was added over 30 minutes while keeping the internal temperature below about 21° C. The reaction mixture was then cooled to 6° C. and aged at that temperature until complete conversion of the indazole as determined by HPLC. MTBE (10 L), AcOEt (5 L), H$_2$O (10 L) were then added and the mixture transferred to an extractor (100 L). The flask was rinsed with MTBE (1.2 L), EtOAc (1.2 L) and H$_2$O (1.2 L), the rinse was stirred for 10 minutes, and then allowed to settle. The aqueous layer was cut away, and the organic layer was drummed off. The aqueous layer was transferred to the extractor, after which MTBE (7.4 L) and EtOAc (3.7 L) were added, and the mixture stirred for 10 minutes, and then allowed to settle. The aqueous layer was cut away. The first organic layer was transferred to the extractor, and the drum was rinsed with MTBE:EtOAc (2:1; 1.5 L). Water (11.2 L) was added to the extractor, and the mixture was stirred for 10 minutes, then allowed to settle. The aqueous layer was cut away, the organic layer was drummed off, and the extractor was rinsed with AcOEt (1 L×2). The combined organic layers were concentrated in vacuo with rotavap at a bath temperature of 30° C.-35° C. to 4.775 kg (with solvent). The concentrate was then separated via a silica gel column (40 kg) using heptane-EtOH. The desired fractions were concentrated in a round bottom flask (75 L) using a batch concentrator to about 15 L. EtOAc (4 L) was added to the concentrate and the mixture stirred at room temperature overnight. The resulting crystalline slurry was then heated to 45° C., stirred for 40 minutes at 45° C. and then allowed to cool to room temperature. The crystals were then separated by filtration using a filter pot, and the resulting wet cake was rinsed with EtOAc-heptane (1:2; 6 L) and then dried with a nitrogen stream to afford the desired title product as crystals.

Step 6: 3-Chloro-5-{[5-chloro-1-(1H-pyrazolo[3,4-b]pyridin-3-ylmethyl)-1H-indazol-4-yl]oxy}benzonitrile A jacketed reaction vessel (30 L) equipped with a thermocouple was charged with 3-chloro-5-{[5-chloro-1-(1-t-butyloxycarbonyl-1H-pyrazolo[3,4-b]pyridin-3-ylmethyl)-1H-indazol-4-yl]oxy}benzonitrile (1.338 kg; 2.499 moles; 1.0 eq.) and then with DMF (10.7 L) and IPA (2.68 L). Concentrated HCl (2.68 L) was then charged to the vessel during which time the internal temperature rose from 16° C. to 44° C. The mixture was then heated to 60° C. After 1 hour at 60° C., the suspension became a clear solution. Conversion was complete after 1.75 hours as determined by HPLC, at which point the reaction mixture was transferred into a 4-necked round bottom flask (75 L) at 55° C.-60° C. via an in-line filter. The reaction vessel was rinsed with IPA (2 L×2), and the rinse transferred to the flask via the in-line filter. Filtered water (16 L) was then added to the mixture via an additional funnel while maintaining the temperature at 55° C.-60° C., during which crystallization of the title product began. Upon completion of the water addition, the mixture was stirred at 55° C. for 40 minutes, then cooled to room temperature and filtered with a filter pot. The wet cake was rinsed with filtered IPA:water (3:7, 10 L), and then with filtered water (7 L×6), and then dried in a vacuum oven at 40° C. for two days to afford the title product.

Example 2

3-Chloro-5-{[3,5-dichloro-1-(1H-pyrazolo[3,4-b]pyridin-3-ylmethyl)-1H-indazol-4-yl]oxy}benzonitrile

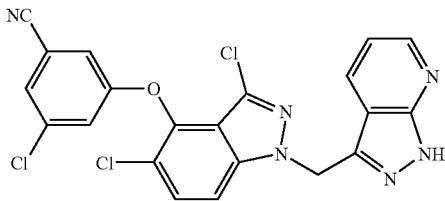

Step 1: 3-Chloro-5-[(3,5-dichloro-1H-indazol-4-yl)oxy]benzonitrile

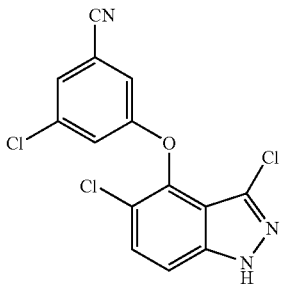

To a solution of 3-chloro-5-[(5-chloro-1H-indazol-4-yl)oxy]benzonitrile (100 mg, 0.329 mmol) in DMF (1 mL) was added 1.0M KOtBu in THF (329 µL, 0.329 mmol) and then N-chlorosuccinimide (44 mg, 0.329 mmol). The resulting reaction mixture was then stirred for 10 minutes, after which the mixture was purified on a LUNA column (10µ, C18, 250×21.2 cm) eluting with 5-95% ACN/water with 0.1% TFA) to give the title compound.
LRMS (M+1)=337.9

Step 2: 3-Chloro-5-{[3,5-dichloro-1-(1H-pyrazolo[3,4-b]pyridin-3-ylmethyl)-1H-indazol-4-yl]oxy}benzonitrile To a solution of 3-chloro-5-[(3,5-dichloro-1H-indazol-4-yl)oxy]benzonitrile (42 mg, 0.124 mmol) in DMF (1 mL) was added tert-butyl 3-(bromomethyl)-1H-pyrazolo[3,4-b]pyridine-1-carboxylate (38.7 mg, 0.124 mmol) and cesium carbonate (81 mg, 0.248 mmol). The resulting mixture was stirred at room temperature for 2 hours, after which the reaction mixture was partitioned between water (2×5 mL) and EtOAc (10 mL). The organic extract was dried over MgSO$_4$, and the solvent removed in vacuo. This residue was purified on a silica gel (12 g) column (0-20% EtOAc/CH$_2$Cl2) to give the Boc protected compound. This material was dissolved in TFA (2 mL) and allowed to stand for 10 minutes, after which the reaction mixture was concentrated in vacuo and the resulting residue was azeotroped from acetonitrile (2×3 mL) to give the title compound.

$^1$H NMR (CDCl$_3$): δ 8.71 (dd, J=1.71 and 4.64 Hz, 1H), 8.01 (dd, J=1.7 and 7.9 Hz, 1H), 7.53 (d, J=9.0 Hz, 1H), 7.48 (d, J=9.0 Hz, 1H), 7.33 (m, 1H), 7.25 (m, 1H), 7.10 (m, 1H), 6.91 (m, 1H) and 5.89 (s, 2H) ppm.

Example 3

3-{[5-Chloro-4-(3-chloro-5-cyanophenoxy)-1H-indazol-1-yl]methyl}-1H-pyrazolo[3,4-b]pyridin-6-aminium chloride. (Alternative name: 3-({1-[(6-Amino-1H-pyrazolo[3,4-b]pyridin-3-yl)methyl]-5-chloro-1H-indazol-4-yl}oxy)-5-chlorobenzonitrile, HCl salt)

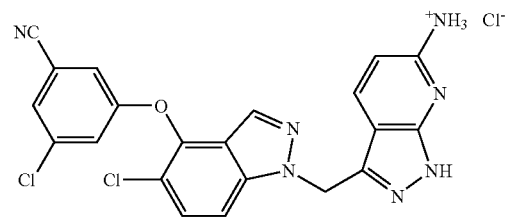

Step 1: 3-Chloro-5-{[5-chloro-1-({1-(4-methoxybenzyl)-6-[(4-methoxybenzyl)amino]-1H-pyrazolo[3,4-b]pyridin-3-yl}methyl)-1H-indazol-4-yl]oxy}benzonitrile

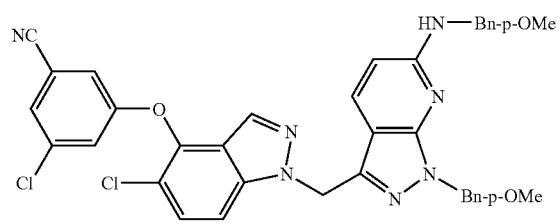

3-chloro-5-[(5-chloro-1H-indazol-4-yl)oxy]benzonitrile (0.677 g, 2.225 mmol) and lithium tert-butoxide (0.178 g, 2.225 mmol) were dissolved in DMF (5 µL) and allowed to stir for 5 minutes. To this mixture at 0° C. was added 3-(chloromethyl)-N,1-bis(4-methoxybenzyl)-1H-pyrazolo[3,4-b]pyridin-6-amine (Intermediate 2; 0.896 g, 2.119 mmol) as a solution in DMF (5 mL). The mixture was then allowed to warm to room temperature overnight, after which aqueous ammonium chloride (20 mL) was added and the mixture was extracted with ethyl acetate (2×50 mL). The combined organic fractions were washed with water (5×50 mL), dried over MgSO$_4$, filtered and concentrated under reduced pressure. The resulting residue was subjected to automated silica gel chromatography eluting with a gradient of 0-10% ethyl acetate in dichloromethane to yield the title product. LRMS (M+1)=691.8

Step 2: 3-({1-[(6-Amino-1H-pyrazolo[3,4-b]pyridin-3-yl)methyl]-5-chloro-1H-indazol-4-yl}oxy)-5-chlorobenzonitrile

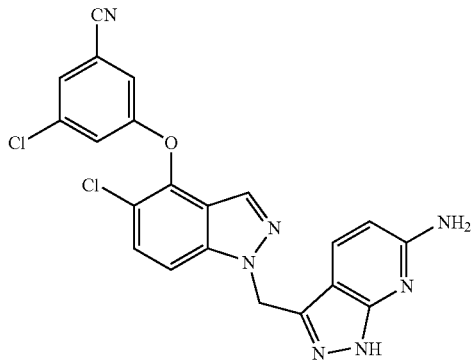

3-chloro-5-{[5-chloro-1-({1-(4-methoxybenzyl)-6-[(4-methoxybenzyl)amino]-1H-pyrazolo[3,4-b]pyridin-3-yl}methyl)-1H-indazol-4-yl]oxy}benzonitrile (0.848 g, 1.228 mmol) was dissolved in TFA (10 mL) and placed in an oil bath at 75° C. After 2.5 hours, the reaction mixture was allowed to cool to room temperature and was concentrated under reduced pressure. The resulting residue was suspended in a chloroform and ethyl acetate mixture (4:1, 200 mL) and aqueous sodium bicarbonate (50 mL) was added. Ethyl acetate was then added until both phases had become solutions. The organic phase was separated and the aqueous phase was washed with chloroform (2×100 mL). The combined organic fractions were dried over MgSO$_4$, filtered and concentrated under reduced pressure. The resulting residue was subjected to automated silica gel chromatography eluting with a gradient of 0-10% methanol in chloroform to yield the title product. $^1$H NMR (DMSO-d$_6$): δ 12.60 (s, 1H), 7.86 (s, 1H), 7.81-7.78 (m, 1H), 7.73 (d, J=9.0 Hz, 1H), 7.58 (d, J=9.0 Hz, 1H), 7.49-7.47 (m, 1H), 7.38-7.34 (m, 2H), 6.30 (s, 2H), 6.21 (d, J=8.8 Hz, 1H), 5.82 (s, 2H). LRMS (M+1)=449.7

Step 3: 3-{[5-Chloro-4-(3-chloro-5-cyanophenoxy)-1H-indazol-1-yl]methyl}-1H-pyrazolo[3,4-b]pyridin-6-aminium chloride To 3-({1-[(6-amino-1H-pyrazolo[3,4-b]pyridin-3-yl)methyl]-5-chloro-1H-indazol-4-yl}oxy)-5-chlorobenzonitrile (0.936 g, 2.079 mmol) as a solution in 20% methanol in chloroform (300 mL) was added 1N HCl (2.079 mL, 2.079 mmol), and the resulting mixture was then concentrated under reduced pressure. The resulting white paste was diluted with acetonitrile (100 mL) and the solvent evaporated in vacuo. The dilution-evaporation was repeated twice more for a total of three times. The resulting residue was placed under vacuum overnight to give product. $^1$H NMR (DMSO-d$_6$):

6.7.91 (s, 1H), 7.81 (s, 3H), 7.68-7.60 (m, 2H), 7.48 (s, 1H), 7.37 (s, 1H), 6.50-6.30 (m, 2H), 6.00-5.86 (m, 2H). HRMS (M+1)=450.06

Example 4

3-chloro-5-{[5-chloro-1-(1H-pyrazolo[3,4-b]pyridin-3-ylmethyl)-1H-1,2,3-benzotriazol-4-yl]oxy}benzonitrile

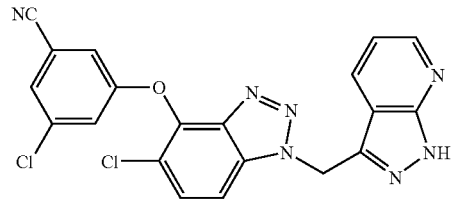

Step 1:
1-(4-methoxybenzyl)-1H-1,2,3-benzotriazol-4-ol

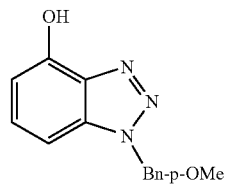

4-Methoxy-benzylbromide (2.976 g, 14.80 mmol) was added to a stirred suspension of 4-hydroxy-benztriazole (2.0 g, 14.80 mmol) and cesium carbonate (9.645 g, 29.6 mmol) in DMF (30 mL) at room temperature and the reaction mixture was stirred for 1 hour. Aqueous ammonium chloride (30 mL) was then added to quench the reaction and the mixture was then extracted with ethyl acetate (2×100 mL). The organic fractions were combined and concentrated under reduced pressure. The resulting residue was subjected to reverse phase chromatography (5-95% MeCN/H$_2$O, 0.1% TFA). The product fractions were combined and extracted with dichloromethane (2×100 mL). The combined extracts were dried over MgSO$_4$, filtered and concentrated under reduced pressure to yield the title product. $^1$H NMR (DMSO d6) δ 10.67 (s, 1, H), 7.29-7.27 (m, 3H), 7.15 (d, J=8.3 Hz, 1H), 6.88-6.84 (m, 2H), 6.63 (d, J=7.6 Hz, 1H), 5.80 (s, 2H), 3.71 (s, 3H).

Step 2: 5-Chloro-1-(4-methoxybenzyl)-1H-1,2,3-benzotriazol-4-ol

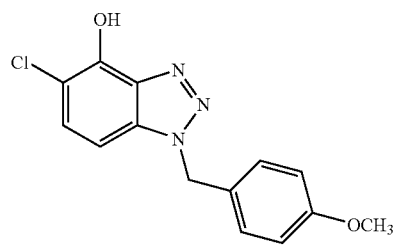

To a stirred solution of 1-(4-methoxybenzyl)-1H-1,2,3-benzotriazol-4-ol (0.984 g, 3.85 mmol) at 0° C. in THF (15 mL) was added 1N NaOH (3.85 mL, 3.85 mmol). The resulting mixture was then stirred for several minutes, after which N-chloro-succinimide (0.515 g, 3.85 mmol) was added in one portion. The stirred reaction mixture was quenched after 5 minutes at 0° C. with aqueous ammonium chloride (25 mL) and extracted with dichloromethane (2×100 mL). The combined extracts were concentrated under reduced pressure. The resulting residue was subjected to reverse phase chromatography (5-95% MeCN/H$_2$O, 0.1% TFA). The product fractions were combined and extracted with dichloromethane (2×100 mL). The combined extracts were dried over MgSO$_4$, filtered and concentrated under reduced pressure to afford the title product. $^1$H NMR (DMSO d6) δ 11.61 (s, 1H), 7.44 (d, J=8.5 Hz, 1H), 7.30 (d, J=8.5 Hz, 2H), 7.23 (d, J=8.6 Hz, 1H), 6.90 (d, J=8.8 Hz, 2H), 5.84 (s, 2H), 3.71 (s, 3H).

Step 3: 3-Chloro-5-{[5-chloro-1-(4-methoxybenzyl)-1H-1,2,3-benzotriazol-4-yl]oxy}benzonitrile

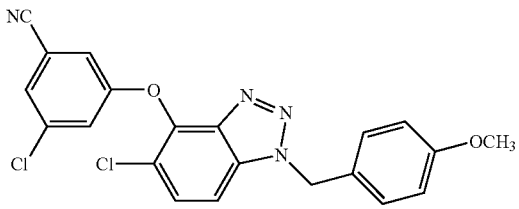

A stirred suspension of 5-chloro-1-(4-methoxybenzyl)-1H-1,2,3-benzotriazol-4-ol (0.050 g, 0.173 mmol), 3-fluoro-5-chloro-benzonitrile (0.081 g, 0.518 mmol) and cesium carbonate (0.068 g, 0.207 mmol) in NMP (1.5 mL) was heated at 140° C. for 72 hours. The reaction mixture was then quenched with aqueous ammonium chloride (25 mL) and extracted with dichloromethane (2×100 mL). The combined extracts were concentrated under reduced pressure. The resulting residue was subjected to reverse phase chromatography (5-95% MeCN/H$_2$O, 0.1% TFA). The product fractions were combined and extracted with dichloromethane (2×100 mL). The combined extracts were dried over MgSO$_4$, filtered and concentrated under reduced pressure to yield the title product. $^1$H NMR (DMSO d6) δ 7.90-7.88 (m, 1H), 7.80 (s, 1H), 7.79-7.75 (m, 1H), 7.60-7.55 (m, 2H), 7.40-7.35 (d, J=6.9 Hz, 2H), 6.95-6.88 (m, 2H), 5.80 (s, 2H), 3.71 (s, 3H).

Step 4: 3-Chloro-5-[(5-chloro-1H-1,2,3-benzotriazol-4-yl)oxy]benzonitrile

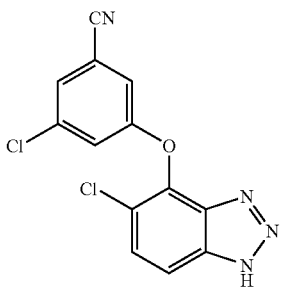

3-chloro-5-{[5-chloro-1-(4-methoxybenzyl)-1H-1,2,3-benzotriazol-4-yl]oxy}benzonitrile (0.0097 g, 0.023 mmol) was dissolved in TFA (2 mL) and heated at 75° C. for 2 hours. The reaction mixture was then allowed to cool to room temperature and then concentrated under reduced pressure. The resulting residue was subjected to automated silica gel chromatography eluting with 0-25% ethyl acetate in hexanes to give the title product. LRMS (M+1)=304.8

Step 5: tert-Butyl 3-{[5-chloro-4-(3-chloro-5-cyanophenoxy)-1H-1,2,3-benzotriazol-1-yl]methyl}-1H-pyrazolo[3,4-b]pyridine-1-carboxylate

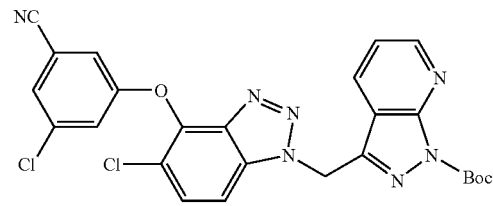

To 3-chloro-5-[(5-chloro-1H-1,2,3-benzotriazol-4-yl)oxy]benzonitrile (0.006 g, 0.020 mmol) and cesium carbonate (0.0077 g, 0.024 mmol) suspended in DMF (1 mL) at room temperature was added tert-butyl 3-(bromomethyl)-1H-pyrazolo[3,4-b]pyridine-1-carboxylate (=Intermediate 1; 0.0068 g, 0.022 mmol) as a solution in DMF (0.5 mL). After stirring for 1 hour at room temperature, the reaction mixture was quenched with aqueous ammonium chloride (2 mL), and the quenched mixture was extracted with ethyl acetate (2×10 mL). The combined organic fractions were washed with water (3×10 mL), dried over MgSO$_4$, filtered and concentrated under reduced pressure. The resulting residue was subjected to automated silica gel chromatography eluting with a gradient of 25-50% ethyl acetate in hexanes to afford the title product. LRMS (M+1)=435.7

Step 6: 3-Chloro-5-{[5-chloro-1-(1H-pyrazolo[3,4-b]pyridin-3-ylmethyl)-1H-1,2,3-benzotriazol-4-yl]oxy}benzonitrile tert-Butyl 3-{[5-chloro-4-(3-chloro-5-cyanophenoxy)-1H-1,2,3-benzotriazol-1-yl]methyl}-1H-pyrazolo[3,4-b]pyridine-1-carboxylate (0.001 g, 1.86 μmol) was dissolved in TFA (2 mL) at room temperature. After 5 minutes, the solvent was evaporated in vacuo to afford the title product.

$^1$H NMR (CDCl$_3$): δ 8.52-8.46 (m, 1H), 8.35 (d, J=4.15 Hz, 1H), 7.59 (d, J=8.79 Hz, 1H), 7.57 (d, J=8.78 Hz, 1H), 7.36 (s, 1H), 7.33-7.27 (m, 1H), 6.98 (s, 1H), 6.25 (s, 2H). HRMS (M+1)=436.05.

Example 4A

Alternative preparation of 3-chloro-5-{[5-chloro-1-(1H-pyrazolo[3,4-b]pyridin-3-ylmethyl)-1H-1,2,3-benzotriazol-4-yl]oxy}benzonitrile Step 1: 2-(3-bromo-5-chlorophenoxy)-1-chloro-3-nitrobenzene 2,3-dichloronitrobenzene (764 mg, 3.99 mmol), 3-bromo-5-chlorophenol (1.65 g, 7.98 mmol) and potassium carbonate (661 mg, 4.79 mmol) were suspended in NMP (5 mL) and placed in an oil bath at 120° C. After 2 hours, the reaction was allowed to cool to room temperature, saturated aqueous ammonium chloride (10 mL) was added and the mixture was extracted with ethyl acetate (2×50 mL). The combined organic fractions were washed with dilute brine (4×50 mL), dried (MgSO$_4$), filtered and the solvent was evaporated under reduced pressure. The residue was purified by automated column chromatography on silica gel (80 g), eluting with 0-100% CH$_2$Cl$_2$/hexanes to yield the title compound. $^1$H NMR (CD$_3$CN) δ 8.02 (dd, J=8.3 Hz, J=1.5 Hz, 1H), 7.88 (dd, J=8.2 Hz, J=1.6 Hz, 1H), 7.52 (dd, J=8.2 Hz, J=8.3 Hz, 1H), 7.38 (m, 1H), 7.07 (m, 1H), 6.97 (m, 1H).

Step 2: 3-(3-bromo-5-chlorophenoxy)-4-chloro-2-nitroaniline

To copper (I) chloride (5.45 mg, 0.055 mmol) and potassium tert-butoxide (247 mg, 2.204 mmol) suspended in DMF (3 mL) at 0° C. was added 1,1,1-trimethylhydrazinium iodide (139 mg, 0.689 mmol). This mixture was allowed to stir for several minutes at which point the mixture was cooled to −40° C. and 2-(3-bromo-5-chlorophenoxy)-1-chloro-3-nitrobenzene (200 mg, 0.551 mmol) as a solution in DMF (1 mL) was added dropwise. The reaction was maintained at −40° C. for 15 minutes and was then quenched at −40° C. with saturated aqueous ammonium chloride (10 mL). Water (10 mL) was added and the mixture was allowed to warm to room temperature. The mixture was extracted with ethyl acetate (2×50 mL). The combined organic fractions were washed with water (3×50 mL), dried (MgSO$_4$), filtered and the solvent was evaporated under reduced pressure. The resulting residue was purified by automated column chromatography on silica gel (40 g) eluting with 0-25% EtOAc/hexanes to give the title product. LRMS (M+1)=378.7.

Step 3: 3-(3-bromo-5-chlorophenoxy)-4-chlorobenzene-1,2-diamine 3-(3-bromo-5-chlorophenoxy)-4-chloro-2-nitroaniline (5.7 g, 15 mmol) and tin(II) chloride dihydrate (17 g, 75 mmol) were suspended in MeOH (100 mL) and heated to 75° C. under a reflux condenser and N$_2$. After 10 hours, the reaction was allowed to cool to room temperature. The reaction was concentrated under reduced pressure, diluted with ethyl acetate (150 mL) and 10% aqueous sodium carbonate (250 mL) was added with vigorous stirring until the pH was 10. The mixture was filtered through celite. The resulting biphasic filtrate was separated and the aqueous extracted again with ethyl acetate (150 mL). The combined organic fractions were dried (MgSO$_4$), filtered and the solvent was evaporated under reduced pressure to yield the title product. LRMS (M+1)=348.7.

Step 4: 4-(3-bromo-5-chlorophenoxy)-5-chloro-1H-1,2,3-benzotriazole 3-(3-bromo-5-chlorophenoxy)-4-chlorobenzene-1,2-diamine (4.97 g, 14.3 mmol) in acetic acid (25 mL) was cooled to 15° C. under N$_2$ and sodium nitrite (1.08 g, 15.7 mmol) in water (39.3 mL) was added dropwise. After 1.5 hours, the reaction was diluted with EtOAc (300 mL), and the organic phase was separated and washed with water (3×100 mL). The organic phase was then dried (MgSO$_4$), filtered, concentrated to afford the title product. LRMS (M+1) 359.7.

Step 5: 3-chloro-5-[(5-chloro-1H-1,2,3-benzotriazol-4-yl)oxy]benzonitrile 4-(3-bromo-5-chlorophenoxy)-5-chloro-1H-1,2,3-benzotriazole (5.0 g, 14 mmol), tetrakis triphenylphosphine palladium (0) (4.83 g, 4.83 mmol) and zinc cyanide (1.96 g, 16.7 mmol) were suspended in dry DMF (50 mL) under N$_2$ and placed in an oil bath at 90° C. After 2.5 hours, the reaction was allowed to cool to room temperature. The mixture was diluted with EtOAc (300 mL) and washed with water (4×100 mL), dried (MgSO$_4$), filtered and concentrated with silica gel (20 g). This was purified by automated column chromatography on silica gel (120 g), eluting with 0-30% EtOAc/hexanes to deliver the title compound. LRMS (M+1)=304.8.

Step 6: tert-Butyl 3-{[5-chloro-4-(3-chloro-5-cyanophenoxy)-1H-1,2,3-benzotriazol-1-yl]methyl}-1H-pyrazolo[3,4-b]pyridine-1-carboxylate

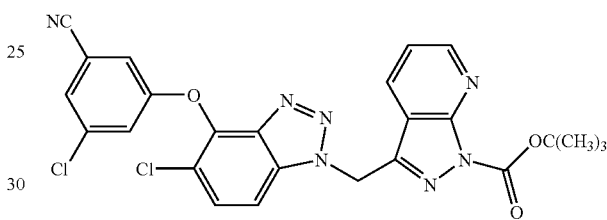

To 3-chloro-5-[(5-chloro-1H-1,2,3-benzotriazol-4-yl)oxy]benzonitrile (0.006 g, 0.020 mmol) and cesium carbonate (0.0077 g, 0.024 mmol) suspended in DMF (1 mL) at room temperature was added tert-butyl 3-(bromomethyl)-1H-pyrazolo[3,4-b]pyridine-1-carboxylate (=Intermediate 1; 0.0068 g, 0.022 mmol) as a solution in DMF (0.5 mL). After stirring for 1 hour at room temperature, the reaction mixture was quenched with aqueous ammonium chloride (2 mL), and the quenched mixture was extracted with ethyl acetate (2×10 mL). The combined organic fractions were washed with water (3×10 mL), dried over MgSO$_4$, filtered and concentrated under reduced pressure. The resulting residue was subjected to automated silica gel chromatography eluting with a gradient of 25-50% ethyl acetate in hexanes to afford the title product. LRMS (M+1)=435.7

Step 7: 3-Chloro-5-{[5-chloro-1-(1H-pyrazolo[3,4-b]pyridin-3-ylmethyl)-1H-1,2,3-benzotriazol-4-yl]oxy}benzonitrile tert-Butyl 3-{[5-chloro-4-(3-chloro-5-cyanophenoxy)-1H-1,2,3-benzotriazol-1-yl]methyl}-1H-pyrazolo[3,4-b]pyridine-1-carboxylate (0.001 g, 1.86 μmol) was dissolved in TFA (2 mL) at room temperature. After 5 minutes, the solvent was evaporated in vacuo to afford the title product.

$^1$H NMR (CDCl$_3$): δ 8.52-8.46 (m, 1H), 8.35 (d, J=4.15 Hz, 1H), 7.59 (d, J=8.79 Hz, 1H), 7.57 (d, J=8.78 Hz, 1H), 7.36 (s, 1H), 7.33-7.27 (m, 1H), 6.98 (s, 1H), 6.25 (s, 2H). HRMS (M+1)=436.05.

Example 5

3-chloro-5-({5-chloro-1-[(7-oxido-1H-pyrazolo[3,4-b]pyridin-3-yl)methyl]-1H-indazol-4-yl}oxy)benzonitrile

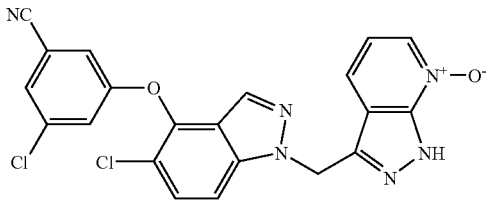

To a suspension of 3-chloro-5-{[5-chloro-1-(1H-pyrazolo[3,4-b]pyridin-3-ylmethyl)-1H-indazol-4-yl]oxy}benzonitrile (96 mg, 0.221 mmol) was added mCPBA (59.8 mg, 0.243 mmol) and stirred at room temperature for 18 hours. The suspension was concentrated in vacuo and then resuspended in DMF (5 mL). This suspension was filtered and then purified by reverse phase HPLC (Luna column, 10μ, C18, 250×21.2 cm) eluting with 5-95% ACN/water with 0.1% TFA). The desired fractions were concentrated to dryness and the resulting solid was suspended in MeOH (1 mL) and filtered to give the title compound.

$^1$H NMR (DMSO-d$_6$): δ 8.35 (d, 1H, J=6.1 Hz), 7.90 (s, 1H), 7.82 (d, 1H, J=9 Hz), 7.80 (dd, 1H, J=1.5 Hz), 7.63 (d, 1H, J=9 Hz), 7.51 (d, 1H, J=8.3 Hz), 7.47 (m, 1H), 7.40 (dd, 1H, J=2 Hz), 7.12 (dd, 1H, J=6 and 8 Hz) and 6.06 (s, 1H) ppm. LRMS (M+1)=450.8.

Example 6

3-({1-[(6-amino-1H-pyrazolo[3,4-b]pyridin-3-yl)methyl]-5-chloro-1H-1,2,3-benzotriazol-4-yl}oxy)-5-chlorobenzonitrile

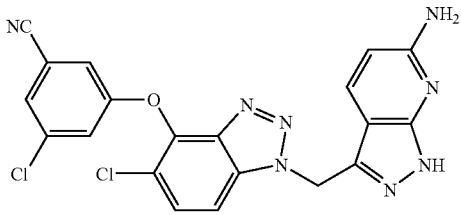

Step 1: 3-chloro-5-{[5-chloro-1-({1-(4-methoxybenzyl)-6-[(4-methoxybenzyl)amino]-1H-pyrazolo[3,4-b]pyridin-3-yl}methyl)-1H-1,2,3-benzotriazol-4-yl]oxy}benzonitrile

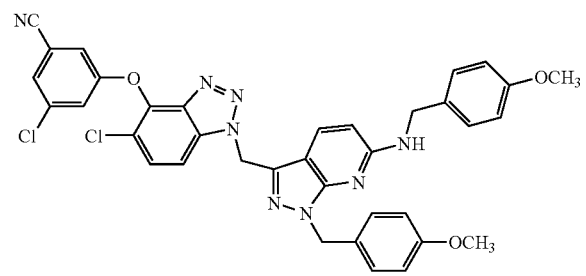

3-chloro-5-[(5-chloro-1H-1,2,3-benzotriazol-4-yl)oxy]benzonitrile (140 mg, 0.459 mmol) and lithium tert-butoxide (37 mg, 0.459 mmol) were dissolved in DMF (1 mL) under N$_2$ and allowed to stir for 20 minutes. After this time, the reaction was cooled to 0° C. and 3-(chloromethyl)-N,1-bis(4-methoxybenzyl)-1H-pyrazolo[3,4-b]pyridin-6-amine as a solution in DMF (1 mL) was added dropwise. After 1 hour, the reaction was quenched with saturated aqueous ammonium chloride (3 mL), diluted with water (3 mL) and the mixture was extracted with ethyl acetate (2×25 mL). The combined organic fractions were washed with dilute brine (4×10 mL), dried (MgSO$_4$), filtered and the solvent was evaporated under reduced pressure. The resulting residue was purified by automated column chromatography on silica gel (12 g), eluting with 0-100% EtOAc/hexanes to give the title compound. LRMS (M+1)=690.5.

Step 2: 3-({1-[(6-amino-1H-pyrazolo[3,4-b]pyridin-3-yl)methyl]-5-chloro-1H-1,2,3-benzotriazol-4-yl}oxy)-5-chlorobenzonitrile 3-chloro-5-{[5-chloro-1-({1-(4-methoxybenzyl)-6-[(4-methoxybenzyl)amino]-1H-pyrazolo[3,4-b]pyridin-3-yl}methyl)-1H-1,2,3-benzotriazol-4-yl]oxy}benzonitrile (135 mg, 0.195 mmol) was dissolved in TFA (10 mL) and placed in an oil bath at 75° C. After 2 hours, the reaction was allowed to cool to room temperature and was concentrated under reduced pressure. The resulting residue was diluted with CHCl$_3$/EtOAc (4:1, 50 mL) and methanol was added until a solution was achieved. 50% Aqueous sodium bicarbonate (10 mL) was then added. The organic phase was removed and the aqueous was extracted with CHCl$_3$ (25 mL). The combined organic fractions were, dried (MgSO$_4$), filtered and concentrated. The resulting residue was adsorbed onto silica gel with CHCl$_3$/MeOH and purified by automated column chromatography on silica gel (12 g), eluting with 0-5% MeOH/CH$_2$Cl$_2$ to afford the title compound. $^1$H NMR (DMSO d-6) δ 7.82 (d, J=9.0 Hz, 1H), 7.81 (m, 1H), 7.75 (d, J=9.0 Hz, 1H), 7.58 (m, 1H), 7.55 (d, J=8.8 Hz, 1H), 7.52 (m, 1H), 6.36 (m, 1H), 6.30 (d, J=8.8 Hz, 1H), 6.16 (s, 1H).

Example 7

3-chloro-5-{[5-chloro-1-(1H-pyrazolo[3,4-b]pyridin-3-ylmethyl)-1H-benzimidazol-4-yl]oxy}benzonitrile dihydrochloride Dihydrocloride salt of:

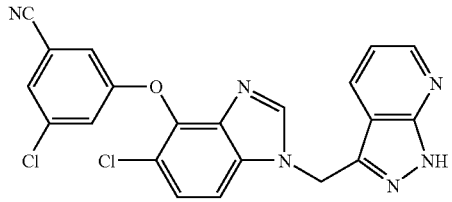

Step 1: 4-(3-bromo-5-chlorophenoxy)-5-chloro-1H-benzimidazole

A solution of 3-(3-bromo-5-chlorophenoxy)-4-chlorobenzene-1,2-diamine (400 mg, 1.149 mmol) in 90% formic acid (5 mL) was heated to 100° C. for 1 hour. This mixture was concentrated in vacuo and then partitioned between ethyl acetate (40 mL) and sat. aq. NaHCO$_3$ (40 mL). The organic extract was dried over MgSO$_4$, filtered and concentrated in vacuo to give the desired compound. LRMS (M+1)=358.7.

Step 2: 3-chloro-5-[(5-chloro-1H-benzimidazol-4-yl)oxy]benzonitrile

To a solution of 4-(3-bromo-5-chlorophenoxy)-5-chloro-1H-benzimidazole 430 mg, 1.201 mmol) in DMF (5 mL) was added palladium tetrakistriphenylphosphine (416 mg, 0.360 mmol) and zinc cyanide (141 mg, 1.201 mmol) and the mixture heated to 90° C. for 1 hour. This mixture was partitioned between ethyl acetate (50 mL) and water (20 mL). The organic extract was washed with water (10 mL), dried over MgSO$_4$, filtered and the solvent removed in vacuo. This residue was purified on silica gel eluting with 0-20% ethyl acetate/methylene chloride to give the title compound. LRMS (M+1)=303.8.

Step 3: 3-chloro-5-{[5-chloro-1-(1H-pyrazolo[3,4-b]pyridin-3-ylmethyl)-1H-benzimidazol-4-yl]oxy}benzonitrile dihydrochloride To a suspension of 3-chloro-5-[(5-chloro-1H-benzimidazol-4-yl)oxy]benzonitrile (101 mg, 0.332 mmol) and tert-butyl 3-(bromomethyl)-1H-pyrazolo[3,4-b]pyridine-1-carboxylate (104 mg, 0.332 mmol) in DMF (1 mL) was added cesium carbonate (216 mg, 0.664 mmol) and the suspension was stirred at room temperature for 2.25 hours. This mixture was diluted with water (10 mL) and extracted with ethyl acetate (2×12 mL). The combined extracts were washed with water, dried over MgSO$_4$, filtered and evaporated in vacuo. This residue was purified on silica gel (40 g) column eluting with 0-100% ethyl acetate/methylene chloride. The fractions corresponding to the desired Boc protected product were combined and the solvent removed in vacuo. This residue was redissolved in TFA (3 mL) and allowed to stand at room temperature for 10 minutes. The solvent was removed in vacuo and the residue was purified on silica gel (4 g) column eluting with 0-10% methanol/methylene chloride gradient. The pure fractions were combined, treated with 1N hydrochloric acid and the solvent removed in vacuo to provide title compound. $^1$H NMR (DMSO-d$_6$): δ 13.7 (s, 1H), 8.58 (s, 1H), 8.52 (d, 1H, J=4.4 Hz), 8.16 (d, 1H, 8.0 Hz), 7.74 (dd, 1H, J=1.5 Hz), 7.63 (d, 1H, J=8.8 Hz), 7.47 (d, 1H, J=8.5 Hz), 7.39 (dd, 1H, J=1.5 Hz), 7.29 (dd, 1H, J=2 Hz), 7.19 (dd, 1H, J=4.5 and 8.1 Hz) and 5.92 (s, 2H) ppm. LRMS (M+1)=434.7

Example 8

2-[[(3-{[5-chloro-4-(3-chloro-5-cyanophenoxy)-1H-1,2,3-benzotriazol-1-yl]methyl}-1H-pyrazolo[3,4-b]pyridin-1-yl)carbonyl](methyl)amino]-N-methyl-ethanaminium chloride

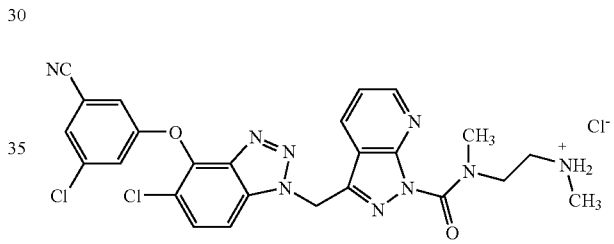

Step 1: tert-butyl {2-[[(3-{[5-chloro-4-(3-chloro-5-cyanophenoxy)-1H-1,2,3-benzotriazol-1-yl]methyl}-1H-pyrazolo[3,4-b]pyridin-1-yl)carbonyl](methyl)amino]ethyl}methyl carbamate

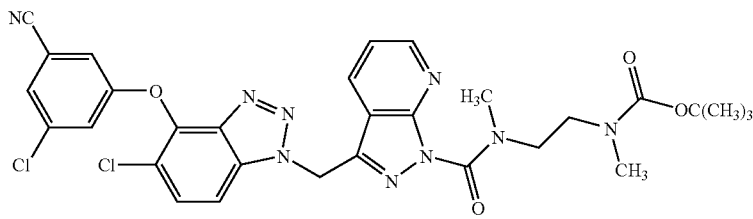

To a suspension of 3-chloro-5-{[5-chloro-1-(1H-pyrazolo[3,4-b]pyridin-3-ylmethyl)-1H-1,2,3-benzotriazol-4-yl]oxy}benzonitrile (117 mg, 0.268 mmol) in dichloromethane (5 mL) at 0° C. was added pyridine (0.043 mL, 0.536 mmol). To this suspension was then added triphosgene (32 mg, 0.107 mmol) as a solid, in one addition, followed by addition of diisopropyl ethylamine (0.198 mL, 1.135 mmol). This suspension was allowed to stir at 0° C. until a solution was achieved. At this point, 2-[(tert-butoxycarbonyl)amino]-N-methylethanaminium chloride (120 mg, 0.567 mmol) was added as a solid followed by diisopropyl ethylamine (0.047 mL, 0.268 mmol). The reaction was allowed to warm to room temperature and after 10 minutes, the reaction was diluted with dichloromethane (25 mL), washed with water (15 mL) and the aqueous layer was re-extracted with dichloromethane (25 mL). The combined organic fractions were dried (MgSO$_4$), filtered and concentrated. The resulting residue was purified by reverse phase chromatography eluting with 30-95% MeCN/H$_2$O+0.1% TFA. LRMS (M+1)=549.6.

Step 2: 2-[[(3-{[5-chloro-4-(3-chloro-5-cyanophenoxy)-1H-1,2,3-benzotriazol-1-yl]methyl}-1H-pyrazolo[3,4-b]pyridin-1-yl)carbonyl](methyl)amino]-N-methylethanaminium chloride tert-butyl {2-[[(3-{[5-chloro-4-(3-chloro-5-cyanophenoxy)-1H-1,2,3-benzotriazol-1-yl]methyl}-1H-pyrazolo[3,4-b]pyridin-1-yl)carbonyl](methyl)amino]ethyl}methylcarbamate (125 mg, 0.192 mmol) was dissolved in TFA (5 mL). After 20 minutes, the reaction was concentrated and the resulting residue was purified by reverse phase chromatography eluting with 30-95% MeCN/H$_2$O+0.1% TFA. Product fractions were concentrated under reduced pressure and the resulting solid was dissolved in MeCN (3 mL), cooled to −78° C. and 1N HCl (5 mL) added. This froze and was lyophilized to yield the title compound. $^1$H NMR (DMSO-d$_6$) δ 8.68 (dd, J=4.5 Hz, J=1.5 Hz, 1H), 8.57 (s, 1H), 8.26 (d, J=8.0 Hz, 1H), 8.11 (s, 1H), 7.96 (m, 1H), 7.83 (d, J=9.0 Hz, 1H), 7.72 (m, 1H), 7.58 (m, 1H), 7.44 (dd, J=4.6 Hz, J=8.0 Hz, 1H), 7.35 (m, 1H), 7.28 (m, 1H), 6.50 (s, 2H), 3.70 (s, 3H), 3.20 (s, 2H), 3.00 (s, 2H), 2.20 (m, 3H).

Example 9

N-(2-chlorobenzyl)-2-[5-chloro-4-(3-chloro-5-cyanophenoxy)-1H-1,2,3-benzotriazol-1-yl]-N-methylacetamide

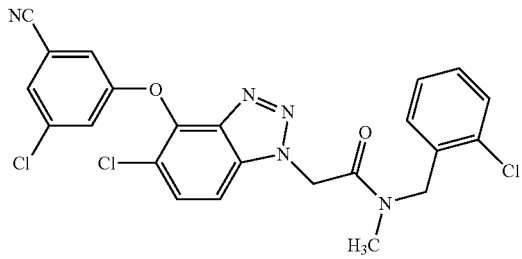

3-chloro-5-[(5-chloro-1H-1,2,3-benzotriazol-4-yl)oxy]benzonitrile (25 mg, 0.082 mmol) and lithium tert-butoxide (6.9 mg, 0.089 mmol) were dissolved in DMF (0.5 mL) and allowed to stir for 5 minutes. After this time, the reaction was cooled to 0° C. and 2-chloro-N-(2-chlorobenzyl)-N-methylacetamide as a solution in DMF (0.5 mL) was added dropwise. This was allowed to warm to room temperature and after 16 hours, the reaction was quenched with TFA, diluted with MeCN and purified by reverse phase chromatography eluting with 30-95% MeCN/H$_2$O+0.1% TFA. Product fractions were lyophilized to yield the title compound. $^1$H NMR (DMSO-d$_6$) δ 7.84 (m, 1H), 7.83 (d, J=9.0 Hz, 1H), 7.79 (d, J=9.0 Hz, 1H), 7.58 (m, 1H), 7.51 (m, 1H), 7.47 (m, 1H), 7.35 (m, 3H), 6.05 (s, 2H), 4.62 (s, 2H), 3.20 (s, 3H).

Example 10

3-({1-[(6-amino-1H-pyrazolo[3,4-b]pyridin-3-yl)methyl]-5-chloro-1H-benzimidazol-4-yl}oxy)-5-chlorobenzonitrile bis(trifluoroacetate)

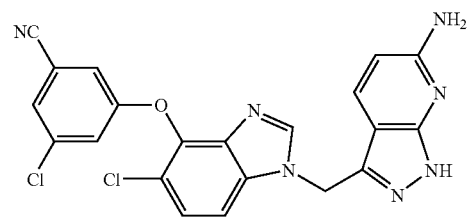

Step 1: 3-chloro-5-{[5-chloro-1-({1-(4-methoxybenzyl)-6-[(4-methoxybenzyl)amino]-1H-pyrazolo[3,4-b]pyridin-3-yl}methyl)-1H-benzimidazol-4-yl]oxy}benzonitrile bis(trifluoroacetate)

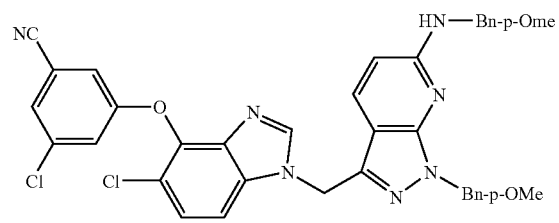

To an ice bath cooled solution of 3-chloro-5-[(5-chloro-1H-benzimidazol-4-yl)oxy]benzonitrile (48 mg, 0.158 mmol) in DMF (1 mL) was added lithium t-butoxide (12 mg, 0.158 mmol) and stirred for 5 minutes. After this time, 3-(chloromethyl)-N,1-bis(4-methoxybenzyl)-1H-pyrazolo[3,4-b]pyridin-6-amine (44 mg, 0.104 mmol) was added and the mixture stirred for 10 minutes over an ice bath. After this time, the reaction mixture was allowed to stir overnight at room temperature. The reaction mixture was then purified by reverse phase HPLC (Luna column, 10μ, C18, 250×21.2 cm) eluting with 5-95% ACN/water with 0.1% TFA) to give the desired compound. LRMS (M+1)=689.5.

Step 2: 3-({1-[(6-amino-1H-pyrazolo[3,4-b]pyridin-3-yl)methyl]-5-chloro-1H-benzimidazol-4-yl}oxy)-5-chlorobenzonitrile bis(trifluoroacetate)

A solution of 3-chloro-5-{[5-chloro-1-({1-(4-methoxybenzyl)-6-[(4-methoxybenzyl)amino]-1H-pyrazolo[3,4-b]pyridin-3-yl}methyl)-1H-benzimidazol-4-yl]oxy}benzonitrile bis(trifluoroacetate) (39 mg, 0.042 mmol) in trifluoroacetic acid (2 mL) was heated to 70° C. for 4 hours. After this time, the solvent was removed in vacuo and the residue was purified on a Luna column (10μ, C18, 250×21.2 cm) eluting with 5-95% ACN/water with 0.1% TFA) to give the desired compound.
$^1$H NMR (DMSO-d$_6$): δ 12.73 (s, 1H), 8.50 (s, 1H), 7.74 (dd, 1H, J=1.5 Hz), 7.62 (br s, 1H), 7.59 (s, 1H, J=8.8 Hz), 7.46 (d, 1H, J=8.5 Hz), 7.41 (dd, 1H, J=1.5 Hz), 7.27 (br m, 1H), 6.40 (br, 3H) and 5.70 (s, 2H) ppm. LRMS (M+1)=448.8.

Example 11

3-chloro-5-{[5-chloro-1-(2-oxo-2-pyridin-3-ylethyl)-1H-1,2,3-benzotriazol-4-yl]oxy}benzonitrile

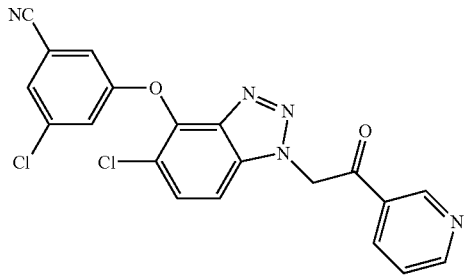

3-chloro-5-[(5-chloro-1H-1,2,3-benzotriazol-4-yl)oxy]benzonitrile (50 mg, 0.164 mmol) and cesium carbonate (160 mg, 0.492 mmol) were suspended in DMF (1 μL) at room temperature under $N_2$. To this was added 2-bromo-1-pyridin-3-ylethanone (48.3 mg, 0.172 mmol) as a solid. The resulting mixture was stirred under $N_2$ for 16 hours. The reaction mixture was then diluted with water (2 mL) and extracted with EtOAc (2×15 mL). The combined organic fractions were washed with water (3×10 mL), dried ($MgSO_4$), filtered and the solvent was evaporated under reduced pressure. The resulting residue was purified by reverse phase chromatography eluting with 30-95% MeCN/$H_2O$+0.1% TFA. The product was lyophilized to afford the title compound. $^1$H NMR (DMSO-$d_6$) δ 9.30 (s, 1H), 8.90 (m, 1H), 8.44 (d, J=7.8 Hz, 1H), 7.88 (d, J=8.8 Hz, 1H), 7.85 (m, 1H), 7.79 (d, J=8.8 Hz, 1H), 7.68 (m, 1H), 7.60 (m, 1H), 7.57 (m, 1H), 6.68 (s, 2H). HRMS (M+1)=424.0395

Example 12

2-[5-chloro-4-(3-chloro-5-cyanophenoxy)-1H-1,2,3-benzotriazol-1-yl]-N-(2-chlorophenyl)acetamide

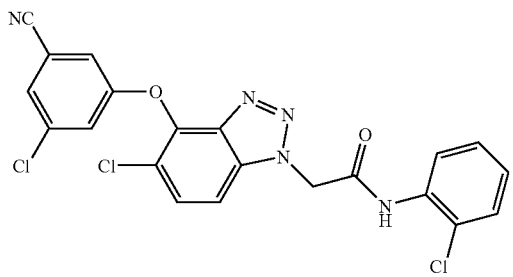

To a suspension of [5-chloro-4-(3-chloro-5-cyanophenoxy)-1H-1,2,3-benzotriazol-1-yl]acetic acid (15 mg, 0.041 mmol) (see step 2 in Example 16) in DCM (0.5 mL) was added oxalyl chloride (58 mg, 0.454 mmol). This was followed by addition of DMF (1 drop) and then, following bubbling cessation, by addition of 2-chloroaniline (158 mg, 1.239 mmol). After 10 minutes, the reaction mixture was concentrated, taken up in DMF/MeOH and purified by reverse phase chromatography, eluting with 30-95% MeCN/ $H_2O$+0.1% TFA. The product fraction was lyophilized to yield the title compound. $^1$H NMR (DMSO-$d_6$) δ 10.2 (s, 1H), 7.90 (d, J=9.0 Hz, 1H), 7.83 (m, 2H), 7.75 (d, J=8.3 Hz, 1H), 7.55 (m, 3H), 7.34 (m, 1H), 7.24 (m, 1H), 5.85 (s, 2H). HRMS (M+1)=472.0152.

Example 13

2-[5-chloro-4-(3-chloro-5-cyanophenoxy)-1H-1,2,3-benzotriazol-1-yl]-N-[3-(trifluoromethyl)pyridin-4-yl]acetamide

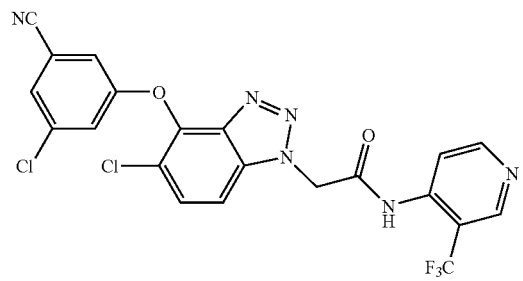

To a suspension of [5-chloro-4-(3-chloro-5-cyanophenoxy)-1H-1,2,3-benzotriazol-1-yl]acetic acid (15 mg, 0.041 mmol) (see step 2 in Example 16) in DCM (0.5 mL) was added oxalyl chloride (58 mg, 0.454 mmol), followed by addition of DMF (1 drop) and then, following bubbling cessation, by addition of 3-(trifluoromethyl)pyridin-4-amine (201 mg, 1.239 mmol). After 10 minutes, the reaction mixture was concentrated, taken up in MeOH/DMSO, and purified by reverse phase chromatography eluting with 30-95% MeCN/ $H_2O$+0.1% TFA. Product fractions were lyophilized to yield the title compound. $^1$H NMR (CDCl$_3$) δ 8.1 (m, 3H), 8.50 (s, 1H), 7.75 (d, J=8.8 Hz, 1H), 7.49 (d, J=8.8 Hz, 1H), 7.55 (m, 2H), 7.41 (m, 1H), 7.27 (m, 1H), 7.07 (s, 1H), 5.60 (s, 2H). HRMS (M+1)=507.0363

Example 14

2-[[(3-{[5-chloro-4-(3-chloro-5-cyanophenoxy)-1H-1,2,3-benzotriazol-1-yl]methyl}-1H-pyrazolo[3,4-b]pyridin-1-yl)carbonyl](methyl)amino]ethanaminium chloride (Alternative name: N-(2-aminoethyl)-3-{[5-chloro-4-(3-chloro-5-cyanophenoxy)-1H-indazol-1-yl]methyl}-N-methyl-1H-pyrazolo[3,4-b]pyridine-1-carboxamide, HCl salt)

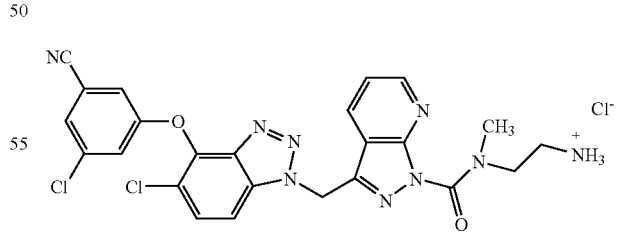

Step 1 tert-butyl {2-[[(3-{[5-chloro-4-(3-chloro-5-cyanophenoxy)-1H-1,2,3-benzotriazol-1-yl]methyl}-1H-pyrazolo[3,4-b]pyridin-1-yl)carbonyl](methyl)amino]ethyl}carbamate Pyridine (0.061 mL, 0.756 mmol) was added to a suspension of 3-chloro-5-{[5-chloro-1-(1H-pyrazolo[3,4-b]pyridin-3-ylmethyl)-1H-1,2,3-benzotriazol-4-yl]oxy}benzonitrile (165 mg, 0.378 mmol) in DCM (10 mL) at 0° C., followed by the addition in a single charge of triphosgene (45 mg, 0.151 mmol) as a solid, and then by the addition of diisopropyl ethylamine (0.198 mL, 1.135 mmol). This suspension was allowed to stir at 0° C. until a solution was achieved. 2-[(tert-Butoxycarbonyl)amino]-N-methylethanaminium chloride (120 mg, 0.567 mmol) was then added as a solid followed by diisopropyl ethylamine (0.198 mL, 1.135 mmol). The reaction mixture was allowed to warm to room temperature and after 10 minutes, the reaction mixture was diluted with dichloromethane (25 mL), washed with water (15 μL), and the aqueous layer was extracted with dichloromethane (25 mL). The combined organic fractions were dried (MgSO$_4$), filtered and concentrated. The resulting residue was purified by automated column chromatography on silica gel (12 g), eluting with 50-100% EtOAc/hexanes to afford the title compound. LRMS (M+1)=635.6.

Step 2: 2-[[(3-{[5-chloro-4-(3-chloro-5-cyanophenoxy)-1H-1,2,3-benzotriazol-1-yl]methyl}-1H-pyrazolo[3,4-b]pyridin-1-yl)carbonyl](methyl)amino]ethanaminium chloride Hydrochloric acid in dioxane (4 M, 5 mL) was added to tert-butyl {2-[[(3-{[5-chloro-4-(3-chloro-5-cyanophenoxy)-1H-1,2,3-benzotriazol-1-yl]methyl}-1H-pyrazolo[3,4-b]pyridin-1-yl)carbonyl](methyl)amino]ethyl}carbamate (620 mg, 974 mmol) at 0° C. After 2 hours, the reaction mixture was concentrated under reduced pressure and the residue crystallized from ethanol. $^1$H NMR (DMSO-d$_6$) δ 8.68 (d, J=4.5 Hz, 1H), 8.28 (d, J=8.0 Hz, 1H), 7.97 (d, J=9.1 Hz, 1H), 7.90 (s, 1H), 7.82 (m, 1H), 7.55 (m, 1H), 7.43 (m, 1H), 6.50 (s, 2H), 3.65 (m, 2H), 3.1 (m, 5H).

Example 15

Benzyl[5-chloro-4-(3-chloro-5-cyanophenoxy)-1H-1,2,3-benzotriazol-1-yl]acetate

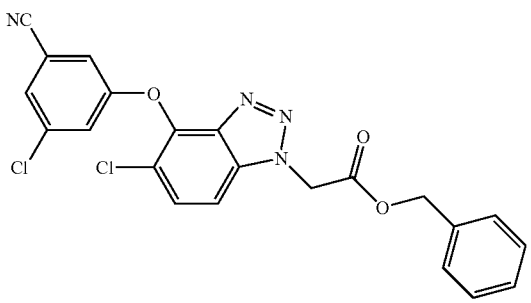

Lithium tert-butoxide (57.7 mg, 0.721 mmol) was added to 3-chloro-5-[(5-chloro-1H-1,2,3-benzotriazol-4-yl)oxy]benzonitrile (200 mg, 0.655 mmol) in DMF (2 mL). This reaction mixture was allowed to stir for 5 minutes, after which the mixture was cooled to 0° C. and benzyl bromoacetate was added dropwise and the mixture immediately allowed to warm to room temperature. After 30 minutes, the reaction was quenched with saturated aqueous ammonium chloride (2 mL) at 0° C., and the mixture was extracted with ethyl acetate (2×25 mL). The organic fractions were concentrated to 25 mL and washed with water (3×10 mL), dried (MgSO$_4$), filtered and the solvent was evaporated under reduced pressure. The resulting residue was purified by automated column chromatography on silica gel (12 g) eluting with 0-25% EtOAc/hexanes to afford the title compound. $^1$H NMR (DMSO-d$_6$) δ 7.92 (d, J=8.9 Hz, 1H), 7.84 (m, 1H), 7.82 (d, J=8.9 Hz, 1H), 7.58 (m, 1H), 7.52 (m, 1H), 7.37 (m, 5H), 5.90 (s, 2H), 5.20 (s, 2H). HRMS (M+1)=453.0516.

Example 16

1-{[5-chloro-4-(3-chloro-5-cyanophenoxy)-1H-1,2,3-benzotriazol-1-yl]acetyl}piperidine-3-carboxamide

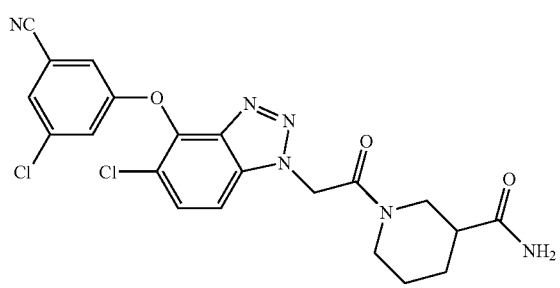

Step 1: tert-butyl[5-Chloro-4-(3-chloro-5-cyanophenoxy)-1H-1,2,3-benzotriazol-1-yl]acetate

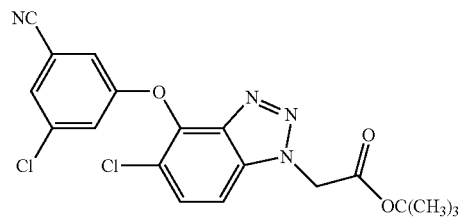

3-chloro-5-[(5-chloro-1H-1,2,3-benzotriazol-4-yl)oxy]benzonitrile (500 mg, 1.64 mmol) and cesium carbonate (534 mg, 1.64 mmol) were suspended in DMF (5 mL) under N$_2$. To this was added tert-butyl bromoacetate (336 mg, 1.72 mmol) After 1 hour, the reaction was quenched with saturated aqueous ammonium chloride (5 mL), diluted with water and the mixture extracted with ethyl acetate (2×25 mL). The combined organic fractions were washed with water (3×25 mL) and dried (MgSO$_4$), filtered and the solvent was evaporated under reduced pressure. The resulting residue was purified by automated column chromatography on silica gel (40 g) eluting with 0-15% EtOAc/hexanes to give the title product. LRMS (M+1)=418.9.

Step 2: [5-Chloro-4-(3-chloro-5-cyanophenoxy)-1H-1,2,3-benzotriazol-1-yl]acetic acid

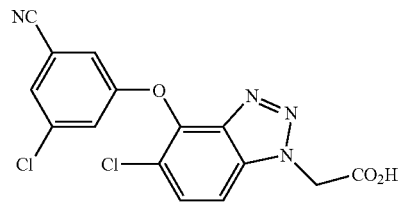

tert-Butyl[5-chloro-4-(3-chloro-5-cyanophenoxy)-1H-1,2,3-benzotriazol-1-yl]acetate (50 mg, 0.12 mmol) was dissolved in TFA (3 mL). After 1 hour, the reaction mixture was concentrated under reduced pressure to yield the title compound. $^1$H NMR (DMSO-d$_6$) δ 7.90 (d, J=8.9 Hz, 1H), 7.84 (m, 1H), 7.80 (d, J=8.9 Hz, 1H), 7.52 (m, 1H), 7.58 (m, 1H), 5.70 (s, 1H).

Step 3: 1-{[5-chloro-4-(3-chloro-5-cyanophenoxy)-1H-1,2,3-benzotriazol-1-yl]acetyl}piperidine-3-carboxamide

[5-chloro-4-(3-chloro-5-cyanophenoxy)-1H-1,2,3-benzotriazol-1-yl]acetic acid (13 mg, 0.036 mmol) (see step 2 in Example 16), piperidine-3-carboxamide (4.6 mg, 0.036 mmol), 3-{[(ethylimino)methylene]amino}-N,N-dimethylpropan-1-aminium chloride (6.9 mg, 0.036 mmol), 3H-[1,2,3]triazolo[4,5-b]pyridin-3-ol (4.9 mg, 0.036 mmol), and triethylamine (0.005 mL, 0.036 mmol) were dissolved in DMF (0.5 mL). After 1 hour, the reaction mixture was diluted with aqueous MeOH (1 mL) and purified by reverse phase chromatography eluting with 30-95% MeCN/H$_2$O+0.1% TFA. Product fractions were lyophilized to yield the title product. $^1$H NMR (DMSO-d$_6$) δ 7.84 (m, 1H), 7.77 (d, J=4.4 Hz, 1H), 7.76 (s, 2H), 7.58 (m, 1H), 7.51 (m, 1H), 7.44 (m, 1H), 7.36 (m, 1H), 7.02 (m, 1H), 6.84 (m, 1H), 5.97 (m, 2H), 5.93 (m, 1H), 5.87 (m, 0.5H), 5.83 (m, 0.25H), 4.29 (m, 2H), 3.80 (m, 4H), 3.40 (m, 1H), 3.10 (m, 1H), 2.95 (m, 1H), 2.65 (m, 1H), 2.20 (m, 1H), 1.90 (m, 2H), 1.70 (m, 4H), 1.40 (m, 1H). HRMS (M+1)=473.0867.

Example 17

(3-chloro-5-{[5-chloro-1-(1H-pyrazolo[3,4-b]pyridin-3-ylmethyl)-1H-1,2,3-benzotriazol-4-yl]oxy}phenyl)methanaminium trifluoroacetate (Alternative name: 1-(3-chloro-5-{[5-chloro-1-(1H-pyrazolo[3,4-b]pyridin-3-ylmethyl)-1H-1,2,3-benzotriazol-4-yl]oxy}phenyl)methanamine, TFA salt)

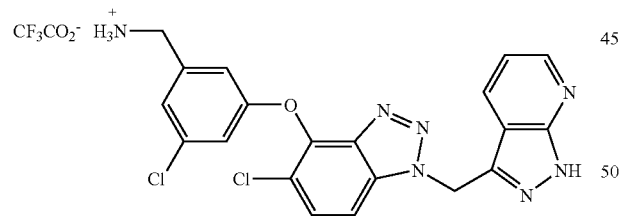

To 3-chloro-5-{[5-chloro-1-(1H-pyrazolo[3,4-b]pyridin-3-ylmethyl)-1H-1,2,3-benzotriazol-4-yl]oxy}benzonitrile (10 mg, 0.023 mmol) dissolved in dry THF (0.5 mL) at 0° C. was added LAH solution 1M in THF (0.046 mL, 0.046 mmol). After 30 minutes, the reaction mixture was quenched with EtOAc (2 mL) at 0° C. To this was added saturated aqueous Na$_2$SO$_4$ (0.25 mL). After 5 minutes, water (0.5 mL) was added. This mixture was allowed to stir for 5 minutes after which time solid excess Na$_2$SO$_4$ was added to the reaction mixture. This mixture was filtered and solvent removed under reduced pressure. The resulting residue was purified by reverse phase chromatography eluting with 30-95% MeCN/H$_2$O+0.1% TFA. Product fractions were lyophilized to afford the title compound. $^1$H NMR (DMSO-d$_6$) δ 8.54 (dd, J=4.5 Hz, J=1.4 Hz, 1H), 8.15 (dd, J=8.0 Hz, J=1.5 Hz, 1H), 8.15 (s, 3H), 7.90 (d, J=8.9 Hz, 1H), 7.80 (d, J=8.9 Hz, 1H), 7.32 (m, 1H), 7.22 (dd, J=8.0 Hz, 4.5 Hz, 1H), 7.17 (s, 2H), 6.38 (s, 2H), 4.00 (dd, J=11.4 Hz, J=5.6 Hz, 1H), Example 18

3-chloro-5-{[5-chloro-1-(1H-pyrazolo[3,4-b]pyridin-3-ylmethyl)-1H-1,2,3-benzotriazol-4-yl]oxy}benzaldehyde

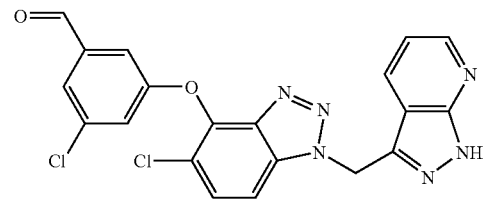

To 3-chloro-5-{[5-chloro-1-(1H-pyrazolo[3,4-b]pyridin-3-ylmethyl)-1H-1,2,3-benzotriazol-4-yl]oxy}benzonitrile (10 mg, 0.023 mmol) dissolved in dry THF (0.5 mL) at 0° C. was added LAH solution 1M in THF (0.046 mL, 0.046 mmol). After 30 minutes, the reaction was quenched with EtOAc (2 mL) at 0° C., followed by addition of saturated aqueous Na$_2$SO$_4$ (0.25 mL), and then after 5 minutes by addition of water (0.5 mL). This mixture was allowed to stir for 5 minutes after which time solid Na$_2$SO$_4$ was added to the reaction mixture. The dried mixture was then filtered and solvent removed under reduced pressure. The resulting residue was purified by reverse phase chromatography eluting with 30-95% MeCN/H$_2$O+0.1% TFA. Product fractions were lyophilized to afford the title compound. $^1$H NMR (DMSO-d$_6$) δ 9.90 (s, 1H), 8.52 (d, J=3.5 Hz), 8.10 (d, J=7.5 Hz), 7.90 (d, J=8.9 Hz, 1H), 7.80 (d, J=8.9 Hz, 1H), 7.72 (m, 1H), 7.30 (m, 1H), 7.20 (dd, J=8.1 Hz, J=4.6 Hz, 1H), 6.40 (s, 2H).

Example 19

2,5-dichloro-3-{[5-chloro-1-(1H-pyrazolo[3,4-b]pyridin-3-ylmethyl)-1H-1,2,3-benzotriazol-4-yl]oxy}benzonitrile

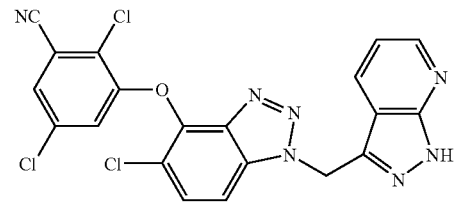

Step 1: 1-bromo-2,5-dichloro-3-methoxybenzene

Methanol (5 mL) was added to potassium tert-butoxide (3.94 g, 123 mmol) suspended in toluene/DMPU (3:1, 240 mL), and the mixture was placed in an oil bath at 80° C. under N$_2$ with a reflux condenser for 25 minutes to obtain a solution. The solution was then allowed to cool to room temperature under N$_2$, after which 1-bromo-2,5-dichloro-3-fluorobenzene (10 g, 41 mmol) was added dropwise to the solution and the resulting suspension was placed in an oil bath at 80° C. under $N_2$. After 4 hours, the reaction mixture was allowed to cool to room temperature and was then diluted with hexanes (200 mL) and water (100 mL). The layers were separated and the aqueous layer was extracted with hexanes (200 mL). The combined organic portions were washed with water (3×300 mL), dried ($MgSO_4$), filtered and concentrated to give the title compound. $^1$H NMR ($CDCl_3$) δ 7.20 (m, 1H), 6.80 (m, 1H), 3.90 (s, 3H).

Step 2: 3-bromo-2,5-dichlorophenol

Boron tribromide as a 1 M solution in dichloromethane (41 mL, 41 mmol) was added to 1-bromo-2,5-dichloro-3-methoxybenzene (10.5 g, 41 mmol) in dichloromethane (100 mL) at −78° C. under $N_2$. The reaction mixture was allowed to warm to room temperature, and after 21 hours, the mixture was poured into 100 g of ice, diluted with 100 g of water, and the organic layer separated. The aqueous layer was extracted with dichloromethane (200 mL) and the combined organic extracts were dried ($MgSO_4$), filtered and the solvent was evaporated under reduced pressure. $^1$H NMR ($CDCl_3$) δ 7.20 (m, 1H), 7.00 (m, 1H), 5.70 (s, 1H).

Step 3: 1-bromo-2,5-dichloro-3-(2-chloro-6-nitrophenoxy)benzene 3-bromo-2,5-dichlorophenol (8.0 g, 33 mmol) and 2,3-dichloronitrobenzene (6.4 g, 33 mmol) were dissolved in NMP (30 mL), followed by the addition of potassium carbonate (5.5 g, 40 mmol). The resulting suspension was placed in an oil bath at 120° C. for 7 hours, after which the reaction mixture was diluted with water (150 mL) and extracted with ethyl acetate (2×00 mL). The combined organic fractions were washed with water (3×100 mL), dried ($MgSO_4$), filtered and the solvent was evaporated under reduced pressure. The resulting residue was purified by column chromatography on silica gel (330 g) eluting with 0-20% $CH_2Cl_2$/hexanes to afford the title compound. $^1$H NMR ($CDCl_3$) δ 7.98 (dd, J=8.2 Hz, J=1.6 Hz, 1H), 7.79 (dd, J=8.2 Hz, J=1.6 Hz, 1H), 7.44 (dd, J=8.2 Hz, J=8.2 Hz, 1H), 7.40 (d, J=2.2 Hz, 1H), 6.54 (d, J=2.2 Hz, 1H).

Step 4: 3-(3-bromo-2,5-dichlorophenoxy)-4-chloro-2-nitroaniline 1,1,1-trimethylhydrazinium iodide (14.7 g, 72.7 mmol) was added to potassium tert-butoxide (8.20 g, 72.7 mmol) and copper (I) chloride (0.180 g, 1.82 mmol) in DMF (50 mL) at 0° C. The resulting mixture was allowed to stir for several minutes at which point the mixture was cooled to −40° C. and 1-bromo-2,5-dichloro-3-(2-chloro-6-nitrophenoxy)benzene (7.23 g, 18.2 mmol) as a solution in DMF (50 mL) was added dropwise. The reaction mixture was then maintained at −40° C. for 20 minutes, at which point the reaction was quenched at −40° C. with saturated aqueous ammonium chloride (10 mL). Water (10 mL) was then added and the mixture was allowed to warm to room temperature. The mixture was extracted with ethyl acetate (2×200 mL). The combined organic fractions were washed with water (3×200 mL), dried ($MgSO_4$) and the solvent was evaporated under reduced pressure. The resulting residue was purified by automated column chromatography on silica gel (1.5 kg) eluting with 25% EtOAc/hexanes to give the title compound. LRMS (M+1)=412.4.

Step 5: 3-(3-bromo-2,5-dichlorophenoxy)-4-chlorobenzene-1,2-diamine 3-(3-bromo-2,5-dichlorophenoxy)-4-chloro-2-nitroaniline (2.68 g, 6.50 mmol) and tin(II) chloride dihydrate (7.33 g, 32.5 mmol) were suspended in MeOH (50 mL) and heated to 75° C. under a reflux condenser and $N_2$. After 11 hours, the reaction mixture was allowed to cool to room temperature, and concentrated under reduced pressure. The resulting residue was diluted with ethyl acetate (150 mL), after which 10% aqueous sodium carbonate (250 mL) was added with vigorous stirring until the pH was 10. The resulting suspension was filtered through celite, the filtrate was extracted with ethyl acetate. The combined organic fractions were dried ($MgSO_4$), filtered and the solvent was evaporated under reduced pressure to yield the title compound. LRMS (M+1)=382.5.

Step 6: 4-(3-bromo-2,5-dichlorophenoxy)-5-chloro-1H-1,2,3-benzotriazole 3-(3-bromo-2,5-dichlorophenoxy)-4-chlorobenzene-1,2-diamine (2.48 g, 6.47 mmol) in acetic acid (20 mL) was cooled to 15° C., after which sodium nitrite (0.446 g, 6.47 mmol) in water (6.47 mL) was added dropwise under $N_2$. After 1.5 hours, the reaction mixture was diluted with EtOAc (200 mL), and the organic phase was separated and washed with water (3×75 mL). The organic phase was dried ($MgSO_4$), filtered, concentrated and placed under vacuum to yield the title compound. LRMS (M+1)=393.4.

Step 7: 2,5-dichloro-3-[(5-chloro-1H-1,2,3-benzotriazol-4-yl)oxy]benzonitrile 4-(3-bromo-2,5-dichlorophenoxy)-5-chloro-1H-1,2,3-benzotriazole (2.55 g, 6.49 mmol), tetrakis triphenylphosphine palladium(0) (2.25 g, 1.95 mmol) and zinc cyanide (0.915 g, 7.79 mmol) were suspended in dry DMF (50 mL) under $N_2$ and placed in an oil bath at 90° C. for 24 hours, after which the reaction mixture was allowed to cool to room temperature. The cooled mixture was then diluted with EtOAc (200 mL) and washed with water (4×100 mL), the aqueous layer was extracted with EtOAc (100 mL) and then washed with water (4×50 mL). The combined organic extracts were dried ($MgSO_4$), filtered and concentrated with silica gel. The concentrate was purified by automated column chromatography on silica gel (40 g) eluting with 0-30% EtOAc/hexanes to afford the title compound. LRMS (M+1)=340.16.

Step 8: tert-butyl 3-{[5-chloro-4-(2,5-dichloro-3-cyanophenoxy)-1H-1,2,3-benzotriazol-1-yl]methyl}-1H-pyrazolo[3,4-b]pyridine-1-carboxylate

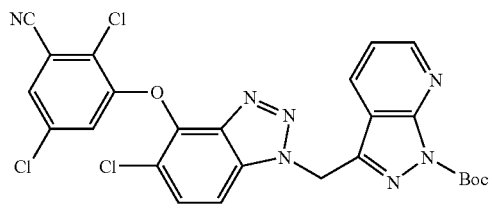

2,5-dichloro-3-[(5-chloro-1H-1,2,3-benzotriazol-4-yl)oxy]benzonitrile (1.00 g, 2.94 mmol) and cesium carbonate (1.15 g, 3.53 mmol) were suspended in dry DMF (10 mL)

under $N_2$ and tert-butyl 3-(bromomethyl)-1H-pyrazolo[3,4-b]pyridine-1-carboxylate (0.965 g, 3.09 mmol) was added as a solution in DMF (5 mL) at room temperature. After 1 hour, the reaction mixture was quenched with saturated aqueous ammonium chloride (20 mL) and diluted with water (50 mL). The mixture was then extracted with ethyl acetate (2×100 mL). The combined organic fractions were washed with water (3×100 mL), dried ($MgSO_4$), filtered and the solvent was evaporated under reduced pressure. The resulting residue was purified by automated column chromatography on silica gel (120 g) eluting with 25-50% EtOAc/hexanes. LRMS (M+1)=569.6.

Step 9: 2,5-dichloro-3-{[5-chloro-1-(1H-pyrazolo[3,4-b]pyridin-3-ylmethyl)-1H-1,2,3-benzotriazol-4-yl]oxy}benzonitrile tert-Butyl 3-{[5-chloro-4-(2,5-dichloro-3-cyanophenoxy)-1H-1,2,3-benzotriazol-1-yl]methyl}-1H-pyrazolo[3,4-b]pyridine-1-carboxylate (569 mg, 0.997 mmol) was dissolved in TFA (5 mL). After 20 minutes, the reaction mixture was concentrated under reduced pressure, and the resulting residue was purified by reverse phase chromatography eluting with 30-95% $MeCN/H_2O$+0.1% TFA. Product fractions concentrated under reduced pressure to yield the title compound. $^1$H NMR (DMSO-$d_6$) δ 8.53 (dd, J=4.4 Hz, J=1.6 Hz, 1H), 8.14 (dd, J=8.0 Hz, J=1.5 Hz, 1H), 8.04 (d, J=0.6 Hz, 1H), 7.89 (d, J=8.9 Hz, 1H), 7.79 (d, J=8.9 Hz, 1H), 7.44 (d, J=0.6 Hz, 1H), 7.21 (dd, J=8.0 Hz, J=4.5 Hz, 1H), 6.38 (d, 2H). HRMS (M+1)=470.0076

Example 20

2,5-dichloro-3-{[5-chloro-2-(1H-pyrazolo[3,4-b]pyridin-3-ylmethyl)-2H-1,2,3-benzotriazol-4-yl]oxy}benzonitrile

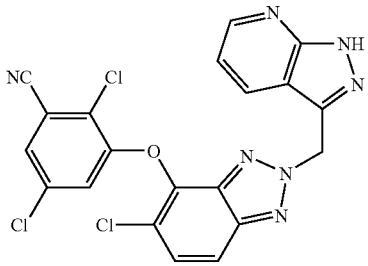

Step 1: tert-butyl 3-{[5-chloro-4-(2,5-dichloro-3-cyanophenoxy)-2H-1,2,3-benzotriazol-2-yl]methyl}-1H-pyrazolo[3,4-b]pyridine-1-carboxylate 2,5-dichloro-3-[(5-chloro-1H-1,2,3-benzotriazol-4-yl)oxy]benzonitrile (1.00 g, 2.94 mmol) and cesium carbonate (1.15 g, 3.53 mmol) were suspended in dry DMF (10 mL) under $N_2$, and tert-butyl 3-(bromomethyl)-1H-pyrazolo[3,4-b]pyridine-1-carboxylate (0.965 g, 3.09 mmol) was added as a solution in DMF (5 mL) at room temperature. After 1 hour, the reaction mixture was quenched with saturated aqueous ammonium chloride (20 mL), diluted with water (50 mL), and the mixture extracted with EtOAc (2×100 mL). The combined organic fractions were washed with water (3×100 mL), dried ($MgSO_4$), filtered and the solvent was evaporated under reduced pressure. The resulting residue was purified by automated column chromatography on silica gel (120 g) eluting with 25-50% EtOAc/hexanes. LRMS (M+1)=569.6.

Step 2: 2,5-dichloro-3-{[5-chloro-2-(1H-pyrazolo[3,4-b]pyridin-3-ylmethyl)-2H-1,2,3-benzotriazol-4-yl]oxy}benzonitrile tert-butyl 3-{[5-chloro-4-(2,5-dichloro-3-cyanophenoxy)-2H-1,2,3-benzotriazol-2-yl]methyl}-1H-pyrazolo[3,4-b]pyridine-1-carboxylate (100 mg, 0.175 mmol) was dissolved in TFA (5 mL) at room temperature. After 20 minutes, the reaction mixture was concentrated under reduced pressure, and the resulting residue was purified by reverse phase chromatography eluting with 30-95% $MeCN/H_2O$+0.1% TFA. The product fractions were concentrated under reduced pressure to yield the title compound. $^1$H NMR (DMSO-$d_6$) δ 13.80 (s, 1H), 8.44 (d, J=2.9 Hz, 1H), 7.99 (d, J=2.2 Hz), 7.95 (m, 1H), 7.93 (d, J=9.2 Hz, 1H), 7.62 (d, J=9.2 Hz, 1H), 7.35 (d, J=2.3 Hz, 1H), 7.16 (dd, J=8.0 Hz, J=4.6 Hz, 1H), 6.30 (s, 2H). HRMS (M+1)=470.0076.

Example 21

1-(2,5-dichloro-3-{[5-chloro-1-(1H-pyrazolo[3,4-b]pyridin-3-ylmethyl)-1H-1,2,3-benzotriazol-4-yl]oxy}phenyl)methanamine

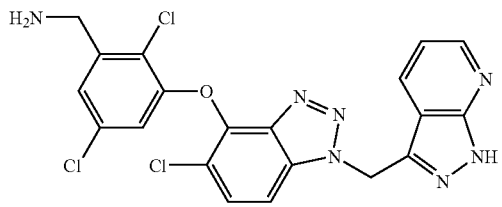

2,5-dichloro-3-{[5-chloro-1-(1H-pyrazolo[3,4-b]pyridin-3-ylmethyl)-1H-1,2,3-benzotriazol-4-yl]oxy}benzonitrile (283 mg, 0.601 mmol) was dissolved in dry THF (30 mL), cooled to 0° C., and LAH solution (1.20 mL, 1.20 mmol) in THF (1.2 mL) was added. The reaction mixture was allowed to warm to room temperature, and after 2 hours the mixture was cooled to 0° C. and quenched with EtOAc (50 mL). To this mixture was added saturated aqueous $Na_2SO_4$ (3 mL), followed 5 minutes later by the addition of water (5 mL). This mixture was stirred for 5 minutes after which excess solid $Na_2SO_4$ was added. The mixture was then filtered and solvent removed under reduced pressure. The resulting residue was purified by reverse phase chromatography eluting with 5-95% $MeCN/H_2O$+0.1% TFA to yield the title compound. $^1$H NMR (DMSO-$d_6$) δ 8.53 (d, J=4.5 Hz, 1H), 8.12 (d, J=8.0 Hz, 1H), 7.98 (s, 2H), 7.89 (d, J=9.0 Hz, 1H), 7.79 (d, J=9.0 Hz, 1H), 7.48 (s, 1H), 7.20 (dd, J=8.0 Hz, J=4.5 Hz, 1H), 6.91 (s, 1H), 6.38 (s, 2H), 4.21 (s, 2H). HRMS (M+1)=476.0363.

Example 22

3-({1-[(6-amino-1H-pyrazolo[3,4-b]pyridin-3-yl)methyl]-5-chloro-1H-1,2,3-benzotriazol-4-yl}oxy)-2,5-dichlorobenzonitrile

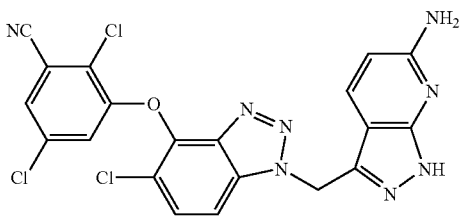

Step 1: 2,5-dichloro-3-{[5-chloro-1-({1-(4-methoxybenzyl)-6-[(4-methoxybenzyl)amino]-1H-pyrazolo[3,4-b]pyridin-3-yl}methyl)-1H-1,2,3-benzotriazol-4-yl]oxy}benzonitrile

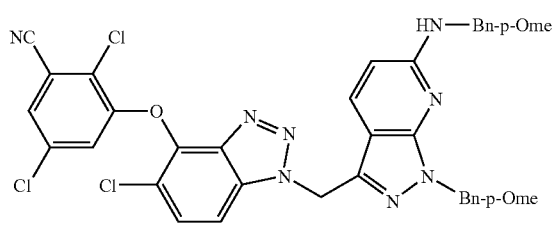

2,5-dichloro-3-[(5-chloro-1H-1,2,3-benzotriazol-4-yl)oxy]benzonitrile (90 mg, 0.265 mmol) and lithium tert-butoxide (22 mg, 0.278 mmol) were dissolved in DMF (1 mL) and the solution stirred for 5 minutes at room temperature. The reaction mixture was cooled to 0° C. and 3-(chloromethyl)-N,1-bis(4-methoxybenzyl)-1H-pyrazolo[3,4-b]pyridin-6-amine (112 mg, 0.265 mmol) in DMF (1.5 mL) was added. After the addition, the solution was allowed to warm to room temperature and stirred for 16 hours, after which saturated aqueous ammonium chloride (1 mL) was added and the mixture was extracted with ethyl acetate (2×15 mL). The combined organic fractions were washed with water (3×15 mL). The combined aqueous layers were back-extracted with EtOAc (25 mL) and the extracts subsequently washed with water (3×15 mL). The combined organic fractions were dried (MgSO$_4$), filtered and the solvent was evaporated under reduced pressure. The resulting residue was purified by column chromatography on silica gel (12 g) eluting with 0-40% EtOAc/hexanes to afford the title compound. LRMS (M+1)=726.3.

Step 2: 3-({1-[(6-amino-1H-pyrazolo[3,4-b]pyridin-3-yl)methyl]-5-chloro-1H-1,2,3-benzotriazol-4-yl}oxy)-2,5-dichlorobenzonitrile 2,5-dichloro-3-{[5-chloro-1-({1-(4-methoxybenzyl)-6-[(4-methoxybenzyl)amino]-1H-pyrazolo[3,4-b]pyridin-3-yl}methyl)-1H-1,2,3-benzotriazol-4-yl]oxy}benzonitrile (60 mg, 0.083 mmol) was dissolved in TFA and heated to 75° C. After 1 hour, the reaction mixture was concentrated under reduced pressure and re-constituted in EtOAc (15 mL). The reconstituted mixture was then washed with saturated aqueous sodium carbonate (5 mL) and then with water (5 mL). The combined aqueous layers were back-extracted with EtOAc (15 μL). The combined organic fractions were dried (MgSO$_4$), filtered and solvent removed under reduced pressure. The resulting residue was purified by column chromatography on silica gel (4 g) eluting with 0-10% MeOH/CH$_2$Cl$_2$ to yield the title compound. $^1$H NMR (DMSO-d$_6$) δ 12.70 (s, 1H), 8.04 (d, J=2.3 Hz, 1H), 7.81 (d, J=8.9 Hz, 1H), 7.76 (d, J=8.9 Hz, 1H), 7.53 (d, J=8.6 Hz, 1H), 7.41 (d, J=2.3 Hz, 1H), 6.36 (s, 2H), 6.29 (d, J=8.7 Hz, 1H), 6.15 (s, 2H), 5.75 (s, 1H). HRMS (M+1)=485.0193.

Example 23

3-chloro-5-({5-chloro-1-[(5-phenyl-1,3,4-oxadiazol-2-yl)methyl]-1H-1,2,3-benzotriazol-4-yl}oxy)benzonitrile

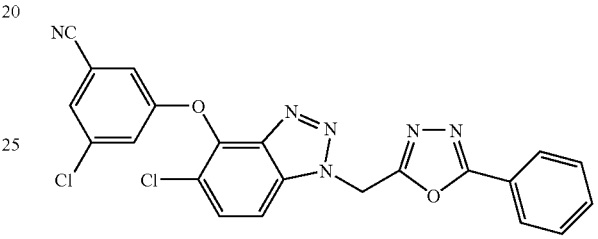

3-chloro-5-[(5-chloro-1H-1,2,3-benzotriazol-4-yl)oxy]benzonitrile (100 mg, 0.328 mmol), cesium carbonate (107 mg, 0.328 mmol) and 2-(chloromethyl)-5-phenyl-1,3,4-oxadiazole (64 mg, 0.328 mmol) were combined and suspended in DMF (2 mL). After 16 hours at room temperature, the reaction mixture was quenched with saturated aqueous ammonium chloride (1 mL) and extracted with EtOAc (2×25 mL). The combined organic fractions were evaporated under reduced pressure, and the resulting residue was purified by reverse phase chromatography eluting with 30-95% MeCN/H$_2$O+0.1% TFA. The product fractions were concentrated to yield the title compound. $^1$H NMR (DMSO-d$_6$) δ 8.01 (d, J=8.9 Hz, 1H), 7.96 (d, J=8.3 Hz, 2H), 7.88 (d, J=8.9 Hz, 1H), 7.83 (m, 1H), 7.61 (m, 5H), 6.54 (s, 2H). HRMS (M+1)=463.0465.

Example 24

3-chloro-5-({5-chloro-2-[(5-phenyl-1,3,4-oxadiazol-2-yl)methyl]-2H-1,2,3-benzotriazol-4-yl}oxy)benzonitrile

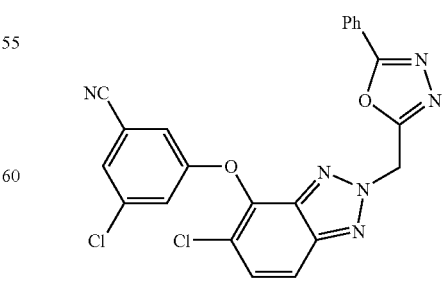

3-chloro-5-[(5-chloro-1H-1,2,3-benzotriazol-4-yl)oxy]benzonitrile (100 mg, 0.328 mmol), cesium carbonate (107 mg, 0.328 mmol) and 2-(chloromethyl)-5-phenyl-1,3,4-oxadiazole (64 mg, 0.328 mmol) were combined and suspended in DMF (2 mL). After 16 hours, the reaction mixture was quenched with saturated aqueous ammonium chloride (1 mL) and extracted with EtOAc (2×25 mL). The combined organic fractions were evaporated under reduced pressure. The resulting residue was purified by reverse phase chromatography eluting with 30-95% MeCN/H$_2$O+0.1% TFA. The product fractions were concentrated to yield the title compound. $^1$H NMR (DMSO-d$_6$) δ 8.01 (d, J=9.1 Hz, 1H) 7.92 (d, J=8.6 Hz, 2H), 7.72 (m, 1H), 7.68 (m, 1H), 7.60 (m, 5H), 6.50 (s, 1H). HRMS (M+1)=463.0464.

Example 25

3-chloro-5-{[7-methyl-3-(1H-pyrazolo[3,4-b]pyridin-3-ylmethyl)imidazo[1,5-a]pyridin-8-yl]oxy}benzonitrile trifluoroacetate (Alternative name: 3-chloro-5-{[7-chloro-3-(1H-pyrazolo[3,4-b]pyridin-3-ylmethyl)imidazo[1,5-a]pyridin-8-yl]oxy}benzonitrile, TFA salt)

TFA salt of:

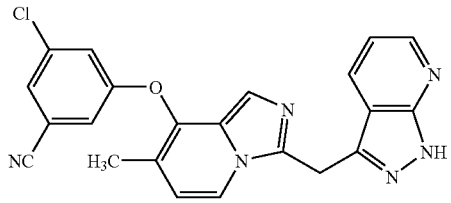

Step 1: 3-fluoro-4-methylpyridine-2-carbonitrile

To a mixture of 2-bromo-3-bromo-4-methylpyridine (4.89 g, 25.7 mmol) and zinc cyanide (3.02 g, 25.7 mmol) in DMF (45 mL) was added palladium tetra(triphenylphosphine) (2.97 g, 2.57 mmol). The mixture was degassed and then heated at 90° C. for 18 hours, after which the mixture was diluted with water (500 mL) and EtOAc (500 mL), filtered, and the resulting layers were separated. The aqueous layer was further extracted with EtOAc (2×500 mL), and the combined extracts were washed with water (300 mL), dried over MgSO$_4$, filtered, and the solvent removed in vacuo. The resulting residue was chromatographed using RediSep column (330 g) and eluting with a gradient of 0-100% EtOAc/CH$_2$Cl$_2$. The pure fractions were combined and the solvent removed in vacuo to give title compound.

$^1$H NMR (CDCl$_3$): δ 8.39 (d, 1H, J=4.7 Hz), 7.41 (m, 1H) and 2.41 (s, 3H) ppm.

Step 2: 3-(3-bromo-5-chlorophenoxy)-4-methylpyridine-2-carbonitrile

A mixture of 3-fluoro-4-methylpyridine-2-carbonitrile (2.1 g, 15.43 mmol), 3-bromo-5-chlorophenol (3.68 g, 17.74 mmol) and cesium carbonate (5.03 g, 15.43 mmol) in DMF (30 mL) was heated at 70° C. for 1 hour and then at 80° C. for another hour, after which the mixture was partitioned between water (300 mL) and ethyl acetate (2×500 mL). The combined extracts were washed with water (100 mL) and then brine (100 mL), dried over MgSO$_4$, filtered, and the solvent removed in vacuo. The residue was chromatographed using RediSep column (330 g) and eluted with a gradient of 0-10% EtOAc/CH$_2$Cl$_2$ and the pure fractions combined and concentrated on the rotary evaporator to give the title compound. LRMS (M+1)=324.9.

Step 3: 1-[3-(3-bromo-5-chlorophenoxy)-4-methylpyridin-2-yl]methanamine

To a solution of 3-(3-bromo-5-chlorophenoxy)-4-methylpyridine-2-carbonitrile (570 mg, 1.762 mmol) in tetrahydrofuran (7 mL) cooled over dry ice/acetone bath was added 2M LAH in THF (1.233 mL, 2.466 mmol) and the mixture stirred over dry ice-acetone bath for 40 minutes. After this time, the dry ice-acetone bath was replaced with a wet ice bath and mixture stirred for 5 minutes. The mixture was then treated with water (94 µL), 1.0N NaOH (94 µL) and more water (280 µL), and then stirred at room temperature for 30 minutes. After this time, the mixture was diluted with THF (7 mL) and filtered through celite. The solids were washed with additional THF (10 mL). The filtrates were combined, the solvent removed under vacuum, and the residue purified using Waters PrepPak and eluting with a gradient of 5-95% ACN/H$_2$O with 0.1% TFA. The desired fractions were combined and the solvent removed in vacuo to give the title compound. LRMS (M+1)=328.9.

Step 4: {[3-(3-bromo-5-chlorophenoxy)-4-methylpyridin-2-yl]methyl}-2-(1H-pyrazolo[3,4-b]pyridin-3-yl)acetamide

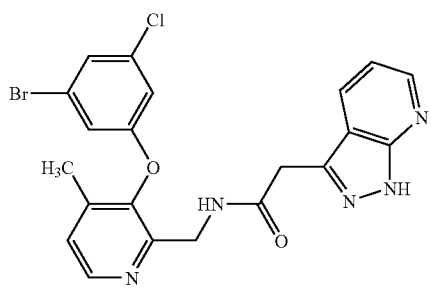

To a solution of 1-[3-(3-bromo-5-chlorophenoxy)-4-methylpyridin-2-yl]methanamine (125 mg, 0.382 mmol), 1H-pyrazolo[3,4-b]pyridin-3-ylacetic acid compound with ammonium chloride (1:1), (102 mg, 0.443 mmol), HOAT (5.2 mg, 0.038 mmol) and TEA (53 µL, 0.382 mmol) in DMF (2 mL) was added EDC (80 mg, 0.42 mmol), and the mixture was stirred for 2.2 hours. The mixture was then filtered and purified using Waters PrepPak column and eluting with a gradient of 5-95% ACN/H$_2$O with 0.1% TFA. The desired fractions were lyophilized to give title compound.

LRMS (M+1)=487.7.

Step 5: 3-{[8-(3-bromo-5-chlorophenoxy)-7-methylimidazo[1,5-a]pyridin-3-yl]methyl}-1H-pyrazolo[3,4-b]pyridine

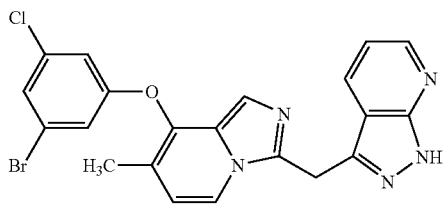

To a suspension of N-{[3-(3-bromo-5-chlorophenoxy)-4-methylpyridin-2-yl]methyl}-2-(1H-pyrazolo[3,4-b]pyridin-3-yl)acetamide (77 mg, 0.158 mmol) in toluene (2 mL) was added phosphorus oxychloride (120 μL, 0.79 mmol). The resulting mixture was then heated at 100° C. for 1 hour, after which the solvent was removed in vacuo and the residue was stirred with $CH_2Cl_2$ (50 mL) and saturated aqueous $Na_2CO_3$ (30 mL) for 30 minutes. The layers were partitioned and the organic extract was dried over $MgSO_4$, filtered and the solvent removed in vacuo. This residue was purified using RediSep column (12 g) eluting with a gradient of 0-10% $MeOH/CH_2Cl_2$. The pure fractions were combined and the solvent removed in vacuo to give the title compound. LRMS (M+1)=469.7.

Step 6: 3-chloro-5-{[7-methyl-3-(1H-pyrazolo[3,4-b]pyridin-3-ylmethyl)imidazo[1,5-a]pyridin-8-yl]oxy}benzonitrile trifluoroacetate To a suspension of 3-{[8-(3-bromo-5-chlorophenoxy)-7-methylimidazo[1,5-a]pyridin-3-yl]methyl}-1H-pyrazolo[3,4-b]pyridine (44 mg, 0.094 mmol) and zinc cyanide (12.12 mg, 0.103 mmol) in DMF (1 mL) was added palladium tetratriphenylphosphine (21.7 mg, 0.019 mmol), and the resulting mixture was heated at 90° C. for 2 hours. The mixture was then cooled to room temperature and purified on a Luna column (10μ, C18, 250×21.2 cm) eluting with 5-95% ACN/water with 0.1% TFA to give the title compound. $^1$H NMR ($CD_3OD$): δ 8.54 (d, 1H, J=4 Hz), 8.25 (d, 1H, J=7 Hz), 8.19 (d, 1H, J=8 Hz), 7.56 (dd, 1H, J=1.5 Hz), 7.50 (s, 1H), 7.38 (dd, 1H, J=1.5 Hz), 7.30 (dd, 1H, J=1.5 Hz), 7.24 (dd, 1H, J=4 and 8 Hz), 6.96 (d, 1H, J=7 Hz), 5.01 (s, 2H) and 2.20 (s, 3H) ppm. LRMS (M+1)=414.9.

Example 26

3-chloro-5-{[7-methyl-3-(1H-pyrazolo[3,4-b]pyridin-3-ylmethyl)[1,2,4]triazolo[4,3-a]pyridin-8-yl]oxy}benzonitrile trifluoroacetate (Alternative name: 3-chloro-5-{[7-methyl-3-(1H-pyrazolo[3,4-b]pyridin-3-ylmethyl)[1,2,4]triazolo[4,3-a]pyridin-8-yl]oxy}benzonitrile, TFA salt)

TFA salt of:

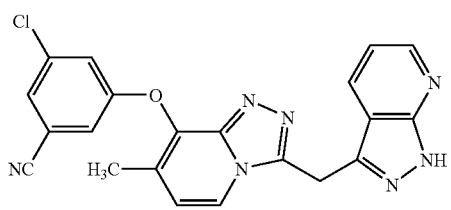

Step 1: 3-(3-bromo-5-chlorophenoxy)-4-methylpyridine-2-carboxylic acid

A suspension of 3-(3-bromo-5-chlorophenoxy)-4-methylpyridine-2-carbonitrile (5 g, 15.45 mmol) in concentrated HCl (30 mL) was heated at 100° C. for 3 hours and then at 120° C. for an additional 1.5 hours. This suspension was cooled to 50° C. and the resulting white solid was filtered, washed with water (10 mL), and dried under high vacuum to give the title compound. LRMS (M+1)=343.8.

Step 2: 3-(3-bromo-5-chlorophenoxy)-4-methylpyridin-2-amine

To a suspension of 3-(3-bromo-5-chlorophenoxy)-4-methylpyridine-2-carboxylic acid (2 g, 5.84 mmol) in THF (12 mL) was added TEA (1.627 mL, 11.68 mmol), pyridine (944 ul, 11.68 mmol), t-butanol (2.79 mL, 29.2 mmol) and diphenylphosphoryl azide (1.89 mL, 8.76 mmol). The resulting mixture was heated to 65° C. for 35 minutes, after which the mixture was diluted with $CH_2Cl_2$ (2×100 mL) and washed with water (100 mL). The combined organic extracts were concentrated in vacuo, and the resulting residue was dissolved in TFA (20 mL) and allowed to stand for 15 minutes. After this time, the solvent was removed in vacuo and the residue was partitioned between saturated aqueous $NaHCO_3$ (50 mL) and $CH_2Cl_2$ (100 mL). The organic extract was concentrated on the rotary evaporator and the residue was purified using a RediSep column (330 g) eluting with a gradient of 0-30% $EtOAc/CH_2Cl_2$ to give the title compound. LRMS (M+1)=314.9.

Step 3: 3-(3-bromo-5-chlorophenoxy)-4-methylpyridin-2-ol

To an ice cooled suspension of 3-(3-bromo-5-chlorophenoxy)-4-methylpyridin-2-amine (600 mg, 1.913 mmol) in 5% aqueous $H_2SO_4$ (10 mL) was added a solution of sodium nitrite (198 mg, 2.87 mmol) in water (1 mL). The suspension was stirred in an ice bath for 30 minutes, after which it was added to a solution of 5% aqueous $H_2SO_4$ (10 mL), and the mixture was warmed to 100° C. and maintained at 100° C. for 1.5 hours. After this time, the mixture was cooled to 0° C. and treated with additional sodium nitrite (60 mg, 0.86 mmol) and then heated at 100° C. for 20 minutes. After this time, the mixture was cooled to 25° C., the resulting solid was collected by filtration, washed with water (10 mL), and dried under high vacuum to give the title compound. HRMS (M+1)=313.9577.

Step 4: 3-(3-bromo-5-chlorophenoxy)-2-chloro-4-methylpyridine

A suspension of 3-(3-bromo-5-chlorophenoxy)-4-methylpyridin-2-ol (340 mg, 1.081 mmol) in phosphorus oxychloride (10 mL, 107 mmol) was heated at 100° C. for 24 hours, after which the solvent was removed in vacuo. The resulting oil was quenched with saturated aqueous $NaHCO_3$ (50 mL) and extracted with EtOAc (100 mL). The organic extract was washed with water (20 mL), dried over $MgSO_4$, filtered, and the solvent removed on a rotary evaporator. This residue was purified using Waters PrepPak and eluting with a gradient of 5-95% $ACN/H_2O$ with 0.1% TFA. The desired fractions were combined and the solvent removed in vacuo to give the title compound. LRMS (M+1)=333.8.

Step 5: 3-(3-bromo-5-chlorophenoxy)-2-hydrazino-4-methylpyridine

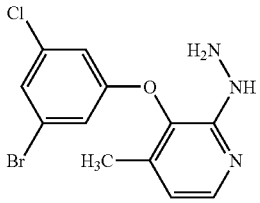

To a solution of 3-(3-bromo-5-chlorophenoxy)-2-chloro-4-methylpyridine (121 mg, 0.363 mmol) in DMSO (1 mL) was added hydrazine hydrate (177 μL, 3.63 mmol) and the mixture was heated at 100° C. for 18 hours. The mixture was then purified on a Luna column (10μ, C18, 250×21.2 cm) eluting with 5-95% ACN/water with 0.1% TFA to give the title compound. LRMS (M+1)=329.8.

Step 6: N'-[3-(3-bromo-5-chlorophenoxy)-4-methylpyridin-2-yl]-2-(1H-pyrazolo[3,4-b]pyridin-3-yl)acetohydrazide

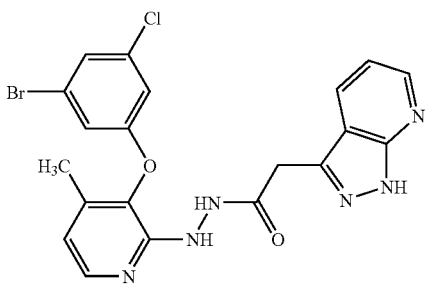

To a solution of 3-(3-bromo-5-chlorophenoxy)-2-hydrazino-4-methylpyridine trifluoroacetate (112 mg, 0.253 mmol), 1H-pyrazolo[3,4-b]pyridin-3-ylacetic acid compound with ammonium chloride (1:1), (67.6 mg, 0.253 mmol), HOAT (6.89 mg, 0.051 mmol) and TEA (106 μL, 0.759 mmol) in DMF (1 mL) was added EDC (58.2 mg, 0.304 mmol) and the resulting mixture was stirred for 2 hours. The mixture was then filtered and purified on a Luna column (10μ, C18, 250×21.2 cm) eluting with 5-95% ACN/water with 0.1% TFA to give the title compound.
HRMS (M+1)=487.0278.

Step 7: 8-(3-bromo-5-chlorophenoxy)-7-methyl-3-(1H-pyrazolo[3,4-b]pyridin-3-ylmethyl)[1,2,4]triazolo[4,3-a]pyridine

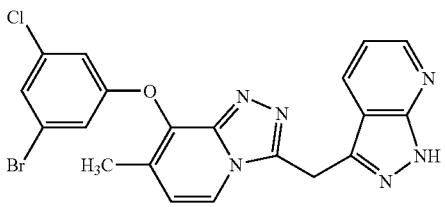

A mixture of N'-[3-(3-bromo-5-chlorophenoxy)-4-methylpyridin-2-yl]-2-(1H-pyrazolo[3,4-b]pyridin-3-yl)acetohydrazide (44 mg, 0.090 mmol) in phosphorus oxychloride (250 μL, 2.6 mmol) was heated to 120° C. for 35 minutes, after which the excess reagent was removed in vacuo and the residue partitioned between saturated aqueous NaHCO₃ (20 mL) and CH₂Cl₂ (2×20 mL). The combined extracts were concentrated in vacuo and the residue was purified on a Luna column (10μ, C18, 250×21.2 cm) eluting with 5-95% ACN/water with 0.1% TFA) to give the title compound. LRMS (M+1)=470.7.

Step 8: 3-chloro-5-{[7-methyl-3-(1H-pyrazolo[3,4-b]pyridin-3-ylmethyl)[1,2,4]triazolo[4,3-a]pyridin-8-yl]oxy}benzonitrile trifluoroacetate To a suspension of 8-(3-bromo-5-chlorophenoxy)-7-methyl-3-(1H-pyrazolo[3,4-b]pyridin-3-ylmethyl)[1,2,4]triazolo[4,3-a]pyridine (18.5 mg, 0.039 mmol) and zinc cyanide (6.94 mmol, 0.059 mmol) in DMF (500 μL) was added palladium tetratriphenylphosphine (13.68 mg, 0.012 mmol) and the mixture was heated to 90° C. for 2 hours, after which it was cooled to 25° C., filtered through Gelman Acrodisc and purified on a Luna column (10μ, C18, 250×21.2 cm) eluting with 5-95% ACN/water with 0.1% TFA) to give the title compound. $^1$H NMR (CD₃OD): δ 8.60 (d, 1H, J=8 Hz), 8.47 (d, 1H, J=5 Hz), 8.28 (d, 1H, J=7 Hz), 7.36 (m, 1H), 7.27 (m, 1H), 7.19 (m, 1H), 6.92 (m, 1H), 6.89 (d, 1H, J=7 Hz), 5.02 (s, 2H) and 2.31 (s, 3H) ppm. LRMS (M+1)=416.0.

Example 27

3-chloro-5-{[6-chloro-1-(1H-pyrazolo[3,4-b]pyridine-3-ylmethyl)-1,2,3,4-tetrahydroquinolin-5-yl]oxy}benzonitrile

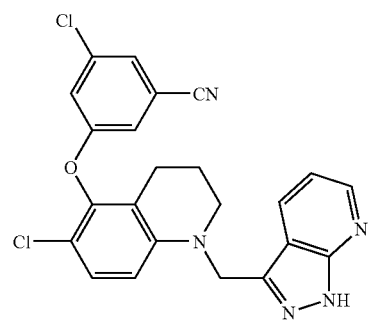

Step 1: Quinolin-5-yl acetate

TEA (960 μL, 6.89 mmol) was added to 5 hydroxy quinoline (1.0 g, 6.89 mmol) in 20 mL of DCM, after which the mixture was cooled to 0° C. and acetyl chloride was added dropwise (490 μL, 6.89 mmol). The reaction mixture was stirred for 1 hour at room temperature and then quenched with saturated aqueous sodium bicarbonate. The mixture was extracted with DCM, dried over sodium sulfate and concentrated. The crude acetate was purified on a silica gel column (10% to 80% EtOAc/hexanes) to afford the title product. LRMS (M+1)=188.3

Step 2: 1,2,3,4-tetrahydroquinolin-5-yl acetate

In accordance with *J. Org. Chem.* 1978, 43 (10), 1975-1980, PtO₂ (120 mg, 1.06 mmol) and concentrated HCl (20

μL) were added to a solution of quinolin-5-yl acetate (1.0 g, 5.34 mmol) in EtOH (30 mL) and the mixture was purged with N$_2$ followed by H$_2$. The mixture was then stirred at room temperature for 48 hours, at which point the starting material had been consumed as determined by LC-MS. The reaction mixture was then filtered through celite, and washed with MeOH, chloroform, and a small amount of TEA. The filtrate was concentrated under reduced pressure, and the resulting residue was purified on a silica gel column (10% to 80% EtOAc/hexanes) to afford the title product. LRMS (M+1) =192.3

Step 3: t-butyl 5-(acetyloxy)-3,4-dihydroquinoline-1 (2H)-carboxylate

To a cooled (0° C.) solution of 1,2,3,4-tetrahydroquinolin-5-yl acetate (5 g, 26.1 mmol) in 50 mL of acetonitrile was added TEA (3.46 mL, 26.1 mmol) followed by DMAP (3.19 g, 26.1 mmol). The mixture was stirred for 10 minutes after which Boc anhydride (11.4 g, 52.3 mmol) dissolved in acetonitrile (50 mL) was added. The mixture was warmed to room temperature and held at room temperature overnight. The reaction mixture was then diluted with EtOAc, washed successively with water and brine, dried over sodium sulfate, and concentrated. The crude Boc protected dihydroquinoline was purified on a silica gel column (5% to 35% EtOAc/hexanes) to afford the title product.
LRMS (M+1)=236.2 (M−56, loss of t-butyl)

Step 4: t-butyl 5-hydroxy-3,4-dihydroquinoline-1(2H)-carboxylate

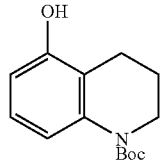

To a solution of t-butyl 5-(acetyloxy)-3,4-dihydroquinoline-1(2H)-carboxylate (770 mg, 2.64 mmol) in 10 mL of MeOH was added potassium carbonate (365 mg, 2.64 mmol), and the resulting mixture was stirred for 2 hours at room temperature and then filtered and concentrated in vacuo. The crude material was purified on a silica gel column (5% to 35% EtOAc/hexanes) to afford the desired product.
LRMS (M+1)=194.2 (M−56, loss of t-butyl)

Step 5: 6-chloro-t-butyl 5-hydroxy-3,4-dihydroquinoline-1(2H)-carboxylate t-butyl 5-hydroxy-3,4-dihydroquinoline-1(2H)-carboxylate (530 mg, 2.13 mmol) was dissolved in 20 mL of THF, after which NCS (284 mg, 2.13 mmol) was added and the mixture heated to reflux for 2 hours. The mixture was then cooled to room temperature and concentrated, and the crude reaction mixture was purified on a silica gel column (5% to 35% EtOAc/hexanes) to afford the desired product. LRMS (M+1)=228.2 (M−56, loss of t-butyl)

Step 6: 3-chloro-5-[(6-chloro-1,2,3,4-tetrahydroquinolin-5-yl)oxy]benzonitrile

Potassium carbonate (344 mg, 1.06 mmol) and 3-chloro-5-fluoro benzonitrile (164 mg, 1.06 mmol) were added to a solution of 6-chloro-t-butyl 5-hydroxy-3,4-dihydroquinoline-1(2H)-carboxylate (300 mg, 1.06 mmol) in DMSO (10 mL) in a process vial, and the mixture was heated to 140° C. for 10 minutes in a microwave reactor. The mixture was then cooled to room temperature, diluted with EtOAc, washed 3 times with water and once with brine, dried over sodium sulfate and concentrated. The crude material was purified on a silica gel column (5% to 35% EtOAc/hexanes) to afford the Boc protected intermediate. This material was dissolved in DCM (3 mL), after which TFA was added dropwise until the Boc-group had been removed as indicated by LC-MS. The mixture was then quenched with saturated sodium bicarbonate, extracted with chloroform, dried over sodium sulfate and concentrated in vacuo. The crude free base was used without further purification. HRMS (M+1)=319.0

Step 7: 3-chloro-5-{[6-chloro-1-(1H-pyrazolo[3,4-b] pyridine-3-ylmethyl)-1,2,3,4-tetrahydroquinolin-5-yl]oxy}benzonitrile 3-chloro-5-[(6-chloro-1,2,3,4-tetrahydroquinolin-5-yl) oxy]benzonitrile (120 mg, 0.376 mmol) was dissolved in DMSO (2 mL). To the resulting solution was added Cs$_2$CO$_3$ (245 mg, 0.751 mmol) followed by t-butyl 3-(bromomethyl)-1H-pyrazolo[3,4-b]pyridine-1-carboxylate (234 mg, 0.751 mmol). The mixture was stirred overnight at room temperature, diluted with EtOAc, washed 3 times with water and once with brine, dried over sodium sulfate, and concentrated. The crude material was purified on a silica gel column (10% to 85% EtOAc/hexanes) to afford the Boc-protected intermediate. The intermediate was then dissolved in DCM (1 mL) and TFA was added dropwise to the solution until deprotection was observed by LC-MS. The mixture was then quenched with saturated sodium bicarbonate, extracted with DCM, dried over sodium sulfate, and concentrated. The crude product was purified via reverse phase HPLC (5% to 95% ACN/ water/0.05% TFA) to afford the desired product as a TFA salt.
$^1$H NMR (CDCl$_3$): δ 8.59 (d, 1H), 8.0 (d, 1H), 7.1 (m, 3H), 6.92 (s, 1H), 6.8 (d, 1H), 4.8 (s, 2H), 3.40 (t, 2H), 2.58 (t, 2H), 1.98 (t, 2H). HRMS=450.0

Example 28

3-chloro-5-{[5-chloro-1-(2-hydroxyethyl)-1H-1,2,3-benzotriazol-4-yl]oxy}benzonitrile

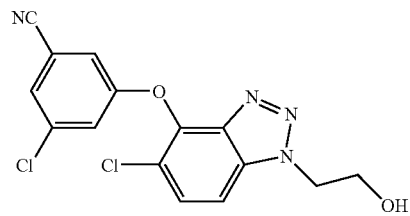

To a stirred solution of [5-chloro-4-(3-chloro-5-cyanophenoxy)-1H-1,2,3-benzotriazol-1-yl]acetic acid (50 mg, 0.138 mmol) (see step 2 in Example 16) at room temperature was added BH$_3$-THF complex (0.275 ml, 0.275 mmol). After 24 hours, the reaction was quenched with saturated aqueous sodium carbonate (1 mL) and extracted with ethyl acetate (2×20 mL). The combined organic fractions were dried (MgSO$_4$), filtered and the solvent was evaporated under reduced pressure. The resulting residue was purified by column chromatography on silica gel eluting with 0-5% MeOH/

CH$_2$Cl$_2$ to afford the title compound. $^1$H NMR (DMSO-d$_6$) δ 7.90 (d, J=8.9 Hz, 1H), 7.82 (m, 1H), 7.76 (d, J=8.9 Hz, 1H), 7.54 (m, 1H), 7.51 (m, 1H), 5.00 (t, J=5.6 Hz, 1H), 4.78 (t, J=5.1 Hz, 2H), 3.90 (dd, J=5.5 Hz, J=5.1 Hz, 2H). LRMS (M+1)=348.9.

Example 29

5-{[5-chloro-1-(1H-pyrazolo[3,4-b]pyridin-3-ylmethyl)-1H-1,2,3-benzotriazol-4-yl]oxy}isophthalonitrile

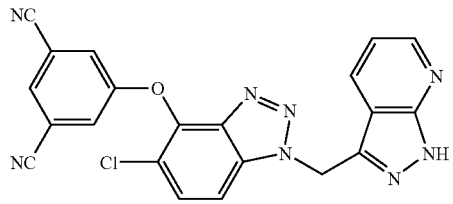

A partially purified product prepared in the manner described in Example 4A, step 5, except on a larger scale, was found to contain approximately 10 mol % 5-[(5-chloro-1H-1,2,3-benzotriazol-4-yl)oxy]isophthalonitrile in addition to 3-chloro-5-[(5-chloro-1H-1,2,3-benzotriazol-4-yl)oxy]benzonitrile. A solution of tert-butyl 3-(bromomethyl)-1H-pyrazolo[3,4-b]pyridine-1-carboxylate (Intermediate 1; 23 g, 74 mmol) in DMF (100 mL) was added to a suspension of the partially purified product (25 g, 82 mmol) and cesium carbonate (28 g, 86 mmol) in DMF (80 mL) at room temperature, and the resulting mixture was stirred for 1 hour at room temperature. The reaction mixture was then quenched with aqueous saturated ammonium chloride (200 mL), diluted with water (100 mL) and extracted with ethyl acetate (2×700 mL). The combined organic fractions were washed with dilute brine (3×500 mL), dried over MgSO$_4$, filtered and concentrated under reduced pressure. The resulting residue was adsorbed onto silica gel and subjected to automated silica gel chromatography eluting with a gradient of 25-50% ethyl acetate in hexanes to afford the crude title product. This mixture was then purified by reverse phase column chromatography eluting with 5-95% CH$_3$CN/H$_2$O (0.1% TFA) to yield the title compound. $^1$H NMR (DMSO-d$_6$) δ 8.53 (dd, J=4.6 Hz, J=1.5 Hz, 1H), 8.22 (m, 1H), 8.15 (dd, J=8.2 Hz, J=1.5 Hz, 1H), 8.00 (m, 2H), 7.92 (d, J=8.9 Hz, 1H), 7.78 (d, J=8.9 Hz, 1H), 7.21 (dd, J=8.0 Hz, J=4.5 Hz, 1H), 6.39 (s, 2H). LRMS (M+1)=426.9.

Example 30

Part A

Capsule Composition

A capsule formulation suitable for oral administration can be prepared by filling standard two-piece gelatin capsules each with 100 mg of the title compound of Example 1, 150 mg of lactose, 50 mg of cellulose, and 3 mg of stearic acid. Encapsulated oral compositions containing any one of the title compounds of Examples 2 to 29 can be similarly prepared.

Part B

Compressed Tablet Composition

| Ingredient | Amt per batch (wt. %) | Amount per Tablet (mg) |
|---|---|---|
| Compound of Example 1 | 12.5 | 125.0 |
| HPMCAS-LF | 50.0 | 500.0 |
| Lactose monohydrate | 33.25 | 332.5 |
| SiO$_2$, colloidal | 0.25 | 2.5 |
| Croscarmellose sodium | 3.00 | 30.0 |
| Magnesium stearate (intragranular) | 0.50 | 5.0 |
| Magnesium stearate (extragranular) | 0.50 | 5.0 |
| Total: | 100 | 1000 |

Compressed tablets containing 125 mg of the compound set forth in Example 1 (i.e., Compound I) were prepared as follows: Compound I and HPMCAS-LF were dissolved in acetone (66.4 g acetone per 1 g of Compound I) and the resulting solution was spray dried using a Niro SDMicro Spray Dryer (outlet gas temperature=53-63° C.; process nitrogen=30 kg/hour; atomizing nitrogen=2 kg/hour; solution feed rate=10-15 g/minutes; inlet gas temperature=97° C.-113° C.). The resulting powder was combined with lactose monohydrate, colloidal SiO$_2$, and croscarmellose sodium and the combination was blended in a V blender (Patterson Kelley) for 10 minutes. The blend was then lubricated for 5 minutes with intragranular magnesium stearate in the same blender, after which the blend was roller compacted into ribbons using a roller compactor (TFC Labo) fitted with a knurled roll at 4.0 MPa of pressure. The ribbons were then milled using a rotary fine granulator (TFC Labo) fitted with a 1.0 mm screen. The granules were then lubricated with extra-granular magnesium stearate in the V-blender for 5 minutes. The lubricated granules were then compressed on a tablet press (Manesty Single Station F-press) using capsule shaped tooling to provide tablets with a hardness range of 14.5-29.3 kP.

Tablets containing 25 mg of Compound I were prepared in the same manner as the 125 mg tablets, wherein the lubricated granules were compressed on a tablet press employing standard round concave tooling to provide tablets with a hardness of 6.1-22.7 kP. Tablets containing 5 mg of Compound I were also prepared in the same manner except that 20 wt. % HPC-MAS-LF, 35 wt. % microcrystalline cellulose, and 35.75 wt. % lactose monohydrate were employed in the preparation of the lubricated granules (the identity and concentration of the remaining components were unchanged). The lubricated granules were compressed on a tablet press employing standard round concave tooling to provide tablets with a hardness of 3.5-5.1 kP.

Example 31

ECL Assay for Inhibition of HIV Reverse Transcriptase

An assay to determine the in vitro inhibition of HIV reverse transcriptase by compounds of the present invention was conducted as follows: HIV-1 RT enzyme (0.1 nM) was combined with inhibitor or DMSO (10%) in assay buffer (50 mM Tris-HCl, pH 7.8, 1 mM dithiothreitol, 6 mM MgCl$_2$, 80 mM KCl, 0.025% CHAPS, 0.1 mM EGTA), and the mixture preincubated for 30 minutes at room temperature in microtiter plates (Costar #3359). 100 μL reaction mixtures were initiated with a combination of primer-template substrate (10 mM final concentration) and dNTPs (0.6 μM dNTPs, 1.25 μM BrdUTP). The heterodimeric nucleic acid substrate was generated by annealing the DNA primer pD500 (described in Shaw-Reid et al., *J. Biol. Chem.*, 278: 2777-2780; obtained from Integrated DNA Technologies) to t500, a 500 nucleotide RNA template created by in vitro transcription (see Shaw-Reid et al., *J. Biol. Chem.*, 278: 2777-2780). After 1 hour incubation at 37° C., reactions were quenched by 10 μL of 1 N NaOH. Microtiter plates were incubated for an additional 30 minutes at room temperature and then neutralized with 10 μL of 1 N HCl. A mixture of detection buffer containing ruthenylated anti-BrdU antibody and streptavidin coated magnetic beads were added to the plate and incubated at room temperature for 1.5 hours prior to quantification via electrochemiluminescence instrument. Representative compounds of the present invention exhibit inhibition of the reverse transcriptase enzyme in this assay. For example, the title compounds set forth above in Examples 1-4 were tested in the assay and all were found to have $IC_{50}$ values of less than 10 micromolar. Furthermore, the title compounds set forth above in Examples 1-7, 9-13 and 15-29 (Note—Examples 8 and 14 are prodrugs.) were tested in the assay and were found to have $IC_{50}$ values as set forth in Table B below.

Analogous assays were conducted substituting mutant HIV strains to determine the in vitro inhibition of compounds of the present invention against mutant HIV reverse transcriptase. In one strain the reverse transcriptase has the Y181C mutation and in the other strain the reverse transcriptase has the K103N mutation. The mutations were generated with the QUIKCHANGE site-directed mutagenesis kit (Stratagene). Representative compounds of the present invention exhibit inhibition of the reverse transcriptase enzyme in these assays. For example, the title compounds set forth above in Examples 1-4 were tested in the assays and were found to have $IC_{50}$ values of less than 10 micromolar in the Y181C assay and of less than 10 micromolar in the K103N assay. Furthermore, the title compounds set forth above in Examples 1-7, 9-13 and 15-29 were tested in the assays and were found to have $IC_{50}$ values as set forth in Table B:

TABLE B

| Example No. | ECL Assay (WT) $IC_{50}$ (nM) | ECL Assay (K103N) $IC_{50}$ (nM) | ECL Assay (Y181C) $IC_{50}$ (nM) |
| --- | --- | --- | --- |
| 1 | 0.35 | 0.57 | 0.60 |
| 2 | 3.9 | 12 | 25 |
| 3 | 0.6 | 1.7 | 1.9 |
| 4 | 0.24 | 0.41 | 0.44 |
| 5 | 0.62 | 1.3 | 1.8 |
| 6 | 0.4 | 0.53 | 0.82 |
| 7 | 0.92 | 4.1 | 1.7 |
| 9 | 61 | 74 | 137 |
| 10 | 1.5 | 13 | 13 |
| 11 | 18 | 52 | 30. |
| 12 | 0.45 | 0.94 | 0.89 |
| 13 | 1.0 | 3.0 | 2.4 |
| 15 | 2.4 | 12 | 1.5 |
| 16 | 1100 | >1800 | 790 |
| 17 | 38 | 79 | 74 |
| 18 | 2.1 | 2.6 | 3.7 |
| 19 | 0.57 | 0.93 | 0.77 |
| 20 | 2.1 | 55 | 2.5 |

TABLE B-continued

| Example No. | ECL Assay (WT) $IC_{50}$ (nM) | ECL Assay (K103N) $IC_{50}$ (nM) | ECL Assay (Y181C) $IC_{50}$ (nM) |
| --- | --- | --- | --- |
| 21 | 2.2 | 4.2 | 4.2 |
| 22 | 0.52 | 0.8 | 0.79 |
| 23 | 6.1 | 10 | 3.4 |
| 24 | 46 | 150 | 47 |
| 25 | 20 | 37 | 33 |
| 26 | 220 | 820 | 1200 |
| 27 | 160 | 640 | 160 |
| 28 | 68 | 210 | 77 |
| 29 | 0.9 | 1.4 | 1.3 |

1. WT = wild-type
2. The $IC_{50}$ values reported for Examples 2, 5-7, 10, 15-18, 20 and 22-29 are the results for a single run, and the values for the other examples are based on the results of at least 2 runs.

Example 32

Assay for Inhibition of HIV Replication

Assays for the inhibition of acute HIV-1 infection of T-lymphoid cells (alternatively referred to herein as the "spread assay") were conducted in accordance with Vacca, J. P. et al., *Proc. Natl. Acad. Sci. USA* 1994, 91: 4096. The assays tested for inhibition of wild type HIV-1 and of HIV strains containing the Y181C or K103N mutation. Representative compounds of the present invention exhibit inhibition of HIV replication in the assay employing wild-type HIV-1 and the mutant strains. For example, the compounds set forth in Examples 1 to 4 were found to have $CIC_{95}$ values of less than 10 micromolar in the assay employing the wild type strain. The compounds of Examples 1-4 exhibited $CIC_{95}$ values of less than 10 micromolar in the assay employing the Y181C mutant strain. The compounds of Examples 1 to 4 had $CIC_{95}$ values of less than 10 micromolar in the assay employing the K103N mutant strain. Furthermore, the compounds set forth in Examples 1-7, 9-13 and 15-29 were found to have $CIC_{95}$ values as set forth in Table C below in the assay employing the wild type strain. Table C also reports the $CIC_{95}$ values of the compounds of Examples 1-7, 9-13 and 15-29 obtained in the assays employing the Y181C mutant strain and the K103N mutant strain.

TABLE C

| Example No. | Spread (WT) $CIC_{95}$ (nM) (10% FBS) | Spread (K103N) $CIC_{95}$ (nM) (10% FBS) | Spread (Y181C) $CIC_{95}$ (nM) (10% FBS) |
| --- | --- | --- | --- |
| 1 | 13 | 17 | 69 |
| 2 | 521 | 2090 | — |
| 3 | 9 | 23 | 77 |
| 4 | 4 | 5 | 24 |
| 5 | 11 | 23 | 105 |
| 6 | 3 | <4 | 25 |
| 7 | 28 | 39 | 225 |
| 9 | 770 | 807 | — |
| 10 | 21 | 85 | 468 |
| 11 | 381 | 433 | — |
| 12 | 23 | 41 | 137 |
| 13 | 45 | 151 | 382 |
| 15 | >833 | >833 | — |
| 16 | >833 | >833 | — |
| 17 | 60 | 262 | >833 |
| 18 | 55 | 154 | 825 |
| 19 | 7 | 15 | 27 |
| 20 | 420 | >833 | — |
| 21 | 58 | 192 | 417 |

TABLE C-continued

| Example No. | Spread (WT) CIC95 (nM) (10% FBS) | Spread (K103N) CIC95 (nM) (10% FBS) | Spread (Y181C) CIC95 (nM) (10% FBS) |
|---|---|---|---|
| 22 | 4 | 9 | — |
| 23 | 96 | >833 | — |
| 24 | >833 | >833 | — |
| 25 | 115 | 362 | — |
| 26 | >833 | >833 | — |
| 27 | 3276 | 7734 | — |
| 28 | 557 | >833 | — |
| 29 | 2.5 | 3.1 | — |

1. WT = wild-type; FBS = fetal bovine serum.
2. All of the CIC95 values reported for Examples 2, 6, 15, 16, 20 and 23-29 are the results for a single run. The K103N and Y181C values reported for Examples 5, 7, 17-19 and 21 are the results for a single run. The K103N results reported for Example 22 is for a single run. The Y181C results for Examples 10 and 13 are for a single run. All of the other values are based on the results of at least 2 runs.

Example 33

Cytotoxicity

Cytotoxicity was determined by microscopic examination of the cells in each well in the spread assay, wherein a trained analyst observed each culture for any of the following morphological changes as compared to the control cultures: pH imbalance, cell abnormality, cytostatic, cytopathic, or crystallization (i.e., the compound is not soluble or forms crystals in the well). The toxicity value assigned to a given compound is the lowest concentration of the compound at which one of the above changes is observed. Representative compounds of the present invention exhibit no cytotoxicity at concentrations of up to their CIC95 value in the spread assay of Example 32. In particular, the compounds set forth in Examples 1-7, 9-13 and 15-29 exhibited no cytotoxicity at concentrations of up to 833 nanomolar.

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entireties into the disclosure.

What is claimed is:
1. A compound of Formula IIe, or a pharmaceutically acceptable salt thereof:

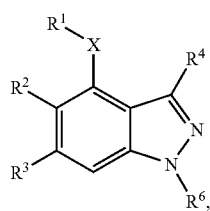

(IIe)

wherein:
X is O, S, S(O), S(O)$_2$, N(R$^A$), C(R$^A$)(R$^B$), or C(O);
R$^1$ is AryA or HetA;
R$^2$ and R$^3$ are each independently selected from the group consisting of:
(1) H,
(2) halogen,
(3) CN,
(4) NO$_2$,
(5) C(O)R$^A$,
(6) C(O)OR$^A$,
(7) C(O)N(R$^A$)R$^B$,
(8) SR$^A$,
(9) S(O)R$^A$,
(10) S(O)$_2$R$^A$,
(11) S(O)$_2$N(R$^A$)R$^B$,
(12) N(R$^A$)R$^B$,
(13) N(R$^A$)S(O)$_2$R$^B$,
(14) N(R$^A$)C(O)R$^B$,
(15) N(R$^A$)C(O)OR$^B$,
(16) N(R$^A$)S(O)$_2$N(R$^A$)R$^B$,
(17) OC(O)N(R$^A$)R$^B$,
(18) N(R$^A$)C(O)N(R$^A$)R$^B$,
(19) C$_{1-6}$ alkyl,
(20) C$_{1-6}$ haloalkyl,
(21) C$_{2-6}$ alkenyl,
(22) C$_{2-6}$ alkynyl,
(23) OH,
(24) O—C$_{1-6}$ alkyl,
(25) O—C$_{1-6}$ alkyl in which the alkyl is substituted with OR$^A$ or N(R$^A$)R$^B$,
(26) O—C$_{1-6}$ haloalkyl,
(27) C$_{1-6}$ alkyl substituted with from 1 to 3 substituents each of which is independently halogen (provided that the alkyl is further substituted with at least one non-halogen group), OH, O—C$_{1-6}$ alkyl, O—C$_{1-6}$ haloalkyl, CN, NO$_2$, N(R$^A$)R$^B$, C(O)N(R$^A$)R$^B$, C(O)R$^A$, CO$_2$R$^A$, SR$^A$, S(O)R$^A$, S(O)$_2$R$^A$, S(O)$_2$N(R$^A$)R$^B$, N(R$^A$)C(O)R$^B$, N(R$^A$)CO$_2$R$^B$, N(R$^A$)S(O)$_2$R$^B$, N(R$^A$)S(O)$_2$N(R$^A$)R$^B$, OC(O)N(R$^A$)R$^B$, or N(R$^A$)C(O)N(R$^A$)R$^B$,
(28) CycE,
(29) O-CycE,
(30) C(O)O-CycE,
(31) C(O)N(R$^A$)-CycE, and
(32) N(R$^A$)-CycE;
R$^4$ is selected from the group consisting of:
(1) H,
(2) C$_{1-6}$ alkyl,
(3) C$_{1-6}$ alkyl substituted with OH, O—C$_{1-6}$ alkyl, O—C$_{1-6}$ haloalkyl, CN, NO$_2$, N(R$^A$)R$^B$, C(O)N(R$^A$)R$^B$, C(O)R$^A$, CO$_2$R$^A$, SR$^A$, S(O)R$^A$, S(O)$_2$R$^A$, S(O)$_2$N(R$^A$)R$^B$, N(R$^A$)C(O)R$^B$, N(R$^A$)CO$_2$R$^B$, N(R$^A$)S(O)$_2$R$^B$, N(R$^A$)S(O)$_2$N(R$^A$)R$^B$, OC(O)N(R$^A$)R$^B$, N(R$^A$)C(O)N(R$^A$)R$^B$, or N(R$^A$)C(O)C(O)N(R$^A$)R$^B$,
(4) O—C$_{1-6}$ alkyl,
(5) C$_{1-6}$ haloalkyl,
(6) O—C$_{1-6}$ haloalkyl,
(7) OH,
(8) halogen,
(9) CN,
(10) NO$_2$,
(11) C(O)N(R$^A$)R$^B$,
(12) C(O)R$^A$,
(13) C(O)—C$_{1-6}$ haloalkyl,
(14) C(O)OR$^A$,
(15) SR$^A$,
(16) S(O)R$^A$,
(17) S(O)$_2$R$^A$,
(18) S(O)$_2$N(R$^A$)R$^B$,
(19) N(R$^A$)R$^B$,
(20) N(R$^A$)S(O)$_2$R$^B$,
(21) N(R$^A$)C(O)R$^B$,
(22) N(R$^A$)C(O)OR$^B$,
(23) N(R$^A$)S(O)$_2$N(R$^A$)R$^B$,

(24) OC(O)N($R^A$)$R^B$, and
(25) N($R^A$)C(O)N($R^A$)$R^B$;

$R^6$ is:

(1)

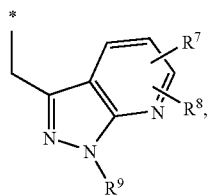

wherein each ring N is optionally an N-oxide,
(2) *-CH$_2$C(O)N($R^A$)-AryB,
(3) *-CH$_2$C(O)N($R^A$)-HetB,
(4) *-CH$_2$C(O)N($R^A$)—C$_{1-3}$ alkylene-AryB,
(5) *-CH$_2$C(O)N($R^A$)—C$_{1-3}$ alkylene-HetB,
(6) *-CH$_2$C(O)O—C$_{1-3}$ alkylene-AryB,
(7) *-CH$_2$C(O)O—C$_{1-3}$ alkylene-HetB,
(8) *-CH$_2$-HetB,
(9) *-CH$_2$C(O)-HetB,
(10) *-CH$_2$C(O)-HetC, or
(11) *-CH$_2$CH$_2$OH;
wherein the asterisk denotes the point of attachment to the rest of the compound;

$R^7$ and $R^8$ are each independently selected from the group consisting of:
(1) H,
(2) OH,
(3) halogen,
(4) CN,
(5) NO$_2$,
(6) C$_{1-6}$ alkyl,
(7) C$_{1-6}$ alkyl substituted with OH, O—C$_{1-6}$ alkyl, O—C$_{1-6}$ haloalkyl, CN, NO$_2$, N($R^A$)$R^B$, C(O)N($R^A$)$R^B$, C(O)$R^A$, CO$_2$$R^A$, S$R^A$, S(O)$R^A$, S(O)$_2$$R^A$, S(O)$_2$N($R^A$)$R^B$, N($R^A$)C(O)$R^B$, N($R^A$)CO$_2$$R^B$, N($R^A$)S(O)$_2$$R^B$, N($R^A$)S(O)$_2$N($R^A$)$R^B$, OC(O)N($R^A$)$R^B$, N($R^A$)C(O)N($R^A$)$R^B$, or N($R^A$)C(O)C(O)N($R^A$)$R^B$,
(8) O—C$_{1-6}$ alkyl,
(9) O—C$_{1-6}$ alkyl in which the alkyl is substituted with O—C$_{1-6}$ alkyl, N($R^A$)$R^B$, C(O)N($R^A$)$R^B$, C(O)$R^A$, or CO$_2$$R^A$,
(10) C$_{1-6}$ haloalkyl,
(11) O—C$_{1-6}$ haloalkyl,
(12) N($R^C$)$R^D$,
(13) N($R^A$)—C$_{1-6}$ alkylene-N($R^C$)$R^D$,
(14) C(O)N($R^A$)$R^B$,
(15) C(O)$R^A$,
(16) C(O)—C$_{1-6}$ haloalkyl,
(17) C(O)O$R^A$,
(18) S$R^A$,
(19) S(O)$R^A$,
(20) S(O)$_2$$R^A$,
(21) S(O)$_2$N($R^A$)$R^B$,
(22) CycE,
(23) O-CycE,
(24) C(O)O-CycE,
(25) C(O)N($R^A$)-CycE,
(26) N($R^A$)-CycE,
(27) C$_{1-6}$ alkyl substituted with CycE,
(28) O—C$_{1-6}$ alkyl substituted with N($R^A$)-CycE,
(29) O—C$_{1-6}$ alkyl substituted with C(O)-CycE,
(30) HetE,
(31) N($R^A$)S(O)$_2$$R^B$,
(32) N($R^A$)C(O)$R^B$, and
(33) N($R^A$)C(O)N($R^A$)$R^B$;

$R^9$ is H or C$_{1-6}$ alkyl;
each $R^A$ is independently H, C$_{1-6}$ alkyl, or C$_{1-6}$ haloalkyl;
each $R^B$ is independently H, C$_{1-6}$ alkyl, or C$_{1-6}$ haloalkyl;
each $R^C$ is independently H, C$_{1-6}$ alkyl, or C$_{1-6}$ haloalkyl;
each $R^D$ is independently H, C$_{1-6}$ alkyl, or C$_{1-6}$ haloalkyl;
alternatively and independently each pair of $R^C$ and $R^D$ together with the N atom to which they are both attached form a 4- to 7-membered, saturated or mono-unsaturated monocyclic ring optionally containing 1 heteroatom in addition to the nitrogen attached to $R^C$ and $R^D$ selected from N, O, and S, where the S is optionally oxidized to S(O) or S(O)$_2$; wherein the monocyclic ring is optionally substituted with 1 or 2 substituents each of which is independently: (1) C$_{1-6}$ alkyl, (2) C$_{1-6}$ fluoroalkyl, (3) (CH$_2$)$_{1-2}$G wherein G is OH, O—C$_{1-6}$ alkyl, O—C$_{1-6}$ fluoroalkyl, N($R^A$)$R^B$, C(O)N($R^A$)$R^B$, C(O)$R^A$, CO$_2$$R^A$, or SO$_2$$R^A$, (4) O—C$_{1-6}$ alkyl, (5) O—C$_{1-6}$ fluoroalkyl, (6) OH, (7) oxo, (8) halogen, (9) C(O)N($R^A$)$R^B$, (10) C(O)$R^A$, (11) C(O)—C$_{1-6}$ fluoroalkyl, (12) C(O)O$R^A$, or (13) S(O)$_2$$R^A$;

AryA is aryl optionally substituted with a total of from 1 to 6 substituents, wherein:
(i) from zero to 6 substituents are each independently:
(1) C$_{1-6}$ alkyl,
(2) C$_{1-6}$ alkyl substituted with OH, O—C$_{1-6}$ alkyl, O—C$_{1-6}$ haloalkyl, CN, NO$_2$, N($R^A$)$R^B$, C(O)N($R^A$)$R^B$, C(O)$R^A$, CO$_2$$R^A$, S$R^A$, S(O)$R^A$, S(O)$_2$$R^A$, S(O)$_2$N($R^A$)$R^B$, N($R^A$)C(O)$R^B$, N($R^A$)CO$_2$$R^B$, N($R^A$)S(O)$_2$$R^B$, N($R^A$)S(O)$_2$N($R^A$)$R^B$, OC(O)N($R^A$)$R^B$, N($R^A$)C(O)N($R^A$)$R^B$, or N($R^A$)C(O)C(O)N($R^A$)$R^B$,
(3) O—C$_{1-6}$ alkyl,
(4) O—C$_{1-6}$ alkyl, in which the alkyl is substituted with OH, O—C$_{1-6}$ alkyl, O—C$_{1-6}$ haloalkyl, CN, NO$_2$, N($R^A$)$R^B$, C(O)N($R^A$)$R^B$, C(O)$R^A$, CO$_2$$R^A$, S$R^A$, S(O)$R^A$, S(O)$_2$$R^A$, S(O)$_2$N($R^A$)$R^B$, N($R^A$)C(O)$R^B$, N($R^A$)CO$_2$$R^B$, N($R^A$)S(O)$_2$$R^B$, N($R^A$)S(O)$_2$N($R^A$)$R^B$, OC(O)N($R^A$)$R^B$, N($R^A$)C(O)N($R^A$)$R^B$, or N($R^A$)C(O)C(O)N($R^A$)$R^B$,
(5) C$_{1-6}$ haloalkyl,
(6) O—C$_{1-6}$ haloalkyl,
(7) OH,
(8) halogen,
(9) CN,
(10) NO$_2$,
(11) N($R^A$)$R^B$,
(12) C(O)N($R^A$)$R^B$,
(13) C(O)$R^A$,
(14) C(O)—C$_{1-6}$ haloalkyl,
(15) C(O)O$R^A$,
(16) OC(O)N($R^A$)$R^B$,
(17) S$R^A$,
(18) S(O)$R^A$,
(19) S(O)$_2$$R^A$,
(20) S(O)$_2$N($R^A$)$R^B$,
(21) N($R^A$)S(O)$_2$$R^B$,
(22) N($R^A$)S(O)$_2$N($R^A$)$R^B$,
(23) N($R^A$)C(O)$R^B$,
(24) N($R^A$)C(O)N($R^A$)$R^B$,
(25) N($R^A$)C(O)—C(O)N($R^A$)$R^B$,
(26) N($R^A$)CO$_2$$R^B$,

(27) $C_{2-6}$ alkenyl substituted with CN, $NO_2$, $N(R^A)R^B$, or $C(O)N(R^A)R^B$, or

(28) $C_{2-6}$ alkynyl substituted with CN, $NO_2$, $N(R^A)R^B$, or $C(O)N(R^A)R^B$, and (ii) from zero to 2 substituents are each independently:
(1) CycE,
(2) AryE,
(3) O-AryE,
(4) HetE,
(5) HetF,
(6) $C_{1-6}$ alkyl substituted with CycE, AryE, O-AryE, HetE, or HetF,
(7) $C_{2-6}$ alkenyl substituted with AryE,
(8) $C_{2-6}$ alkynyl substituted with AryE, or
(9) $C_{2-6}$ alkynyl substituted with HetE;

HetA is heteroaryl which is optionally substituted with a total of from 1 to 6 substituents, wherein:

(i) from zero to 6 substituents are each independently:
(1) $C_{1-6}$ alkyl,
(2) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(3) O—$C_{1-6}$ alkyl,
(4) O—$C_{1-6}$ alkyl, in which the alkyl is substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(5) $C_{1-6}$ haloalkyl,
(6) O—$C_{1-6}$ haloalkyl,
(7) OH,
(8) oxo,
(9) halogen,
(10) CN,
(11) $NO_2$,
(12) $N(R^A)R^B$,
(13) $C(O)N(R^A)R^B$,
(14) $C(O)R^A$,
(15) C(O)—$C_{1-6}$ haloalkyl,
(16) $C(O)OR^A$,
(17) $OC(O)N(R^A)R^B$,
(18) $SR^A$,
(19) $S(O)R^A$,
(20) $S(O)_2R^A$,
(21) $S(O)_2N(R^A)R^B$,
(22) $N(R^A)S(O)_2R^B$,
(23) $N(R^A)S(O)_2N(R^A)R^B$,
(24) $N(R^A)C(O)R^B$,
(25) $N(R^A)C(O)N(R^A)R^B$,
(26) $N(R^A)C(O)$—$C(O)N(R^A)R^B$, or
(27) $N(R^A)CO_2R^B$, and (ii) from zero to 2 substituents are each independently:
(1) CycE,
(2) AryE,
(3) O-AryE,
(4) HetE,
(5) HetF, or
(6) $C_{1-6}$ alkyl substituted with CycE, AryE, O-AryE, HetE, or HetF;

aryl is (i) phenyl, (ii) a 9- or 10-membered bicyclic, fused carbocyclic ring system in which at least one ring is aromatic, or (iii) an 11- to 14-membered tricyclic, fused carbocyclic ring system in which at least one ring is aromatic;

heteroaryl is (i) a 5- or 6-membered heteroaromatic ring containing from 1 to 4 heteroatoms independently selected from N, O and S, wherein each N is optionally in the form of an oxide, (ii) a 9- or 10-membered bicyclic fused ring system, or (iii) an 11- to 16-membered tricyclic fused ring system, wherein the fused ring system of (ii) or (iii) contains from 1 to 6 heteroatoms independently selected from N, O and S, wherein each ring in the fused ring system contains zero, one or more than one heteroatom, at least one ring is aromatic, each N is optionally in the form of an oxide, and each S in a ring which is not aromatic is optionally S(O) or $S(O)_2$;

AryB independently has the same definition as AryE;
HetB independently has the same definition as HetE;
HetC independently has the same definition as HetF;

each CycE is independently $C_{3-8}$ cycloalkyl which is optionally substituted with from 1 to 4 substituents each of which is independently halogen, $C_{1-6}$ alkyl, OH, O—$C_{1-6}$ alkyl, $C_{1-6}$ haloalkyl, or O—$C_{1-6}$ haloalkyl;

each AryE is independently phenyl or naphthyl, wherein the phenyl or naphthyl is optionally substituted with from 1 to 5 substituents each of which is independently halogen, CN, $NO_2$, $C_{1-6}$ alkyl, $C_{1-6}$ haloalkyl, OH, O—$C_{1-6}$ alkyl, O—$C_{1-6}$ haloalkyl, $C(O)N(R^A)R^B$, $C(O)R^A$, $CO_2R^A$, $SR^A$, $S(O)R^A$, $SO_2R^A$, $SO_2N(R^A)R^B$, or $SO_2N(R^A)C(O)R^B$;

each HetE is independently a 5- or 6-membered heteroaromatic ring containing from 1 to 4 heteroatoms independently selected from N, O and S, wherein each N is optionally in the form of an oxide, and wherein the heteroaromatic ring is optionally substituted with from 1 to 4 substituents each of which is independently halogen, CN, $NO_2$, $C_{1-6}$ alkyl, $C_{1-6}$ haloalkyl, O—$C_{1-6}$ alkyl, O—$C_{1-6}$ haloalkyl, OH, $N(R^A)R^B$, $N(R^A)C(O)N(R^A)R^B$, $N(R^A)CO_2R^B$, $C(O)N(R^A)R^B$, $C(O)R^A$, $CO_2R^A$, $SO_2R^A$, $SO_2N(R^A)R^B$, or phenyl, with the proviso that no more than 1 of the optional substituents is phenyl; and each HetF is independently a 4- to 7-membered, saturated or mono-unsaturated heterocyclic ring containing at least one carbon atom and from 1 to 4 heteroatoms independently selected from N, O and S, where each S is optionally oxidized to S(O) or $S(O)_2$, and wherein the saturated or mono-unsaturated heterocyclic ring is optionally substituted with a total of from 1 to 4 substituents, each of which is independently halogen, CN, $C_{1-6}$ alkyl, OH, oxo, O—$C_{1-6}$ alkyl, $C_{1-6}$ haloalkyl, O—$C_{1-6}$ haloalkyl, $C(O)N(R^A)R^B$, $C(O)R^A$, $CO_2R^A$, $SO_2R^A$, or $SO_2N(R^A)R^B$.

2. A compound according to claim 1, or a pharmaceutically acceptable salt thereof, wherein:

X is O;
$R^1$ is AryA;
$R^2$ and $R^3$ are each independently selected from the group consisting of:
(1) H,
(2) halogen,
(3) $N(R^A)R^B$,
(4) $C_{1-6}$ alkyl,
(5) $C_{1-6}$ fluoroalkyl,
(6) O—$C_{1-6}$ alkyl, and
(7) O—$C_{1-6}$ fluoroalkyl;

$R^4$ is selected from the group consisting of:
(1) H,
(2) $C_{1-6}$ alkyl, (3) O—C$_{1-6}$ alkyl,
(4) C$_{1-6}$ fluoroalkyl,
(5) O—C$_{1-6}$ fluoroalkyl, and
(6) halogen;

R$^6$ is:

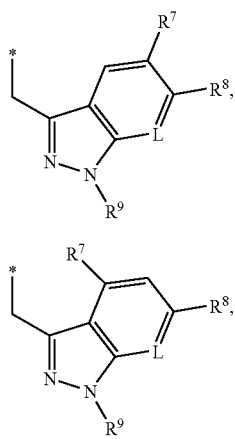

(3) *-CH$_2$C(O)N(R$^A$)-AryB,
(4) *-CH$_2$C(O)N(R$^A$)-HetB,
(5) *-CH$_2$C(O)N(R$^A$)—C$_{1-3}$ alkylene-AryB,
(6) *-CH$_2$C(O)N(R$^A$)—C$_{1-3}$ alkylene-HetB,
(7) *-CH$_2$C(O)O—C$_{1-3}$ alkylene-AryB,
(8) *-CH$_2$-HetB,
(9) *-CH$_2$C(O)-HetB,
(10) *-CH$_2$C(O)-HetC, or
(11) *-CH$_2$CH$_2$OH;

L is N or N oxide;

R$^7$ and R$^8$ are each independently selected from the group consisting of:
(1) H,
(2) OH,
(3) halogen,
(4) CN,
(5) NO$_2$,
(6) C$_{1-6}$ alkyl,
(7) O—C$_{1-6}$ alkyl,
(8) O(CH$_2$)$_{2-3}$N(R$^A$)R$^B$,
(9) O(CH$_2$)$_{1-3}$C(O)R$^A$,
(10) C$_{1-6}$ fluoroalkyl,
(11) O—C$_{1-6}$ fluoroalkyl,
(12) N(R$^C$)R$^D$,
(13) N(R$^A$)—(CH$_2$)$_{2-3}$—N(R$^C$)R$^D$,
(14) C(O)N(R$^A$)R$^B$,
(15) C(O)R$^A$,
(16) C(O)OR$^A$,
(17) SR$^A$,
(18) S(O)R$^A$,
(19) S(O)$_2$R$^A$, and
(20) S(O)$_2$N(R$^A$)R$^B$;

R$^9$ is H or C$_{1-4}$ alkyl;

AryA is phenyl or naphthyl, wherein the phenyl is optionally substituted with from 1 to 3 substituents each of which is independently C$_{1-6}$ alkyl, O—C$_{1-6}$ alkyl, CF$_3$, OCF$_3$, OH, halogen, CN, NO$_2$, N(R$^A$)R$^B$, C(O)N(R$^A$)R$^B$, C(O)R$^A$, C(O)CF$_3$, CO$_2$R$^A$, SO$_2$R$^A$, CH═CH—(CH$_2$)$_{0-2}$CN, C≡C—(CH$_2$)$_{1-2}$N(R$^A$)R$^B$, or C$_{1-6}$ alkylene-N(R$^A$)R$^B$;

AryB is phenyl which is optionally substituted with from 1 to 2 substituents each of which is independently Cl, Br, F, CN, NO$_2$, C$_{1-4}$ alkyl, CF$_3$, OH, O—C$_{1-4}$ alkyl, OCF$_3$, C(O)N(R$^A$)R$^B$, C(O)R$^A$, CO$_2$R$^A$, SO$_2$R$^A$, or SO$_2$N(R$^A$)R$^B$;

HetB is a heteroaromatic ring selected from the group consisting of pyrrolyl, pyrazolyl, oxazolyl, thiazolyl, imidazolyl, oxadiazolyl, pyridyl and pyrimidinyl, wherein the heteroaromatic ring is optionally substituted with from 1 to 2 substituents, each of which is independently Cl, Br, F, CN, NO$_2$, C$_{1-4}$ alkyl, CF$_3$, OH, O—C$_{1-4}$ alkyl, OCF$_3$, C(O)N(R$^A$)R$^B$, C(O)R$^A$, CO$_2$R$^A$, SO$_2$R$^A$, SO$_2$N(R$^A$)R$^B$, or phenyl, with the proviso that no more than 1 of the optional substituents is phenyl;

HetC is a saturated heterocyclic ring selected from the group consisting of 1-pyrrolidinyl, 1-piperidinyl, 4-morpholinyl, 4-thiomorpholinyl in which the S is optionally oxidized to S(O) or S(O)$_2$, and 1-piperazinyl, wherein the saturated heterocyclic ring is optionally substituted with from 1 to 2 substituents each of which is Cl, Br, F, CN, C$_{1-4}$ alkyl, OH, oxo, O—C$_{1-4}$ alkyl, CF$_3$, OCF$_3$, C(O)N(R$^A$)R$^B$, C(O)R$^A$, CO$_2$R$^A$, SO$_2$R$^A$, or SO$_2$N(R$^A$)R$^B$;

each R$^A$ is independently H or C$_{1-6}$ alkyl;
each R$^B$ is independently H or C$_{1-6}$ alkyl;
each R$^C$ is independently H or C$_{1-6}$ alkyl;
each R$^D$ is independently H or C$_{1-6}$ alkyl; and alternatively and independently each pair of R$^C$ and R$^D$ together with the N atom to which they are both attached form a 4- to 7-membered, saturated monocyclic ring optionally containing 1 heteroatom in addition to the nitrogen attached to R$^C$ and R$^D$ selected from N, O, and S, where the S is optionally oxidized to S(O) or S(O)$_2$; and wherein the monocyclic ring is optionally substituted with 1 or 2 substituents each of which is independently: (1) C$_{1-4}$ alkyl, (2) CF$_3$, (3) C(O)N(R$^A$)R$^B$, (4) C(O)R$^A$, (5) C(O)—CF$_3$, (6) C(O)OR$^A$, or (7) S(O)$_2$R$^A$.

3. A compound according to claim 2, or a pharmaceutically acceptable salt thereof, which is a compound of Formula IX:

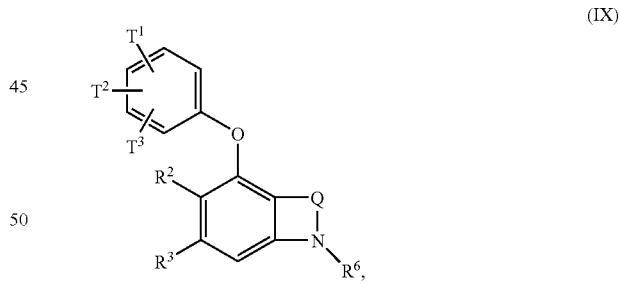

wherein:
T1 and T2 and T3 are each independently H, C$_{1-4}$ alkyl, halogen, CN, CH═CH—CN, C(O)R$^A$, or (CH$_2$)$_{1-2}$N(R$^A$)R$^B$;

R$^2$ and R$^3$ are each independently selected from the group consisting of:
(1) H,
(2) halogen,
(3) N(R$^A$)R$^B$,
(4) C$_{1-4}$ alkyl,
(5) CF$_3$,
(6) O—C$_{1-4}$ alkyl, and
(7) OCF$_3$;

R⁶ is:

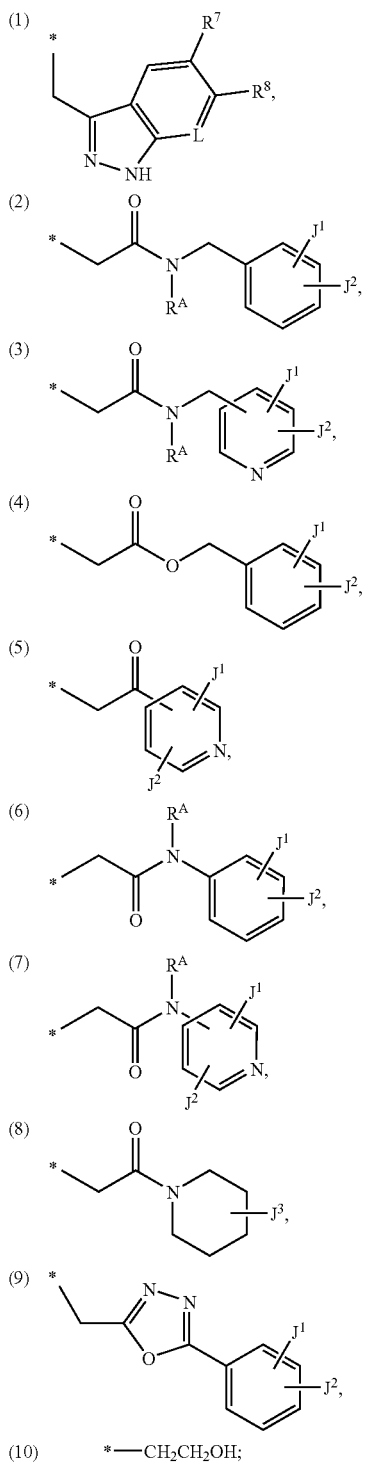

(10)     *—CH₂CH₂OH;

J¹ and J² are each independently H, Cl, Br, F, CN, NO₂, $C_{1-4}$ alkyl, $CF_3$, OH, O—$C_{1-4}$ alkyl, $OCF_3$, $C(O)N(R^A)R^B$, $C(O)R^A$, $CO_2R^A$, $SO_2R^A$, or $SO_2N(R^A)R^B$;

J³ is H, Cl, Br, F, CN, $C_{1-4}$ alkyl, OH, oxo, O—$C_{1-4}$ alkyl, $CF_3$, $OCF_3$, $C(O)NH_2$, $C(O)N(H)CH_3$, $C(O)N(R^A)R^B$, $C(O)R^A$, $CO_2R^A$, $SO_2R^A$, or $SO_2N(R^A)R^B$;

L is N or N oxide;

Q is —$C(R^4)$=N—, wherein the left-most atom in Q is the atom directly attached to the fused benzo;

R⁴ is selected from the group consisting of:
(1) H,
(2) $C_{1-4}$ alkyl,
(3) O—$C_{1-4}$ alkyl,
(4) $CF_3$,
(5) $OCF_3$, and
(6) halogen;

R⁷ and R⁸ are each independently selected from the group consisting of:
(1) H,
(2) OH,
(3) halogen,
(4) CN,
(5) $NO_2$,
(6) $C_{1-4}$ alkyl,
(7) O—$C_{1-4}$ alkyl,
(8) $O(CH_2)_{2-3}N(R^A)R^B$,
(9) $O(CH_2)_{1-3}C(O)R^A$,
(10) $CF_3$,
(11) $OCF_3$,
(12) $O(CH_2)_{1-2}CF_3$,
(12) $N(R^C)R^D$,
(13) $N(R^A)$—$(CH_2)_{2-3}$—$N(R^C)R^D$, and
(14) $C(O)N(R^A)R^B$;

each $R^A$ is independently H or $C_{1-4}$ alkyl;
each $R^B$ is independently H or $C_{1-4}$ alkyl;
each $R^C$ is independently H or $C_{1-4}$ alkyl;
each $R^D$ is independently H or $C_{1-4}$ alkyl; and alternatively and independently each pair of $R^C$ and $R^D$ together with the N atom to which they are both attached form a saturated monocyclic ring selected from the group consisting of:

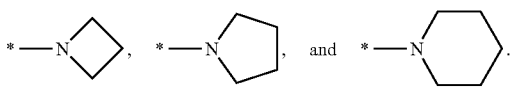

4. A compound according to claim 3, or a pharmaceutically acceptable salt thereof, which is a compound of Formula IXa:

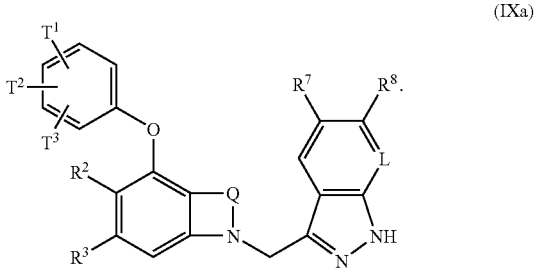

(IXa)

5. A compound according to claim 4, or a pharmaceutically acceptable salt thereof, which is a compound of Formula IXb:

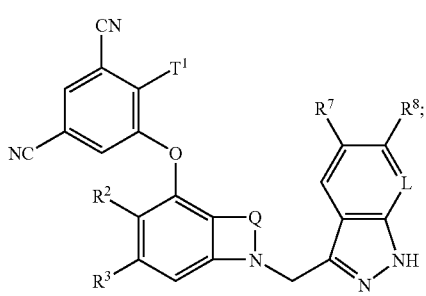

(IXb)

wherein:
Ti is H or Cl;
$R^2$ and $R^3$ are each independently selected from the group consisting of H, Cl, Br, F and $C_{1-4}$ alkyl;
$R^4$ is H, $C_{1-4}$ alkyl, Cl, Br, or F; and
one of $R^7$ and $R^8$ is H, OH, Cl, Br, F, $CH_3$, $OCH_3$, $O(CH_2)_{2-3}NH_2$, $CF_3$, $OCF_3$, $OCH_2CF_3$, $NH_2$, $N(H)CH_3$, $N(CH_3)_2$, $C(O)NH_2$, $C(O)N(H)CH_3$, or $C(O)N(CH_3)_2$; and the other of $R^7$ and $R^8$ is H.

6. A compound according to claim 5, or a pharmaceutically acceptable salt thereof, wherein Q is —CH=N—.

7. A compound according to claim 4, or a pharmaceutically acceptable salt thereof, which is a compound of Formula IXc:

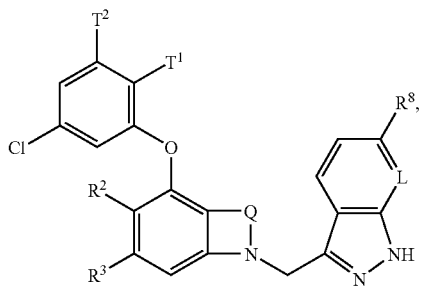

(IXc)

wherein:
Ti is H or Cl;
$T^2$ is CN, CH(O), $CH_2NH_2$, or $CH_2N(H)CH_3$;
$R^2$ and $R^3$ are each independently selected from the group consisting of H, Cl, Br, F and $C_{1-4}$ alkyl;
$R^4$ is H, $C_{1-4}$ alkyl, Cl, Br, or F; and
$R^8$ is H, OH, Cl, Br, F, $CH_3$, $OCH_3$, $O(CH_2)_{2-3}NH_2$, $CF_3$, $OCF_3$, $OCH_2CF_3$, $NH_2$, $N(H)CH_3$, $N(CH_3)_2$, $C(O)NH_2$, $C(O)N(H)CH_3$, or $C(O)N(CH_3)_2$.

8. A compound according to claim 7, or a pharmaceutically acceptable salt thereof, wherein Q is —CH=N—.

9. A compound according to claim 3, or a pharmaceutically acceptable salt thereof, which is a compound of Formula IXd:

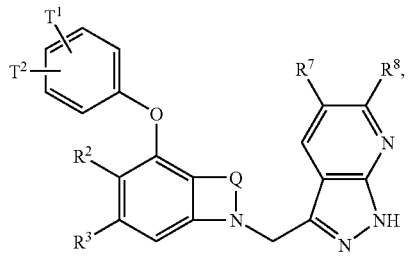

(IXd)

wherein $T^1$ and $T^2$ are each independently H, $C_{1-4}$ alkyl, halogen, CN, or CH=CH—CN.

10. A compound according to claim 9, or a pharmaceutically acceptable salt thereof, which is a compound of Formula IXe:

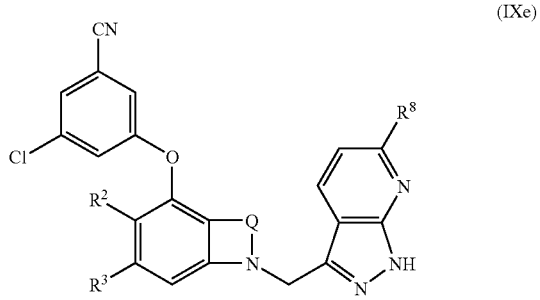

(IXe)

wherein:
$R^2$ and $R^3$ are each independently selected from the group consisting of H, Cl, Br, F and $C_{1-4}$ alkyl;
$R^4$ is H, $C_{1-4}$ alkyl, Cl, Br, or F; and
$R^8$ is H, OH, Cl, Br, F, $CH_3$, $OCH_3$, $O(CH_2)_{2-3}NH_2$, $CF_3$, $OCF_3$, $OCH_2CF_3$, $NH_2$, $N(H)CH_3$, $N(CH_3)_2$, $C(O)NH_2$, $C(O)N(H)CH_3$, or $C(O)N(CH_3)_2$.

11. A compound according to claim 10, or a pharmaceutically acceptable salt thereof, wherein:
$R^2$ is Br or Cl;
$R^3$ is H; and
$R^8$ is H or $NH_2$.

12. A compound according to claim 1 selected from the group consisting of:

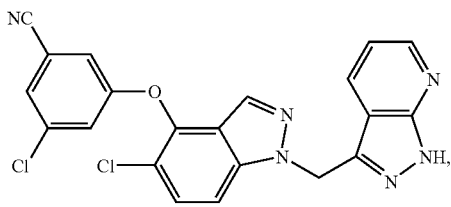

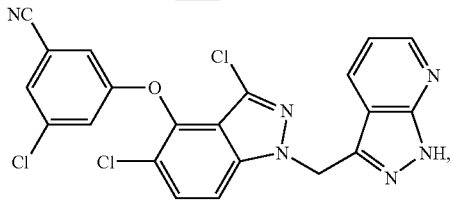

-continued

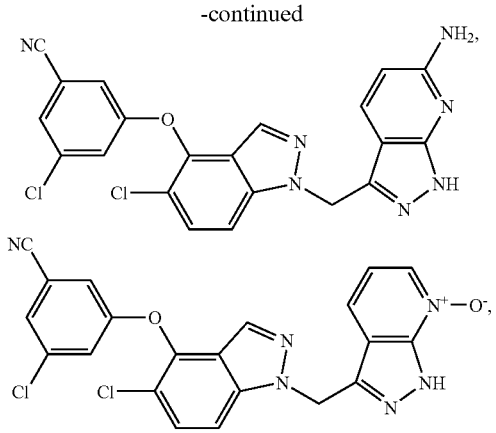

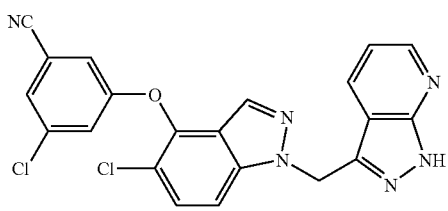

and pharmaceutically acceptable salts thereof.

13. A pharmaceutical composition comprising an effective amount of a compound according to claim 1, or a pharmaceutically acceptable salt thereof, and a pharmaceutically acceptable carrier.

14. A method for the treatment of HIV-1 infection, wherein the method comprises administering to a subject in need thereof an effective amount of a compound according to claim 1, or a pharmaceutically acceptable salt thereof.

15. A compound according to claim 12, which is:

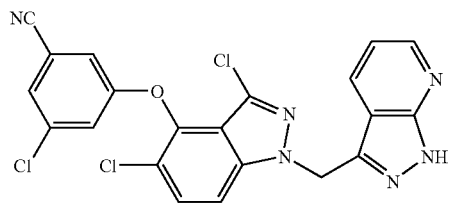

or a pharmaceutically acceptable salt thereof.

16. A compound according to claim 12, which is:

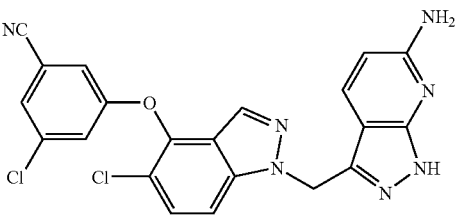

or a pharmaceutically acceptable salt thereof.

17. A compound according to claim 12, which is:

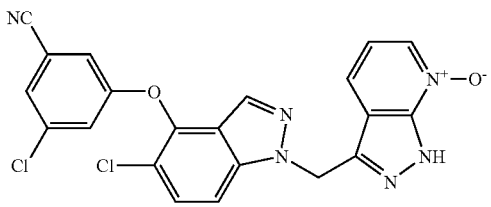

or a pharmaceutically acceptable salt thereof.

18. A compound according to claim 12, which is:

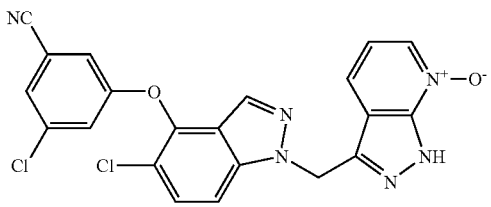

or a pharmaceutically acceptable salt thereof.

* * * * *